(12) United States Patent
Lynn et al.

(10) Patent No.: US 12,291,651 B2
(45) Date of Patent: May 6, 2025

(54) LIQUID CRYSTAL-INFUSED SLIPPERY ANTI-FOULING SURFACES

(71) Applicant: Wisconsin Alumni Research Foundation, Madison, WI (US)

(72) Inventors: David Lynn, Middleton, WI (US); Harshit Agarwal, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 250 days.

(21) Appl. No.: 17/714,583

(22) Filed: Apr. 6, 2022

(65) Prior Publication Data

US 2022/0332954 A1 Oct. 20, 2022

Related U.S. Application Data

(60) Provisional application No. 63/171,881, filed on Apr. 7, 2021.

(51) Int. Cl.
*C09D 5/16* (2006.01)
*C09D 5/00* (2006.01)
(Continued)

(52) U.S. Cl.
CPC ............. *C09D 5/16* (2013.01); *C09D 5/00* (2013.01); *C09D 5/1681* (2013.01);
(Continued)

(58) Field of Classification Search
CPC .......... C09D 5/00; C09D 5/16; C09D 5/1681; C10M 109/00; C10M 171/00; C10M 171/007; C10N 2020/079; C10N 2040/00; C10N 2050/023; C10N 2050/08; C12Q 1/02; C12Q 1/18; G01N 19/00
See application file for complete search history.

(56) References Cited

U.S. PATENT DOCUMENTS 7,125,499 B2 * 10/2006 Ferguson ............. C09K 19/406
528/7
7,642,285 B2 1/2010 Blackwell et al.
(Continued)

OTHER PUBLICATIONS

Agarwal et al. (Apr. 2022) "Slippery Antifouling Polymer Coatings Fabricated Entirely from Biodegradable and Biocompatible Components," ACS Appl. Mater. Interfaces 2022, 14, 17940-17949.
(Continued)

*Primary Examiner* — James C Goloboy
(74) *Attorney, Agent, or Firm* — LEYDIG, VOIT & MAYER, LTD.

(57) ABSTRACT

The present invention provides liquid crystal (LC)-infused materials and methods for detecting compounds or impurities in liquid samples using such materials. These slippery materials comprise a lubricating liquid, preferably a thermotropic liquid crystal, and a solid substrate able to immobilize or host the lubricating liquid. The portion of the substrate coated by the lubricating fluid forms a slippery surface able to allow droplets of various materials to slide off the slippery surface in a manner dependent on the chemical composition of the droplet, which can be used to detect the presence of analytes, impurities and other molecules within the droplet.

21 Claims, 21 Drawing Sheets

(51) Int. Cl.
| | |
|---|---|
| *C10M 109/00* | (2006.01) |
| *C10M 171/00* | (2006.01) |
| *C10N 20/00* | (2006.01) |
| *C10N 40/00* | (2006.01) |
| *C10N 50/00* | (2006.01) |
| *C10N 50/08* | (2006.01) |
| *C12Q 1/02* | (2006.01) |
| *C12Q 1/18* | (2006.01) |
| *G01N 19/00* | (2006.01) |

(52) U.S. Cl.
CPC ........ *C10M 109/00* (2013.01); *C10M 171/00* (2013.01); *C10M 171/007* (2013.01); *C12Q 1/02* (2013.01); *C12Q 1/18* (2013.01); *G01N 19/00* (2013.01); *C10N 2020/079* (2020.05); *C10N 2040/00* (2013.01); *C10N 2050/023* (2020.05); *C10N 2050/08* (2013.01)

(56) References Cited

U.S. PATENT DOCUMENTS

| | | | |
|---|---|---|---|
| 7,883,720 | B2 | 2/2011 | Lynn et al. |
| 7,910,622 | B2 | 3/2011 | Blackwell et al. |
| 8,071,210 | B2 | 12/2011 | Lynn et al. |
| 8,097,277 | B2 | 1/2012 | Lynn et al. |
| 8,269,024 | B2 | 9/2012 | Blackwell et al. |
| 8,324,333 | B2 | 12/2012 | Liu et al. |
| 8,367,680 | B2 | 2/2013 | Blackwell et al. |
| 8,524,368 | B2 | 9/2013 | Lynn et al. |
| 8,624,063 | B2 | 1/2014 | Blackwell et al. |
| 8,716,422 | B2 | 5/2014 | Liu et al. |
| 8,815,943 | B2 | 8/2014 | Blackwell et al. |
| 10,487,217 | B2 | 11/2019 | Lynn et al. |
| 10,557,042 | B2 | 2/2020 | Lynn et al. |
| 10,557,044 | B2 | 2/2020 | Lynn et al. |
| 11,046,854 | B2 | 6/2021 | Lynn et al. |
| 2005/0027064 | A1 | 2/2005 | Lynn et al. |
| 2009/0170179 | A1 | 7/2009 | Lynn et al. |
| 2010/0048736 | A1 | 2/2010 | Liu et al. |
| 2011/0117138 | A1 | 5/2011 | Lynn et al. |
| 2011/0306142 | A1 | 12/2011 | Lynn et al. |
| 2012/0027833 | A1 | 2/2012 | Zilberman |
| 2012/0134926 | A1 | 5/2012 | Lynn et al. |
| 2013/0122055 | A1 | 5/2013 | Liu et al. |
| 2013/0129907 | A1 | 5/2013 | Popa et al. |
| 2014/0147627 | A1 | 5/2014 | Aizenberg et al. |
| 2014/0187666 | A1 | 7/2014 | Aizenberg et al. |
| 2014/0220617 | A1 | 8/2014 | Yung et al. |
| 2014/0328999 | A1 | 11/2014 | Aizenberg et al. |
| 2015/0152270 | A1 | 6/2015 | Aizenberg et al. |
| 2015/0173883 | A1 | 6/2015 | Ingber et al. |
| 2015/0175814 | A1 | 6/2015 | Aizenberg et al. |
| 2015/0196940 | A1 | 7/2015 | Aizenberg et al. |
| 2015/0209198 | A1 | 7/2015 | Aizenberg et al. |
| 2017/0022371 | A1* | 1/2017 | Lynn .................... C09D 5/1693 |
| 2020/0181419 | A1 | 6/2020 | Carter et al. |
| 2020/0299520 | A1 | 9/2020 | Lynn et al. |
| 2022/0030869 | A1 | 2/2022 | Lynn et al. |
| 2022/0032338 | A1 | 2/2022 | Lynn et al. |
| 2023/0303661 | A1 | 9/2023 | Connolly et al. |

OTHER PUBLICATIONS

Agarwal et al. (Jul. 2021) "Liquid Crystal-Infused Porous Polymer Surfaces: A "Slippery" Soft Material Platform for the Naked-Eye Detection and Discrimination of Amphiphilic Species," 28: 33652-33663.

Agarwal et al. (Nov. 2021) "Fabrication of Slippery Liquid-Infused Coatings in Flexible Narrow-Bore Tubing," ACS Applied Materials and Interfaces, 13: 55621-55632.

Agarwal et al. (Nov. 2021) "Slippery nanoemulsion-infused porous surfaces (SNIPS): anti-fouling coatings that can host and sustain the release of water-soluble agents," Chemical Communications, 57: 12691-12694.

Alino et al. (2011) "Liquid Crystal Droplets as a Hosting and Sensing Platform for Developing Immunoassays," Langmuir, 27 (19): 11784-11789.

Allen et al. (Mar. 14, 2014) "Targeting virulence: can we make evolution-proof drugs?" Nat. Rev. Microbiol. 12:300-308.

Alongi et al. (2013) "Layer by Layer coatings assembled through dipping, vertical or horizontal spray for cotton flame retardancy," Carbohydr Polym., 92:114-119.

An et al. (May 2018) "Covalent layer-by-layer films: chemistry, design, and multidisciplinary applications," Chem. Soc. Rev. 47: 5061-5098.

Anand et al. (2012) "Enhanced Condensation on Lubricant Impregnated Nanotextured Surfaces," ACS Nano, 6, 10122-10129.

Antipov et al. (2001) "Sustained Release Properties of Polyelectrolyte Multilayer Capsules," J. Phys. Chem. B. 105:2281-2284.

Appadoo et al. (Jul. 2016) "Controlling the Surface-Mediated Release of DNA Using 'Mixed Multilayers'", *Bioengineering & Translational Medicine*, 1(2):181-192.

Arciola et al. (2012) "Biofilm formation in *Staphylococcus* implant infections. A review of molecular mechanisms and implications for biofilm-resistant materials," Biomaterials. 33:5967-5982.

Badv et al. (2018) "Lubricant-Infused Surfaces with Built-In Functional Biomolecules Exhibit Simultaneous Repellency and Tunable Cell Adhesion," ACS Nano, 12 (11): 10890-10902.

Bae et al. (Dec. 18, 2013) "25th Anniversary Article: Scalable Multiscale Patterned Structures Inspired by Nature: The Role of Hierarchy," Adv. Mater. 26:675-700.

Bai et al. (2011) "Recent Advances in Colloidal and Interfacial Phenomena Involving Liquid Crystals," Langmuir. 27:5719-5738.

Banerjee et al. (2011) "Antifouling Coatings: Recent Developments in the Design of Surfaces That Prevent Fouling by Proteins, Bacteria, and Marine Organisms," Adv. Mater. 23:690-718.

Barthlott et al. (1997) "Purity of the sacred lotus, or escape from contamination in biological surfaces," Planta. 202:1-8.

Bassler et al. (2006) "Bacterially speaking," Cell. 125:237-246.

Bellanger et al. (Jan. 9, 2014) "Chemical and Physical Pathways for the Preparation of Superoleophobic Surfaces and Related Wetting Theories," Chem. Rev. 114:2694-2716.

Bergbreiter et al. (2009) "Covalent layer-by-layer assembly-an effective, forgiving way to construct functional robust ultrathin films and nanocomposites", Soft Matter, 5(1):23.

Bhardwaj et al. (2010) "Electrospinning: a fascinating fiber fabrication technique," Biotechnology Advances, 28(3): 325-347.

Bhargava et al. (1996) "Triclosan: applications and safety," Am. J. Infect. Control. 24:209-218.

Borges et al. (Aug. 2014) "Molecular Interactions Driving the Layer-by-Layer Assembly of Multilayers," *Chemical Reviews*, 114(18):8883.

Bortleson et al. (1972) "Recent sedimentary history of Lake Mendota, Wis.," Environ. Sci. Technol. 6:799-808.

Boudou et al. (2010) "Multiple functionalities of polyelectrolyte multilayer films: new biomedical applications," Adv. Mater. 22:441-467.

Brake et al. (2002) "An Experimental System for Imaging the Reversible Adsorption of Amphiphiles at Aqueous-Liquid Crystal Interfaces," Langmuir, 18(16): 6101-6109.

Brake et al. (2003) "Biomolecular interactions at phospholipid-decorated surfaces of liquid crystals," Science. 302:2094-2097.

Brake et al. (2003) "Effect of Surfactant Structure on the Orientation of Liquid Crystals at Aqueous-Liquid Crystal Interfaces," Langmuir, 19 (16): 6436-6442.

Breitbach et al. (2011) "Surface-mediated release of a synthetic small-molecule modulator of bacterial quorum sensing: Gradual release enhances activity," Chem. Comm. 47:370-372.

Brock et al. (1984) "Significance of algal excretory products for growth of epilimnetic bacteria," Appl. Environ. Microbiol. 47:731-734.

Broderick et al. (2011) "Fabrication and Selective Functionalization of Amine-Reactive Polymer Multilayers on Topographically Patterned Microwell Cell Culture Arrays", *Biomacromolecules*, 12 (6):1998-2007.

(56) References Cited

OTHER PUBLICATIONS

Broderick et al. (2012) "Covalent Layer-by-Layer Assembly of Water-Permeable and Water-Impermeable Polymer Multilayers on Highly Water-Soluble and Water-Sensitive Substrates," Chem. Mater. 24:1786-1795.
Broderick et al. (2012) "In situ Synthesis of Oligonucleotide Arrays on Surfaces Coated with Crosslinked Polymer Multilayers," Chem. Mater. 24:938-945.
Broderick et al. (2012) in Functional Polymers by Post-Polymerization Modification: Concepts, Practical Guidelines, and Applications, Theato and Klok Eds., Wiley-VCH; pp. 371-406.
Broderick et al. (2013) "Fabrication of Oligonucleotide and Protein Arrays on Rigid and Flexible Substrates Coated with Reactive Polymer Multilayers", *ACS Applied Materials & Interfaces*, 5(2):351.
Broderick et al. (Jan. 20, 2013) "Surface-mediated release of a small-molecule modulator of bacterial biofilm formation: A non-bactericidal approach to inhibiting biofilm formation in Pseudomonas aeruginosa," Adv. Healthcare Mater. 2:993-1000.
Broderick et al. (Jun. 28, 2014) "Surface coatings that promote rapid release of peptide-based AgrC inhibitors for attenuation of quorum sensing in *Staphylococcus aureus*," Adv. Healthcare Mater. 3:97-105.
Bruchmann et al. (2017) "Patterned SLIPS for the Formation of Arrays of Biofilm Microclusters with Defined Geometries," Advanced Healthcare Materials, 6 (1): 1601082.
Buck et al. (2007) "Layer-by-layer assembly of reactive ultrathin films mediated by click-type reactions of poly(2-alkenyl azlactone)s," Adv. Mater. 19:3951-3955.
Buck et al. (2009) "Chemical Modification of Reactive Multilayered Films Fabricated from Poly(2-alkenyl azlactone)s: Design of Surfaces that Prevent or Promote Mammalian Cell Adhesion and Bacterial Biofilm Growth," Biomacromolecules. 10:1564-1574.
Buck et al. (2010) "Free-Standing and Reactive Thin Films Fabricated by Covalent Layer-by-Layer Assembly and Subsequent Lift-Off of Azlactone-Containing Polymer Multilayers," Langmuir 26(20): 16134-16140.
Buck et al. (2010) "Functionalization of Fibers Using Azlactone-Containing Polymers: Layer-by-Layer Fabrication of Reactive Thin Films on the Surfaces of Hair and Cellulose-Based Materials," ACS Appl. Mater. Interfaces. 2:1421-1429.
Buck et al. (2010) "Superhydrophobic thin films fabricated by reactive layer-by-layer assembly of azlactone-functionalized polymers," Chem. Mater. 22:6319-6327.
Buck et al. (2010) "Reactive Layer-by-Layer Assembly of Suspended Thin Films and Semipermeable Membranes at Interfaces Created Between Aqueous and Organic Phases," *Advanced Materials*, 22(9):994.
Buck et al. (Oct. 12, 2011) "Azlactone-functionalized polymers as reactive platforms for the design of advanced materials: Progress in the last ten years," Polym. Chem. 3:66-80.
Busscher et al. (2012) "Biomaterial-associated infection: Locating the finish line in the race for the surface," Sci. Transl. Med. 4:153rv110.
Cadwell et al. (2006) "Infrared Spectroscopy of Competitive Interactions between Liquid Crystals, Metal Salts, and Dimethyl Methylphosphonate at Surfaces," The Journal of Physical Chemistry B, 110: 26081-26088.
Cai et al. (Feb. 2014) "Filefish-Inspired Surface Design for Anisotropic Underwater Oleophobicity," Adv. Funct. Mater. 24(6):809-816.
Camilli et al. (2006) "Bacterial small-molecule signaling pathways," Science. 311:1113-1116.
Campoccia et al. (Aug. 15, 2013) "A review of the biomaterials technologies for infection-resistant surfaces," Biomaterials. 34:8533-8554.
Carlton et al. (2013) "Chemical and biological sensing using liquid crystals," Liq Cryst Rev, 1 (1): 29-51.
Carlton et al. (2014) "Surfactant-Induced Ordering and Wetting Transitions of Droplets of Thermotropic Liquid Crystals "Caged" Inside Partially Filled Polymeric Capsules," Langmuir, 30 (49): 14944-14953.
Carlton et al. (Jan. 2012) "Influence of Simple Electrolytes on the Orientational Ordering of Thermotropic Liquid Crystals at Aqueous Interfaces," Langmuir, 28 (1): 31-36.
Carlton et al. (Sep. 2012) "Influence of Specific Anions on the Orientational Ordering of Thermotropic Liquid Crystals at Aqueous Interfaces," Langmuir, 28 (35): 12796-12805.
Carson et al. (2016) "Tunable Release of Multiclass Anti-HIV Drugs that are Water-Soluble and Loaded at High Drug Content in Polyester Blended Electrospun Fibers," Pharm. Res. 33, 125-136.
Carter et al. (2015) "Synthetic Mimics of Bacterial Lipid A Trigger Optical Transitions in Liquid Crystal Microdroplets at Ultralow Picogram-per-Milliliter Concentrations," Langmuir, 31 (47): 12850-12855.
Carter et al. (Jul. 2016) "Synthesis and Characterization of Backbone Degradable Azlactone-Functionalized Polymers," *Macromolecules*, 49(15):5514.
Carter et al. (Jul. 2020) "Influence of Side Chain Hydrolysis on the Evolution of Nanoscale Roughness and Porosity in Amine-Reactive Polymer Multilayers," Chem. Mater., 32: 6935-6946.
Carter et al. (Jun. 2016) "Covalently Crosslinked and Physically Stable Polymer Coatings with Chemically Labile and Dynamic Surface Features Fabricated by Treatment of Azlactone-Containing Multilayers with Alcohol-, Thiol-, and Hydrazine-Based Nucleophiles," *Chemistry of Materials*, 28(14):5063.
Cassie et al. (1944) "Wettability of porous surfaces," Trans. Faraday Soc. 40:546-551.
Chang et al. (2014) "Oligopeptide-decorated liquid crystal droplets for detecting proteases," Chemical Communications, 50 (81): 12162-12165.
Chapman et al. (2000) "Surveying for Surfaces that Resist the Adsorption of Proteins," J. Am. Chem. Soc. 122:8303-8304.
Charlton et al. (2000) "A Noveland Sensitive Method for the Quantification of N-3-Oxoacyl Homoserine Lactone Using GasChromatography—Mass Spectrometry: Application to a Model Bacterial Biofilm," Environ.Microbiol, 2, 530-541.
Che et al. (2017) "Lubricant-Infused Anisotropic Porous Surface Design of Reduced Graphene Oxide Toward Electrically Driven Smart Control of Conductive Droplets' Motion," Adv Funct Mater, 27 (22): 1606199.
Cheung et al. (2014) "Phenol-soluble modulins—critical determinants of staphylococcal virulence," FEMS Microbiol. Rev., 38 (4), 698-719.
Chong et al. (2017) "Microbial Production of Rhamnolipids: Opportunities, Challenges and Strategies," Microb. Cell Fact, 16, 137.
Chou et al. (2015) "Current strategies for sustaining drug release from electrospun nanofibers," J. Controlled Release, 220, 584-591.
Chu et al. (Jan. 31, 2014) "Superamphiphobic surfaces," Chem. Soc. Rev. 43:2784-2798.
Chung et al. (2002) "Methods of Loading and Releasing Low Molecular Weight Cationic Molecules in Weak Polyelectrolyte Multilayer Films," Langmuir. 18:1176-1183.
Cipitria et al. (2011) "Design, fabrication and characterization of PCL electrospun scaffolds—a review," J. Mater. Chem. 21, 9419-9453.
Clatworthy et al. (2007) "Targeting virulence: a new paradigm for antimicrobial therapy," Nat. Chem. Biol. 3:541-548.
Costerton et al. (1999) "Bacterial biofilms: A common cause of persistent infections," Science. 284:1318-1322.
Daniel et al. (2017) "Oleoplaning droplets on lubricated surfaces," Nature Physics, 13 (10): 1020-1025.
Daniel et al. (Jun. 2013) "Lubricant-infused micro/nano-structured surfaces with tunable dynamic omniphobicity at high temperatures," Appl. Phys. Lett. 102:231603.
Daristotle et al. (Dec. 2016) "A Review of the Fundamental Principles and Applications of Solution Blow Spinning," ACS Appl. Mater. Interfaces, 8(51): 34951-34963.
De Kievit et al. (2001) "Quorum-sensing genes in Pseudomonas aeruginosa biofilms: their role and expression patterns," Appl. Environ. Microbiol. 67:1865-1873.

(56) References Cited

OTHER PUBLICATIONS

De Mul et al. (1994) "Multilayer Formation in Thin Films of Thermotropic Liquid Crystals at the Air-Water Interface," Langmuir, 10 (7): 2311-2316.
Decher (1997) "Fuzzy nanoassemblies Toward layered polymeric multicomposites", *Science*, 277(5330): 1232.
Deng et al. (2010) "Laundering Durability of Superhydrophobic Cotton Fabric," Adv. Mater. 22:5473-5477.
Deng et al. (2011) "Transparent, Thermally Stable and Mechanically Robust Superhydrophobic Surfaces Made from Porous Silica Capsules," Adv. Mater. 23:2962-2965.
Deng et al. (2012) "Candle soot as a template for a transparent robust superamphiphobic coating," Science. 335:67-70.
Dierendonck et al. (Feb. 2014) "Just spray it—LbL assembly enters a new age," Soft Matter, 10: 804-807.
Dou et al. (2014) "Anti-icing Coating with an Aqueous Lubricating Layer," ACS Applied Materials & Interfaces, 6 (10): 6998-7003.
Eibergen et al. (Oct. 13, 2015) "Potent and selective modulation of the RhIR quorum sensing receptor by using non-native ligands: An emerging target for virulence control in Pseudomonas aeruginosa," ChemBioChem. 16(16):2348-2356.
Epstein et al. (2012) "Liquid-infused structured surfaces with exceptional anti-biofouling performance," Proc. Natl. Acad. Sci. USA. 109:13182-13187.
Feng et al. (2002) "Super-Hydrophobic Surfaces: From Natural to Artificial," Adv. Mater. 14:1857-1860.
Feng et al. (2006) "Design and Creation of Superwetting/Antiwetting Surfaces," Adv. Mater. 18: 3063-3078.
Fredin et al. (2013) Nanoimprinted Thin Films of Reactive, Azlactone-Containing Polymers Combining Methods for the Topographic Patterning of Cell Substrates with Opportunities for Facile Post-Fabrication Chemical Functionalization, *Biomacromolecules*, 10(4):994-1003.
Frei et al. (2012) "2-Aminobenzimidazole derivatives strongly inhibit and disperse Pseudomonas aeruginosa biofilms," Angew. Chem. Int. Ed. 51:5226-5229.
Fuqua et al. (2002) "Listening in on Bacteria: Acyl-Homoserine Lactone Signalling," Nat. Rev. Mol. Cell Biol, 3, 685-695.
Gao et al. (2004) "Biophysics: Water-repellent legs of water striders," Nature. 432:36.
Gao et al. (2018) "Droplets Manipulated on Photothermal Organogel Surfaces," Adv Funct Mater, 28 (35): 1803072.
Gao et al. (Oct. 2021) "Recent progress and challenges in solution blow spinning," Materials Horizons, 8, 426-446.
Gardner et al. (2011) Reactive Polyanions Based on Poly(4,4-dimethyl-2-vinyl-2-oxazoline-5-one-co-methacrylic acid). *Macromolecules*, 44(18):7115.
Gennip et al. (2012) "Interactions between Polymorphonuclear Leukocytes and Pseudomonas aeruginosa Biofilms on Silicone Implants In Vivo," Infection and Immunity. 80 (8): 2601-2607.
Genzer et al. (2000) "Creating long-lived superhydrophobic polymer surfaces through mechanically assembled monolayers," Science. 290:2130-2133.
Geske et al. (2008) "Comparative analyses of N-acylated homoserine Lactones reveal unique structural features that dictate their ability to activate or inhibit quorum sensing," ChemBioChem. 9:389-400.
Geske et al. (2008) "Evaluation of a focused library of N-aryl L-homoserine lactones reveals a new set of potent quorum sensing modulators," Bioorg. Med. Chem. Lett. 18:5978-5981.
Gilbert et al. (2013) "Depth-profiling X-ray photoelectron spectroscopy (XPS) analysis of interlayer diffusion in polyelectrolyte multilayers," *Proceedings of the National Academy of Sciences*, 110(17):6651.
Glavan et al. (Jul. 26, 2013) "Omniphobic 'RF Paper' Produced by Silanization of Paper with Fluoroalkyltrichlorosilanes," Adv. Funct. Mater. 24:60-70.
Goudie et al. (2017) "Liquid-infused nitric oxidereleasing (LINORel) silicone for decreased fouling, thrombosis, and infection of medical devices," Sci. Rep. 7: 13623.
Grinthal et al. (Oct. 14, 2013) "Mobile interfaces: Liquids as a perfect structural material for multifunctional, antifouling surfaces," Chem. Mater. 26:698-708.
Guo et al. (2016) "Anisotropic Slippery Surfaces: Electric-Driven Smart Control of a Drop's Slide," Advanced Materials, 28 (32): 6999-7007.
Guo et al. (Nov. 2015) "Covalent Immobilization of Caged Liquid Crystal Microdroplets on Surfaces," *ACS Applied Materials & Interfaces*, 7(48):26892.
Gupta et al. (2009) "Characterization of Adsorbate-Induced Ordering Transitions of Liquid Crystals within Monodisperse Droplets," Langmuir, 25 (16): 9016-9024.
Gupta et al. (2009) "Principles for Manipulation of the Lateral Organization of Aqueous-Soluble Surface-Active Molecules at the Liquid Crystal-Aqueous Interface," Langmuir, 25 (4): 2026-2033.
Hammond (1999) "Recent explorations in electrostatic multilayer thin film assembly," Curr. Opin. Colloid Interface Sci. 4: 430-442.
Hammond (2004) "Form and Function in Multilayer Assembly New Applications at the Nanoscale," *Advanced Materials*, 16(15):1271.
Hammond (2011) "P. T. Engineering materials layer-by-layer: Challenges and opportunities in multilayer assembly," *AIChE Journal*, 57(11):2928.
Han et al. (2009) "Superhydrophobic and Oleophobic Fibers by Coaxial Electrospinning," Langmuir, 25, 9454-9462.
Heilmann et al. (1984) "Chemistry of alkenyl azlactones. I. Radiation-sensitive materials derived from azlactone-containing copolymers," J. Polym. Sci. Part A. 22(5):1179-1186.
Heilmann et al. (1998) "The chemistry of 2-alkenyl-5(4H)-oxazolones. VIII acid-catalyzed reaction with alcohols," Tetrahedron. 54(40):12151-12160.
Heilmann et al. (2001) "Chemistry and technology of 2-alkenyl azlactones," J. Polymer Sci. Part A. 39(21):3655-3677.
Heilmann et al. (2003) "The Chemistry of 2-Alkenyl-5(4H)-Oxazolones. IX. Acid-Catalyzed Oligomerization," J. of Macromolecular Science, Part A, 40(8):755.
Held et al. (2012) "Sequence-verified two-allele transposon mutant library for Pseudomonas aeruginosa PAO1," J. Bacteriol., 194 (23), 6387-9.
Holden et al. (Oct. 2015) "Photolithographic Synthesis of High-Density DNA and RNA Arrays on Flexible, Transparent, and Easily Subdivided Plastic Substrates", *Analytical Chemistry*, 87(22):11420.
Holloway (1955) "Genetic recombination in Pseudomonas aeruginosa," J. Gen. Microbiol. 13:572-581.
Homeyer et al. (2019) "Liquid-Infused Nitric-Oxide-Releasing Silicone Foley Urinary Catheters for Prevention of Catheter-Associated Urinary Tract Infections," ACS Biomater. Sci. Eng. 5: 2021-2029.
Howell et al. (Feb. 4, 2015) "Stability of Surface-Immobilized Lubricant Interfaces under Flow," Chem. Mater. 27:1792-1800.
Howell et al. (Jul. 23, 2014) "Self-Replenishing Vascularized Fouling-Release Surfaces," ACS Appl. Mater. Inter. 6:13299-13307.
Hsu et al. (2000) "Adsorption Kinetics of C12E4 at the Air-Water Interface: Adsorption onto a Fresh Interface," Langmuir, 16 (7): 3187-3194.
Huang et al. (2011) "Controllable Underwater Oil-Adhesion-Interface Films Assembled from Nonspherical Particles," Adv. Funct. Mater. 21:4436-4441.
Huang et al. (2017) "A Switchable Cross-Species Liquid Repellent Surface," Advanced Materials, 29 (8): 1604641.
Huang et al. (2019) "Patterned Slippery Surface through Dynamically Controlling Surface Structures for Droplet Microarray," Chemistry of Materials, 31 (3): 834-841.
Huang et al. (Sep. 4, 2013) "Omniphobic slippery coatings based on lubricant-infused porous polyelectrolyte multilayers," ACS Macro Lett. 2:826-829.
Ionov et al. (2012) "Self-healing superhydrophobic materials," Phys. Chem. Chem. Phys. 14:10497-10502.
Izquierdo et al. (2005) "Dipping versus Spraying: Exploring the Deposition Conditions for Speeding Up Layer-by-Layer Assembly," Langmuir, 21(16), 7558-7567.
Jacobs et al. (2003) "Comprehensive transposon mutant library of Pseudomonas aeruginosa," Proc Natl Acad Sci USA, 100 (24), 14339-44.

(56) References Cited

OTHER PUBLICATIONS

Jewell et al. (2008) "Multilayered polyelectrolyte assemblies as platforms for the delivery of DNA and other nucleic acid-based therapeutics," Adv. Drug Deliver. Rev. 60:979-999.
Ji et al. (2006) "Fabrication of a Superhydrophobic Surface from the Amplified Exponential Growth of a Multilayer," Adv. Mater. 18:1441-1444.
Jin et al. (2011) "Underwater Oil Capture by a Three-Dimensional Network Architectured Organosilane Surface," Adv. Mater. 23:2861-2864.
Jisr et al. (2005) "Hydrophobic and Ultrahydrophobic Multilayer Thin Films from Perfluorinated Polyelectrolytes," Angew. Chem. Int. Ed. 44:782-785.
Johnston et al. (2007) "Assembling DNA into Advanced Materials: From Nanostructured Films to Biosensing and Delivery Systems," Adv. Mater. 19 :3727-3730.
Jones et al. (2000) "Triclosan: A review of effectiveness and safety in health care settings," Am. J. Infect. Control. 28:184-196.
Jung et al. (2009) "Wetting Behavior of Water and Oil Droplets in Three-Phase Interfaces for Hydrophobicity/philicity and Oleophobicity/philicity," Langmuir. 25:14165-14173.
Kaplan et al. (2014) "Imparting Superhydrophobicity to Biodegradable Poly(lactide-co-glycolide) Electrospun Meshes," Biomacromolecules, 15, 2548-2554.
Khalil et al. (2014) "Active surfaces: Ferrofluid-impregnated surfaces for active manipulation of droplets ," Applied Physics Letters, 105 (4): 041604.
Kharlampieva et al. (2004) "Release of a Dye from Hydrogen-Bonded and Electrostatically Assembled Polymer Films Triggered by Adsorption of a Polyelectrolyte," Langmuir. 20:9677-9685.
Kharlampieva et al. (2009) "Layer-by-Layer Hydrogen-Bonded Polymer Films: From Fundamentals to Applications," Adv. Mater. 21: 3053-3065.
Kim et al. (2008) "Hydrogen-Bonding Layer-by-Layer-Assembled Biodegradable Polymeric Micelles as Drug Delivery Vehicles from Surfaces," ACS Nano. 2:386-392.
Kim et al. (2012) "Liquid-Infused Nanostructured Surfaces with Extreme Anti-Ice and Anti-Frost Performance," ACS Nano. 6:6569-6577.
Kim et al. (2013) "Hierarchical or Not? Effect of the Length Scale and Hierarchy of the Surface Roughness on Omniphobicity of Lubricant-Infused Substrates," Nano Lett. 13:1793-1799.
Kinsinger et al. (2008) "Dynamic Ordering Transitions of Liquid Crystals Driven by Interfacial Complexes Formed between Polyanions and Amphiphilic Polyamines", *Langmuir*, 24(23):13231.
Kojic et al. (2004) "Candida infections of medical devices," Clin. Microbiol. Rev. 17:255-267.
Kool et al. (Nov. 12, 2013) "Fast Hydrazone Reactants: Electronic and Acid/Base Effects Strongly Influence Rate at Biological pH," Journal of the American Chemical Society. 135(47):17663-17666.
Kota et al. (2012) "Hygro-responsive membranes for effective oil-water separation," Nat. Commun. 3:1025.
Kratochvil et al. (Aug. 26, 2015) "Nanoporous superhydrophobic coatings that promote the extended release of water-labile quorum sensing inhibitors and enable long-term modulation of quorum sensing in *Staphylococcus aureus*," ACS Biomater. Sci. Eng. 1:1039-1049.
Kratochvil et al. (May 2016) "Slippery Liquid-Infused Porous Surfaces that Prevent Bacterial Surface Fouling and Inhibit Virulence Phenotypes in Surrounding Planktonic Cells", *ACS Infectious Diseases*, 2(7): 509.
Kratochvil et al., (2017) "Amine-Reactive Azlactone-Containing Nanofibers For the Immobilization and Patterning of New Functionality on Nanofiber-Based Scaffolds", *ACS Applied Materials and Interfaces*, 9:10243-10253.
Krogman et al. (2009) "Spraying asymmetry into functional membranes layer-by-layer," Nat. Mater. 8: 512-518.
Kyung et al. (2011) "Nanoscale Texture Control of Polyelectrolyte Multilayer Using Spray Layer-by-Layer Method," Japanese Journal of Applied Physics, 50: 025602.
Lafuma et al. (2011) "Slippery pre-suffused surfaces," EPL (Europhysics Letters) 96, 56001.
Lee et al. (2014) "Hydrophobicity and Helicity Regulate the Antifungal Activity of 14-Helical β-Peptides," ACS Chem. Biol. 9(7): 1613-1621.
Lefort et al. (2010) "Spray-On Organic/Inorganic Films: A General Method for the Formation of Functional Nano-to Microscale Coatings," Angew. Chem. Int. Ed., 49: 10110-10113.
Lefort et al. (2011) "Simultaneous Spray Coating of Interacting Species: General Rules Governing the Poly(styrene sulfonate)/Poly(allylamine) System," Langmuir, 27: 4653-4660.
Lefort et al. (2013) "Nanosized Films Based on Multicharged Small Molecules and Oppositely Charged Polyelectrolytes Obtained by Simultaneous Spray Coating of Interacting Species," Langmuir, 29: 14536-14544.
Lepine et al. (2002) "Liquid Chromatographic/Mass Spectrometric Detectionof the 3-(3-Hydroxyalkanoyloxy) Alkanoic Acid Precursors of Rhamnolipids in Pseudomonasaeruginosa Cultures," J. Mass Spectrom, 37, 41-46.
Leslie et al. (Oct. 12, 2014) "A bioinspired omniphobic surface coating on medical devices prevents thrombosis and biofouling," Nat. Biotechnol. 32:1134-1140.
Levkin et al. (2009) "Porous Polymer Coatings: a Versatile Approach to Superhydrophobic Surfaces," Adv. Funct. Mater. 19:1993-1998.
Li et al. (2010) "Bioinspired self-healing superhydrophobic coatings," Angew. Chem. Int. Ed. 49:6129-6133.
Li et al. (2012) "Layer-by-layer assembly for rapid fabrication of thick polymeric films," Chem. Soc. Rev., 41: 5998-6009.
Li et al. (2012) "Printable Superhydrophilic-Superhydrophobic Micropatterns Based on Supported Lipid Layers," Langmuir. 28:8286-8291.
Li et al. (Dec. 18, 2014) "Reactive superhydrophobic surface and its photoinduced disulfide-ene and thiol-ene (bio)functionalization," Nano Lett. 15:675-681.
Li et al. (Jul. 5, 2013) "Hydrophobic liquid-infused porous polymer surfaces for antibacterial applications," ACS Appl. Mater. Interfaces 5:6704-6711.
Lin et al. (2010) "Bio-inspired hierarchical macromolecule-nanoclay hydrogels for robust underwater superoleophobicity," Adv. Mater. 22:4826-4830.
Lin et al. (2011) "Endotoxin-induced structural transformations in liquid crystalline droplets," Science. 332:1297-1300.
Lipinski (2000) "Drug-like properties and the causes of poor solubility and poor permeability," Journal of Pharmacological and Toxicological Methods. 44:235-249.
Liu et al. (2008) "Ultrathin Multilayered Films that Promote the Release of Two DNA Constructs with Separate and Distinct Release Profiles," Adv. Mater. 20:4148-4153.
Liu et al. (2009) "Bioinspired Design of a Superoleophobic and Low Adhesive Water/Solid Interface," Adv. Mater. 21:665-669.
Liu et al. (2010) "Recent developments in bio-inspired special wettability," Chem. Soc. Rev. 39:3240-3255.
Liu et al. (2012) "Bioinspired oil strider floating at the oil/water interface supported by huge superoleophobic force," ACS Nano. 6:5614-5620.
Liu et al. (2012) "Bio-Inspired Self-Cleaning Surfaces," Ann. Rev. Mater. Res. 42:231-263.
Liu et al. (2012) "Clam's shell inspired high-energy inorganic coatings with underwater low adhesive superoleophobicity," Adv. Mater. 24:3401-3405.
Liu et al. (2012) "Complementary effects of nanosilver and superhydrophobic coatings on the prevention of marine bacterial adhesion," ACS Appl. Mater. Interfaces. 4:4683-4690.
Liu et al. (2017) "Evaluation of Electrospun Fibrous Mats Targeted for Use as Flow Battery Electrodes," J. Electrochem. Soc., 164, A2038-A2048.
Liu et al. (Jun. 17, 2013) "Organogel-based thin films for self-cleaning on various surfaces," Adv. Mater. 25:4477-4481.
Lockwood et al. (2005) "Influence of Surfactant Tail Branching and Organization on the Orientation of Liquid Crystals at Aqueous-Liquid Crystal Interfaces," Langmuir, 21 (15): 6805-6814.

(56) References Cited

OTHER PUBLICATIONS

Lockwood et al. (2008) "Self-assembly of amphiphiles, polymers and proteins at interfaces between thermotropic liquid crystals and aqueous phases," Surface Science Reports, 63: 255-293.
Luong-Van et al. (2006) "Controlled release of heparin from poly(ϵ-caprolactone) electrospun fibers," Biomaterials, 27, 2042-2050.
Lynn (2007) "Peeling Back the Layers: Controlled Erosion and Triggered Disassembly of Multilayered Polyelectrolyte Thin Films," Adv. Mater. 19:4118-4130.
Lyon et al. (2000) "Rational design of a global inhibitor of the virulence response in *Staphylococcus aureus*, based in part on localization of the site of inhibiton to the receptor-histidine kinase," AgrC. Proc Natl Acad Sci USA, 97 (24), 13330-13335.
Ma et al. (2005) "Superhydrophobic Fabrics Produced by Electrospinning and Chemical Vapor Deposition," Macromolecules, 38, 9742-9748.
Ma et al. (2019) "Facile fabrication of biomimetic liquid-infused slippery surface on carbon steel and its self-cleaning, anti-corrosion, anti-frosting and tribological properties," Colloids and Surfaces A: Physicochemical and Engineering Aspects, 577: 17-26.
Ma et al. (Feb. 11, 2014) "Substrate-Independent Underwater Superoleophobic Surfaces Inspired by Fish-Skin and Mussel-Adhesives," Adv. Mater. Interfaces. 1:1300092.
Macdonald et al. (2008) "Release of a model protein from biodegradable self assembled films for surface delivery applications," J. Control. Release. 131:228-234.
Manabe et al. (2015) "Biocompatible Slippery Fluid-Infused Films Composed of Chitosan and Alginate via Layer-by-Layer Self-Assembly and Their Antithrombogenicity," ACS Appl. Mater. Interfaces, 7, 4763-4771.
Manna et al. (2008) "Encapsulation of Uncharged Water-Insoluble Organic Substance in Polymeric Membrane Capsules via Layer-by-Layer Approach," J. Phys. Chem. B. 112:13258-13262.
Manna et al. (2012) "Chemical Patterning and Physical Refinement of Reactive Superhydrophobic Surfaces," Adv. Mater. 24:4291-4295.
Manna et al. (2013) "Liquid Crystal Chemical Sensors That Cells Can Wear", *Angewandte Chemie International Edition*, 52(52):14011.
Manna et al. (2013) "Patterning and Impregnation of Superhydrophobic Surfaces Using Aqueous Solutions," *ACS Applied Materials & Interfaces*, 5(16):7731.
Manna et al. (2013) "'Shrink-to-Fit' Superhydrophobicity Thermally-Induced Microscale Wrinkling of Thin Hydrophobic Multilayers Fabricated on Flexible Shrink-Wrap Substrates," *Advanced Materials*, 25(22):3085.
Manna et al. (Apr. 27, 2016) "Slippery liquid-infused porous surfaces that prevent microbial surface fouling and kill non-adherent pathogens in surrounding media: A controlled release approach," Advanced Functional Materials. 26(21):3599-3611.
Manna et al. (Apr. 8, 2015) "Fabrication of liquid-infused surfaces using reactive polymer multilayers: Principles for manipulating the behaviors and mobilities of aqueous fluids on slippery liquid interfaces," Adv. Mater. 27:3007-3012.
Manna et al. (Aug. 13, 2013) "Restoration of Superhydrophobicity in Crushed Polymer Films by Treatment with Water: Self-Healing and Recovery of Damaged Topographic Features Aided by an Unlikely Source," Adv. Mater. 25:5104-5108.
Manna et al. (Aug. 25, 2013) "Superhydrophobic polymer multilayers that promote the extended, long-term release of embedded water-soluble agents," Adv. Mater. 25:6405-6409.
Manna et al. (Feb. 4, 2015) "Synthetic Surfaces with Robust and Tunable Underwater Superoleophobicity," Adv. Funct. Mater. 25:1672-1681.
Martinez et al. (2011) "The intrinsic interfacial structure of ionic surfactant monolayers at water-oil and water-vapour interfaces," Proceedings of the Royal Society A: Mathematical, Physical and Engineering Sciences, 467 (2131): 1939-1958.
Mattmann et al. (2011) "Potent and selective synthetic modulators of a quorum sensing repressor in Pseudomonas aeruginosa identified from second-generation libraries of N-acylated L-homoserine lactones," ChemBioChem. 12:942-949.
Mavor et al. (2005) "Systemic fungal infections caused by *Candida* species: epidemiology, infection process and virulence attributes," Curr. Drug Targ. 6:863-874.
Medeiros et al. (2009) "Solution blow spinning: A new method to produce micro- and nanofibers from polymer solutions," Journal of Applied Polymer Science, 113: 2322-2330.
Mellbye et al. (Dec. 27, 2013) "Physiological framework for the regulation of quorum sensing-dependent public goods in Pseudomonas aeruginosa," J. Bacteriol. 196:1155-1164.
Menger et al. (1974) "Interfacial and Micellar Properties of Bolaform Electrolytes," The Journal of Physical Chemistry, 78 (14): 1387-1390.
Miller et al. (Mar. 2013) "Instructional Review: An Introduction to Optical Methods for Characterizing Liquid Crystals at Interfaces," Langmuir, 29 (10): 3154-3169.
Miller et al. (Nov. 2013) "Rapid Analysis of the Internal Configurations of Droplets of Liquid Crystal Using Flow Cytometry," Analytical Chemistry, 85 (21), 10296-10303.
Moore et al. (Oct. 22, 2015) "A comparative analysis of synthetic quorum sensing modulators in Pseudomonas aeruginosa: New insights into mechanism, active efflux susceptibility, phenotypic response, and next-generation ligand design," J. Am. Chem. Soc. 137:14626-14639.
Muh et al. (2006) "Novel Pseudomonas aeruginosa quorum-sensing inhibitors identified in an ultra-high-throughput screen," Antimicrob. Agents Chemother. 50:3674-3679.
Mulhearn et al. (2012) "Facilitated transport enhances spray layer-by-layer assembly of oppositely charged nanoparticles," Soft Matter, 8: 10419-10427.
Ng et al. (2009) "Bacterial quorum-sensing network architectures," Annu. Rev. Genet. 43:197-222.
Nicolle (2005) "Catheter-related urinary tract infection," Drug. Aging. 22:627-639.
Nishimoto et al. (Oct. 23, 2013) "Bioinspired self-cleaning surfaces with superhydrophobicity, superoleophobicity, and superhydrophilicity," RSC Adv. 3:671-690.
Nolte et al. (2007) "Thin Film Thickness Gradients and Spatial Patterning via Salt Etching of Polyelectrolyte Multilayers", *Macromolecules*, 40(15):5479.
Nolte et al. (2008) "Effect of Relative Humidity on the Young's Modulus of Polyelectrolyte Multilayer Films and Related Nonionic Polymers", *Macromolecules*, 41(15):5793.
Novick (1967) "Properties of a Cryptic High-Frequency Transducing Phage in *Staphylococcus aureus*," Virology, 33, 155-166.
Novick et al. (1993) "Synthesis of staphylococcal virulence factors is controlled by a regulatory RNA molecule," The EMBO journal, 12, 3967-3975.
O'Reilly et al. (Nov. 2, 2015) "Structure-Based Design and Biological Evaluation of Triphenyl Scaffold-Based Hybrid Compounds as Hydrolytically Stable Modulators of a LuxR-Type Quorum Sensing Receptor," ACS Infect. Dis. 2:32-38.
O'Loughlin et al. (Oct. 29, 2013) "A quorum-sensing inhibitor blocks Pseudomonas aeruginosa virulence and biofilm formation," Proc. Natl. Acad. Sci. USA. 110:17981-17986.
Orner et al. (2004) "Arrays for the Combinatorial Exploration of Cell Adhesion," J. Am. Chem. Soc. 126:10808-10809.
Ortiz et al. (Jun. 2020) "Liquid Crystal Emulsions That Intercept and Report on Bacterial Quorum Sensing," ACS Applied Materials & Interfaces, 12 (26): 29056-29065.
Park et al. (2014) "Detection of mRNA from *Escherichia coli* in drinking water on nanostructured polymeric surfaces using liquid crystals," Colloid and Polymer Science, 292 (5): 1163-1169.
Parker et al. (2001) "Water capture by a desert beetle," Nature. 414:33-34.
Passerini et al. (1992) "Biofilms on indwelling vascular catheters," Crit. Care Med. 20:665-673.
Peeters et al. (2008) "Comparison of multiple methods for quantification of microbial biofilms grown in microtiter plates," J. Microbiol. Meth. 72:157-165.

(56) References Cited

OTHER PUBLICATIONS

Peppou-Chapman et al. (May 2020) "Life and death of liquid-infused surfaces: a review on the choice, analysis and fate of the infused liquid layer," Chem. Soc. Rev., 49: 3688-3715.
Pereira et al. (May 20, 2014) "Brønsted acid catalyzed azlactone ring opening by nucleophiles," Tetrahedron. 70(20):3271-3275.
Peschel et al. (2013) "Phenol-Soluble Modulins and Staphylococcal Infection," Nat. Rev.Microbiol, 11, 667-673.
Pham et al. (2006) "Electrospinning of polymeric nanofibers for tissue engineering applications: a review," Tissue Eng. 12, 1197-1211.
Popov et al. (2017) "Thermotropic liquid crystal films for biosensors and beyond," Journal of Materials Chemistry B, 5 (26): 5061-5078.
Porcel et al. (2005) "Ultrathin Coatings and (Poly(glutamic acid)/Polyallylamine) Films Deposited by Continuous and Simultaneous Spraying," Langmuir, 21: 800-802.
Porter et al. (2005) "Use of Parallel Synthesis To Probe Structure-Activity Relationships among 12-Helical β-Peptides: Evidence of a Limit on Antimicrobial Activity," J. Am. Chem. Soc. 127, 11516-11529.
Preston et al. (2017) "Design of Lubricant Infused Surfaces," ACS Appl. Mater. Interfaces, 9, 42383-42392.
Quinn et al. (2007) "Next generation, sequentially assembled ultrathin films beyond electrostatics," *Chemical Society Reviews*, 36(5):707.
Raguse et al. (2002) "Structure-Activity Studies of 14-Helical Antimicrobial β-Peptides: Probing the Relationship between Conformational Stability and Antimicrobial Potency," J. Am. Chem. Soc. 124, 12774-12785.
Ramage et al. (2005) "Candida biofilms: an update," Eukaryot. Cell. 4:633-638.
Ramage et al. (2009) "Our current understanding of fungal biofilms," Crit. Rev. Microbiol. 35:340-355.
Ramezani-Dakhel et al. (2017) "Understanding Atomic-Scale Behavior of Liquid Crystals at Aqueous Interfaces," Journal of Chemical Theory and Computation, 13 (1): 237-244.
Rasmussen et al. (1984) "Chemistry of alkenylazlactones, 2† Reaction with thiols," Makromol. Chem. Rapid Commun. 5 (2):67-70.
Rasmussen et al. (1992) "Crosslinked, hydrophilic, azlactone-functional polymeric beads a two-step approach," *Reactive Polymers*, 16(2): 199 (1992).
Regan et al. (2019) "Droplet manipulation with bioinspired liquid-infused surfaces: A review of recent progress and potential for integrated detection," Curr. Opin. Colloid Interface Sci. 39, 137-147.
Rehfeld et al. (1967) "Adsorption of sodium dodecyl sulfate at various hydrocarbon-water interfaces," The Journal of Physical Chemistry, 71 (3): 738-745.
Reshmi et al. (2017) "Fabrication of superhydrophobic polycaprolactone/beeswax electrospun membranes for high-efficiency oil/water separation," RSC Advances, 7, 2092-2102.
Richardson et al. (Apr. 2015) "Technology-driven layer-by-layer assembly of nanofilms", *Science*, 348(6233):aaa2491.
Richardson et al. (Nov. 2016) "Innovation in Layer-by-Layer Assembly," Chem. Rev., 116: 14828-14867.
Rosenberg et al. (2016) "Turbulent drag reduction over air- and liquid-impregnated surfaces," Phys. Fluids, 28, 015103.
Rutherford et al. (2012) "Bacterial Quorum Sensing: Its Role in Virulence and Possibilities for Its Control," Cold Spring Harbor Perspect. Med, 2, a012427.
Rydzek et al. (2012) "Strategies for covalently reticulated polymer multilayers," *Soft Matter*, 8(38):9738.
Sadati et al. (2017) "Molecular Structure of Canonical Liquid Crystal Interfaces," Journal of the American Chemical Society, 139 (10): 3841-3850.
Sánchez-Velázquez, Harshit Agarwal, and David M. Lynn (Jul. 31, 2019) "Slippery Liquid Infused Porous Surfaces (SLIPS): Building New Functionality and Developing Large Scale Fabrication Methods," Poster presented at REU poster session in the University of Wisconsin-Madison Engineering Centers Building.
Schaaf et al. (2012) "Spray-Assisted Polyelectrolyte Multilayer Buildup: from Step-by-Step to Single-Step Polyelectrolyte Film Constructions," Adv. Mater., 24: 1001-1016.
Schellenberger et al. (2015) "Direct observation of drops on slippery lubricant-infused surfaces," Soft Matter, 11 (38): 7617-7626.
Schlenoff et al. (2000) "Sprayed Polyelectrolyte Multilayers," Langmuir, 16(26), 9968-9969.
Schmitt et al. (Feb. 15, 2016) "Peptide Conjugation to a Polymer Coating via Native Chemical Ligation of Azlactones for Cell Culture," Biomacromolecules. 17(3):1040-1047.
Schmitt et al. (May 20, 2015) "Polyethylene Glycol Coatings on Plastic Substrates for Chemically Defined Stem Cell Culture," Adv. Healthcare Mater. 4(10): 1555-1564.
Schönhoff (2003) "Self-assembled polyelectrolyte multilayers," *Current Opinion in Colloid & Interface Science*, 8(1): 86.
Schuster et al. (2008) "Luxr-Type Proteins in Pseudomonas aeruginosa Quorum Sensing:Distinct Mechanisms with Global Implications," In Chemical Communication among Bacteria, pp. 131-144.
Seon et al. (Nov. 18, 2015) "Polyelectrolyte Multilayers: A Versatile Tool for Preparing Antimicrobial Coatings," Langmuir. 31:12856-12872.
Shen et al. (2012) "Asymmetric free-standing film with multifunctional anti-bacterial and self-cleaning properties," ACS Appl. Mater. Interfaces. 4:4476-4483.
Sivakumar et al. (2009) "Liquid Crystal Emulsions as the Basis of Biological Sensors for the Optical Detection of Bacteria and Viruses," Adv. Funct. Mater. 19:2260-2265.
Smalley et al. (2015) "Quorum Sensing Protects Pseudomonas aeruginosa against Cheating by Other Species in a Laboratory Coculture Model," J. Bacteriol., 197 (19), 3154-9.
Smith et al. (2009) "Layer-by-layer platform technology for small-molecule delivery," Angew. Chem. Int. Ed. 48:8974-8977.
Smith et al. (Dec. 17, 2012) "Droplet mobility on lubricant-impregnated surfaces," Soft Matter. 9:1772-1780.
Soike et al. (2010) "Engineering a Material Surface for Drug Delivery and Imaging using Layer-by-Layer Assembly of Functionalized Nanoparticles," Adv. Mater. 22:1392-1397.
Solomon et al. (2014) "Drag Reduction using Lubricant-Impregnated Surfaces in Viscous Laminar Flow," Langmuir, 30, 10970-10976.
Solomon et al. (Nov. 2017) Chapter 10, Lubricant-Impregnated Surfaces, in Non-Wettable Surfaces: Theory, Preparation and Applications, The Royal Society of Chemistry, pp. 285-318.
Sotiri et al. (2016) "Immobilized liquid layers: A new approach to anti-adhesion surfaces for medical applications," Exp. Biol. Med. 241, 909-918.
Srikar et al. (2008) "Desorption-Limited Mechanism of Release from Polymer Nanofibers," Langmuir, 24, 965-974.
Stacy et al. (2012) "Attenuation of quorum sensing in the pathogen Acinetobacter baumannii using non-native N-acyl homoserine lactones," ACS Chem. Biol. 7:1719-1728.
Stamatopoulos et al. (2017) "Exceptional Anti-Icing Performance of Self-Impregnating Slippery Surfaces," ACS Applied Materials & Interfaces, 9 (11):10233-10242.
Starkey et al. (Aug. 21, 2014) "Identification of Anti-virulence Compounds That Disrupt Quorum-Sensing Regulated Acute and Persistent Pathogenicity," PLoS Pathog. 10(8):e1004321. pp. 1-17.
Subbiah et al. (2005) "Electrospinning of nanofibers," Journal of Applied Polymer Science, 96: 557-569.
Subramanyam et al. (Sep. 26, 2013) "Ice Adhesion on Lubricant-Impregnated Textured Surfaces," Langmuir. 29:13414-13418.
Sun et al. (2010) "Release of DNA from polyelectrolyte multilayers fabricated using 'charge-shifting' cationic polymers: Tunable temporal control and sequential, multi-agent release," J. Control. Release. 148:91-100.
Sunny et al. (2016) "Transparent antifouling material for improved operative field visibility in endoscopy," Proceedings of the National Academy of Sciences, 113 (42): 11676.
Sunny et al. (Sep. 1, 2014) "Lubricant-infused nanoparticulate coatings assembled by layer-by-layer deposition," Adv. Funct. Mater. 24:6658-6667.
Taff et al. (2012) "Comparative analysis of Candida biofilm quantitation assays," Med. Mycology. 50:214-218.

(56) References Cited

OTHER PUBLICATIONS

Tal-Gan et al. (2013) "Highly potent inhibitors of quorum sensing in *Staphylococcus aureus* revealed through a systematic synthetic study of the group-III autoinducing peptide," J. Am. Chem. Soc., 135 (21), 7869-82.
Tang et al. (2006) "Biomedical Applications of Layer-by-Layer Assembly From Biomimetics to Tissue Engineering", *Advanced Materials*, 18(24):3203.
Tenjimbayashi et al. (2017) "Droplet Motion Control on Dynamically Hydrophobic Patterned Surfaces as Multifunctional Liquid Manipulators," ACS Applied Materials & Interfaces, 9 (12), 10371-10377.
Teo et al. (2006) "A review on electrospinning design and nanofibre assemblies," Nanotechnology, 17, R89-R106.
Tian et al. (2016) "Fast responsive and controllable liquid transport on a magnetic fluid/nanoarray composite interface," ACS Nano, 10 (6): 6220-6226.
Tian et al. (Jul. 8, 2014) "Interfacial Material System Exhibiting Superwettability," Adv. Mater. 26:6872-6897.
Timonen eet al. (Jul. 19, 2013) "Switchable Static and Dynamic Self-Assembly of Magnetic Droplets on Superhydrophobic Surfaces," Science. 341:253-257.
Torres-Martínez et al. (2018) "A Summary of Electrospun Nanofibers as Drug Delivery System: Drugs Loaded and Biopolymers Used as Matrices," Curr. Drug Del. 15, 1360-1374.
Towle et al. (2016) "Solution Structures of Phenol-Soluble Modulins $\alpha 1$, $\alpha 3$, and $\beta 2$, Virulence Factors from *Staphylococcus aureus*," Biochemistry. 55: 4798-4806.
Tuteja et al. (2007) "Designing superoleophobic surfaces," Science. 318:1618-1622.
Ueda et al. (Jan. 23, 2013) "Emerging applications of superhydrophilic-superhydrophobic micropatterns," Adv. Mater. 25:1234-1247.
Ueda et al. (May 28, 2013) "Micropatterning hydrophobic liquid on a porous polymer surface for long-term selective cell-repellency," Adv. Healthcare Mater. 2(11):1425-1429.
Uline et al. (2010) "Surfactant driven surface anchoring transitions in liquid crystal thin films," Soft Matter, 6 (21): 5482-5490.
Vasquez et al. (2017) "Simplified AIP-II Peptidomimetics Are Potent Inhibitors of *Staphylococcus aureus* AgrC Quorum Sensing Receptors," ChemBioChem, 18, 413-423.
Verho et al. (2011) "Mechanically Durable Superhydrophobic Surfaces," Adv. Mater. 23:673-678.
Villegas et al. (2019) "Liquid-Infused Surfaces: A Review of Theory, Design, and Applications," ACS Nano, 13, 8517-8536.
Vogel et al. (Jul. 31, 2013) "Transparency and damage tolerance of patternable omniphobic lubricated surfaces based on inverse colloidal monolayers," Nat. Commun. 4:2176.
Wang et al. (2016) "Bioinspired Omniphobic Coatings with a Thermal Self-Repair Function on Industrial Materials," ACS Applied Materials & Interfaces, 8 (12): 8265-8271.
Wang et al. (2017) "Bioinspired shape-memory graphene film with tunable wettability," Sci Adv, 3 (6), e1700004-e1700004.
Wang et al. (2018) "Multifunctional ferrofluid-infused surfaces with reconfigurable multiscale topography," Nature, 559, 77-82.
Wang et al. (Aug. 2015) "Bioinspired Surfaces with Superwettability New Insight on Theory, Design, and Applications," *Chemical Reviews*, 115(16):8230.
Ware et al. (2018) "Marine Antifouling Behavior of Lubricant-Infused Nanowrinkled Polymeric Surfaces," ACS Applied Materials & Interfaces, 10 (4): 4173-4182.
Wei et al. (Sep. 18, 2014) "Supramolecular polymers as surface coatings: Rapid fabrication of healable superhydrophobic and slippery surfaces," Adv. Mater. 26:7358-7364.
Welsh et al. (Feb. 18, 2016) "Chemical genetics reveals environment-specific roles for quorum sensing circuits in Pseudomonas aeruginosa," Cell Chem. Biol. 23:361-369.
Welsh et al. (Jan. 9, 2015) "Small molecule disruption of quorum sensing cross-regulation in Pseudomonas aeruginosa causes major and unexpected alterations to virulence phenotypes," J. Am. Chem. Soc. 137:1510-1519.

Wen et al. (Jan. 2015) "Bioinspired Super-Wettability from Fundamental Research to Practical Applications," *Angewandte Chemie-International Edition*, 54(11):3387.
Wenzel (1936) "Resistance of Solid Surfaces to Wetting By Water," Ind. Eng. Chem. 28:988-994.
Wexler et al. (2015) "Shear-Driven Failure of Liquid-Infused Surfaces," Physical Review Letters, 114 (16): 168301.
Wong et al. (2011) "Bioinspired self-repairing slippery surfaces with pressure-stable omniphobicity," Nature. 477:443-447.
Wood et al. (2006) "Controlling interlayer diffusion to achieve sustained, multiagent delivery from layer-by-layer thin films," *Proceedings of the National Academy of Sciences*, 103(27):10207.
Woodruff et al. (2010) "The return of a forgotten polymer—Polycaprolactone in the 21st century," Prog. Polym. Sci. 35, 1217-1256.
Xiao et al. (Mar. 2016) "Layer-by-layer assembly of versatile nanoarchitectures with diverse dimensionality a new perspective for rational construction of multilayer assemblies", *Chemical Society Reviews*, Issue 11, 45:3088-3121.
Xiao et al. (Sep. 25, 2013) "Slippery liquid-infused porous surfaces showing marine antibiofouling properties," ACS Appl. Mater. Interfaces. 5:10074-10080.
Xin et al. (2012) "Schiff's base as a stimuli-responsive linker in polymer chemistry," Polymer Chemistry. 3(11):3045-3055.
Xu et al. (May 17, 2013) "Nacre-Inspired Design of Mechanical Stable Coating with Underwater Superoleophobicity," ACS Nano. 7:5077-5083.
Xu et al. (Nov. 7, 2012) "An Ion-Induced Low-Oil-Adhesion Organic/Inorganic Hybrid Film for Stable Superoleophobicity in Seawater," Adv. Mater. 25:606-611.
Yan et al. (2019) "Self-Adjusting Lubricant-Infused Porous Hydrophobic Sticky Surfaces: Programmable Time Delay Switch for Smart Control of the Drop's Slide," ACS Applied Materials & Interfaces, 11 (46): 43681-43688.
Yang et al. (2004) "Mechanistic Study of the Anchoring Behavior of Liquid Crystals Supported on Metal Salts and Their Orientational Responses to Dimethyl Methylphosphonate," J. Phys. Chem. B, 108(52): 20180-20186.
Yao et al. (2011) "Applications of Bio-Inspired Special Wettable Surfaces," Adv. Mater. 23:719-734.
Yao et al. (2019) "Use of a Stereochemical Strategy to Probe the Mechanism of Phenol-Soluble Modulin $\alpha 3$ Toxicity," J.Am. Chem. Soc, 141, 7660-7664.
Yao et al. (Apr. 7, 2013) "Adaptive fluid-infused porous films with tunable transparency and wettability," Nat. Mater. 12:529-534.
Yao et al. (Dec. 17, 2013) "Temperature-Driven Switching of Water Adhesion on Organogel Surface," Adv. Mater. 26:1895-1900.
Yates et al. (2002) "N-Acylhomoserine Lactones Undergo Lactonolysis in a pH-, Temperature-, and Acyl Chain Length-Dependent Manner During Growth of Yersinia pseudotuberculosis and Pseudomonas aeruginosa," Infect. Immun, 70, 5635-5646.
Yohe et al. (2012) "3D superhydrophobic electrospun meshes as reinforcement materials for sustained local drug delivery against colorectal cancer cells," J. Control. Release. 162:92-101.
Yohe et al. (2012) "Superhydrophobic Materials for Tunable Drug Release: Using Displacement of Air To Control Delivery Rates," J. Am. Chem. Soc. 134:2016-2019.
Yohe et al. (2013) "A Mechanistic Study of Wetting Superhydrophobic Porous 3D Meshes," Adv. Funct. Mater. 23:3628-3637.
You et al. (Sep. 4, 2014) "Fabrication of a Micro-omnifluidic Device by Omniphilic/Omniphobic Patterning on Nanostructured Surfaces," ACS Nano. 8:9016-9024.
Yuan et al. (2008) "Superwetting nanowire membranes for selective absorption," Nat. Nanotechnol. 3:332-336.
Yuan et al. (2016) "Liquid-Infused Poly(styrene-b-isobutylene-b-styrene) Microfiber Coating Prevents Bacterial Attachment and Thrombosis," ACS Appl. Mater. Interfaces, 8, 21214-21220.
Yuan et al. (Aug. 2020) "Weak polyelectrolyte-based multilayers via layer-by-layer assembly: Approaches, properties, and applications," Adv. Colloid Interface Sci., 282: 102200.
Zacharia et al. (2007) "Controlling Diffusion and Exchange in Layer-by-Layer Assemblies," *Macromolecules*, 40(5):1598.

(56) References Cited

OTHER PUBLICATIONS

Zacharia et al. (2007) "Factors Influencing the Interdiffusion of Weak Polycations in Multilayers," *Macromolecules*, 40(26):9523.

Zana et al. (1997) "Bolaform and dimeric (gemini) surfactants," In Specialist Surfactants, Robb, I. D., Ed. Springer Netherlands: Dordrecht, pp. 81-103.

Zander et al. (2018) "Antimicrobial and Antifouling Strategies for Polymeric Medical Devices," ACS Macro Lett. 7, 16-25.

Zelikin (2010) "Drug Releasing Polymer Thin Films: New Era of Surface—Mediated Drug Delivery," ACS Nano. 4:2494-2509.

Zhai et al. (2004) "Stable Superhydrophobic Coatings from Polyelectrolyte Multilayers," Nano Lett. 4:1349-1353.

Zhai et al. (2006) "Patterned Superhydrophobic Surfaces: Toward a Synthetic Mimic of the Namib Desert Beetle," Nano Lett. 6:1213-1217.

Zhang et al. (2006) "Erosion of multilayered films fabricated from degradable polyamines: Characterization and evidence in support of a mechanism that involves polymer hydrolysis," J Polym Sci Part A: Polym Chem, 44: 5161-5173.

Zhang et al. (2007) "Layer-by-layer assembly: from conventional to unconventional methods," Chem. Commun., 1395-1405.

Zhang et al. (2019) "The preparation of PCL/MSO/SiO2 hierarchical superhydrophobic mats for oil-water separation by one-step method," Eur. Polym. J., 116, 386-393.

Zhang et al. (Feb. 18, 2013) "Superhydrophobic and Superoleophilic PVDF Membranes for Effective Separation of Water-in-Oil Emulsions with High Flux," Adv. Mater. 25:2071-2076.

Zhang et al. (Oct. 2, 2013) "Nepenthes Pitcher Inspired Anti-Wetting Silicone Nanofilaments Coatings: Preparation, Unique Anti-Wetting and Self-Cleaning Behaviors," Adv. Funct. Mater. 24:1074-1080.

Zhong et al. (2016) "pH-Driven adsorption and desorption of fatty acid at the liquid crystal-water interface," Liquid Crystals 2016, 43 (3): 361-368.

U.S. Appl. No. 16/221,078, filed Dec. 5, 2018.
U.S. Appl. No. 15/192,364, filed Jun. 24, 2016.
U.S. Appl. No. 15/192,425, filed Jun. 24, 2016.
U.S. Appl. No. 16/740,064, filed Jan. 10, 2020.
U.S. Appl. No. 15/471,628, filed Mar. 28, 2017.
U.S. Appl. No. 16/740,008, filed Jan. 10, 2020.
U.S. Appl. No. 17/390,568, filed Jul. 30, 2021.
U.S. Appl. No. 17/390,559, filed Jul. 30, 2021.
U.S. Appl. No. 18/189,885, filed Mar. 24, 2023.

* cited by examiner

EZ 4-cyano-4'-n-pentyl-biphenly (5CB)

4-cyano-4'-n-heptyl-biphenyl (7CB)

4-cyano-4'-n-oxyoctyl-biphenyl (8OCB)

4-cyano-4''-n-pentyl-terphenyl (5CT)

Use of LC SLIP for monitoring enzymatic activity

Peptide 59

LC-SLIPS Sliding Times

- Surfactant Test
  - Surfactant: Rhamnolipid
- Sliding Conditions
  - Droplet Volume: 100 μL
  - Angle: 20°
- Tube Parameters
  - Length: 10 cm
  - Inner Diameter: 1 mm

Figure 23

LIQUID CRYSTAL-INFUSED SLIPPERY ANTI-FOULING SURFACES

CROSS-REFERENCE TO RELATED APPLICATIONS

This application claims priority from U.S. Provisional Patent Application No. 63/171,881, filed Apr. 7, 2021, which is incorporated by reference herein to the extent that there is no inconsistency with the present disclosure.

STATEMENT REGARDING FEDERALLY SPONSORED RESEARCH OR DEVELOPMENT

This invention was made with government support under GM109403 awarded by the National Institutes of Health and under 1720415 awarded by the National Science Foundation. The government has certain rights in the invention.

BACKGROUND OF THE INVENTION

Slippery liquid-infused porous surfaces (SLIPS) and lubricant-impregnated surfaces (LIS) comprise a relatively new class of synthetic soft materials fabricated by the infusion of lubricating liquids into chemically compatible nanoporous, microporous, or topographically patterned surfaces (see Wong et al., Nature 2011, 477 (7365): 443-447; Manabe et al., ACS Applied Materials & Interfaces 2015, 7 (8): 4763-4771; Huang et al., ACS Macro Letters 2013, 2 (9): 826-829; and Lafuma et al., EPL (Europhysics Letters) 2011, 96 (5): 56001; Manna and Lynn, Advanced Materials 2015, 27 (19): 3007-3012). Provided that the chemical properties of the lubricant and the underlying surfaces are suitably matched, these materials present a 'slippery' layer of mobile fluid at the surface that can repel other immiscible fluids or substances with which they come in contact (Wong et al., Nature 2011, 477 (7365): 443-447; Preston et al., ACS Applied Materials & Interfaces 2017, 9 (48): 42383-42392; Schellenberger et al., Soft Matter 2015, 11 (38): 7617-7626; and Smith et al., Soft Matter 2013, 9 (6): 1772-1780).

For example, SLIPS and LIS can shed droplets of aqueous solutions at very low sliding angles (e.g., angles less than 5° from horizontal), endowing these materials with robust anti-icing, anti-frosting, and anti-fouling properties (see also Stamatopoulos et al., ACS Applied Materials & Interfaces 2017, 9 (11): 10233-10242; Dou et al., ACS Applied Materials & Interfaces 2014, 6 (10): 6998-7003; Subramanyam et al., Langmuir 2013, 29 (44): 13414-13418; Kim et al., ACS Nano 2012, 6 (8): 6569-6577; Ma et al., Colloids and Surfaces A: Physicochemical and Engineering Aspects 2019, 577: 17-26; Sunny et al., Proceedings of the National Academy of Sciences 2016, 113 (42): 11676; Leslie et al., Nature Biotechnology 2014, 32 (11): 1134-1140; and Liu et al., Advanced Materials 2013, 25 (32), 4477-4481).

Depending on the nature of the infused oil, these materials can also prevent fouling by other complex fluids, including commercial and industrial liquids and gels, and prevent bio-fouling by microorganisms (see also Manna et al., Adv Funct Mater 2016, 26 (21): 3599-3611; Epstein et al., Proceedings of the National Academy of Sciences 2012, 109 (33): 13182; Sotiri et al., Experimental Biology and Medicine 2016, 241 (9): 909-918; and Li et al. ACS Applied Materials & Interfaces 2013, 5 (14): 6704-6711). These materials are of interest for a range of applications, including consumer packaging and containers, industrial and maritime coatings, medical devices, and sensors. Attention to practical issues such as long-term stability can further expand the commercial utility of these materials. Integration of new design principles that impart new functions and behaviors while maintaining the slippery character could also open the door to exciting and entirely new applications of these antifouling materials.

Aizenberg and co-workers reported the first examples of SLIPS by infusing perfluorinated liquids into nanofibrous Teflon (polytetrafluoroethylene (PTFE)) membranes (Wong et al., Nature, 2011, 477: 443-447). Since that initial report, many groups have expanded on the range of lubricating liquids and underlying porous matrices that can be used to fabricate SLIPS, improve their chemical and physical stabilities in complex environments, and design multifunctional coatings with improved anti-fouling behaviors, some of which rely on multilayer films to create porous surfaces that are subsequently infused with liquids (see U.S. Pat. Nos. 10,487,217, 10,557,042, and 10,557,044; Li et al., ACS Applied Materials & Interfaces 2013, 5 (14): 6704-6711; Ware et al., ACS Applied Materials & Interfaces 2018, 10 (4): 4173-4182; Huang et al., Advanced Materials 2017, 29 (8): 1604641; Guo et al., Advanced Materials 2016, 28 (32): 6999-7007; Khalil et al., Applied Physics Letters 2014, 105 (4): 041604; Wang et al., ACS Applied Materials & Interfaces 2016, 8 (12): 8265-8271; Badv et al., ACS Nano 2018, 12 (11): 10890-10902; and Goudie et al., Scientific Reports 2017, 7 (1): 13623).

The multilayer films provided several advantages over previously reported methods, including the ability to fabricate SLIPS on complex surfaces and the development of means to tune, pattern, and manipulate the interfacial properties of the materials. However, there are some limitations to the multilayer-based approach, including manufacturability and scale-up. Providing substrates other than just multilayer films would have several benefits, including decreased complexity and cost as well as increased stability and manufacturability.

It is also recognized that the properties of the infused oil can have substantial impacts on both the stability of the mobile liquid layer (e.g., the degree to which the infused oil can be displaced by a contacting fluid) and the mobility of droplets of aqueous fluid (e.g., droplets of water slide more slowly on SLIPS fabricated using higher viscosity oils, and more rapidly on coatings infused with lower viscosity liquids) (see Peppou-Chapman et al., Chemical Society Reviews 2020, 49 (11): 3688-3715; Wexler et al., Physical Review Letters 2015, 114 (16): 168301; Howell et al., Chemistry of Materials 2015, 27 (5): 1792-1800; and Daniel et al., Applied Physics Letters 2013, 102 (23), 231603). These latter observations have motivated recent work to explore the infusion of 'functional' oils with physicochemical properties that can be manipulated actively and dynamically (see also Gao et al., Adv Funct Mater 2018, 28 (35): 1803072; Che et al., Adv Funct Mater 2017, 27 (22): 1606199; and Tian et al., ACS Nano 2016, 10 (6): 6220-6226).

It was recently reported that hydrophobic nanoporous polymer coatings fabricated by covalent layer-by-layer (LbL) assembly could be infused with a thermotropic liquid crystal (LC), an anisotropic and optically birefringent fluid, to design SLIPS that respond to chemical changes in their environments (Manna and Lynn, Advanced Materials 2015, 27 (19): 3007-3012, see U.S. Pat. Nos. 10,487,217, 10,557, 042, and 10,557,044 and U.S. 2020/0325347). For example, SLIPS fabricated using a model LC in the nematic state exhibited slippery properties that changed substantially and reversibly when a contacting liquid contained (or did not contain) an amphiphilic molecule, such as a surfactant (Manna and Lynn, Advanced Materials 2015, 27 (19): 3007-3012). This work demonstrated that LC-infused SLIPS can discriminate actively based on the chemical composition of a contacting fluid, suggesting new approaches for the manipulation of droplet mobility and providing a potential basis for the design of surfaces that permit the 'naked-eye' detection of environmental analytes (for example, by reducing rates of droplet migration to levels that can be discriminated between by eye, or with the aid of a simple stopwatch).

More recently, Wang et al. reported the design of SLIPS fabricated using ferrofluids to yield so-called 'FLIPS' that can be transformed using magnetic fields to present either smooth or multiscale hierarchical surface features, providing surfaces that permit active control over the self-assembly of colloidal particles at the micrometer scale or the dislodging of bacterial biofilms at centimeter length scales (Wang et al., Nature 2018, 559 (7712): 77-82). This past work, combined with a steadily growing body of research on the functionalization and/or patterning of new rough or porous surfaces that can be used to host stable films of infused oils, has significantly expanded the range of potential applications of 'slippery' surfaces (see Huang et al., Chemistry of Materials 2019, 31 (3): 834-841; Bruchmann et al., Advanced Healthcare Materials 2017, 6 (1): 1601082; Regan et al., Current Opinion in Colloid & Interface Science 2019, 39: 137-147; Yan et al., ACS Applied Materials & Interfaces 2019, 11 (46): 43681-43688; and Tenjimbayashi et al., ACS Applied Materials & Interfaces 2017, 9 (12), 10371-10377).

The present invention provides liquid crystal (LC)-infused materials, methods of fabricating such materials, and provides methods for the detection of natural and synthetic amphiphiles, including but not limited to bacterial pathogens, in solutions. The resulting materials have desirable characteristics, including anti-fouling behavior as well as the ability to sense, discriminate between, and report on the presence of environmental analytes, including bacterial toxins. This invention also eliminates the need to coat substrates exclusively with multilayer films, and expands the range of substrates amenable for creating SLIPS.

SUMMARY OF THE INVENTION

The present invention provides liquid crystal (LC)-infused or LC-covered materials, methods of fabricating such materials, and methods for detecting compounds or impurities in liquid samples using such materials.

In an embodiment, the present invention provides a liquid crystal-infused or a liquid crystal-covered material comprising a lubricating liquid and a solid substrate able to immobilize or host the lubricating liquid, wherein the lubricating liquid wets and coats at least a portion of the substrate. The portion of the substrate coated by the lubricating fluid forms a slippery surface able to allow droplets of various materials to move across the slippery surface in a manner dependent on the chemical composition of the droplet. Other liquids placed in contact with the substrate coated by the lubricating liquid will interact with the lubricating liquid. Depending on the physical and chemical interactions between the molecules of the other liquids placed on the substrate and the lubricating liquid, differences in the behaviors of the liquids on the substrate, such as increased or decreased adhesion, mobility, or rates of sliding on the coated surface can be observed. For example, droplets of other liquids placed in contact with the substrate coated by the lubricating liquid will slide off the substrate at a rate depending on how molecules within the droplets interact with the lubricating liquid. As used here, the term "slide" encompasses other types of motion a droplet makes traveling along a surface, such as slipping, rolling, gliding, etc.

The lubricating liquid can be any liquid crystal or liquid crystalline material capable of existing in a crystal state, a liquid crystal state, or a liquid state. As used herein, "liquid crystal" means a composition in an intermediate or mesomorphic state between solid and liquid as known in the art. Suitable liquid crystals for use in the present invention include, but are not limited to, thermotropic, polymeric, lyotropic, chromonic, smectic, nematic, ferroelectric and cholesteric liquid crystals.

Examples of suitable liquid crystals, include, but are not limited to, 4-cyano-4'-n-pentyl-biphenyl (5CB), 4-cyano-4'-n-heptyl-biphenyl (7CB), 4-cyano-4'-n-octyl-biphenyl (8CB), 4-cyano-4'-n-oxyoctyl-biphenyl (8OCB), 4-cyano-4"-n-pentyl-terphenyl (5CT), liquid crystal mixture E7 (a mixture of 5CB, 7CB, 8OCB, and 5CT) (Merck KGaA, Darmstadt, Germany), liquid crystal mixture TL205 (a mixture of cyclohexane-fluorinated biphenyls and fluorinated terphenyls) (Merck KGaA, Darmstadt, Germany), and combinations thereof. Suitable liquid crystals further include smectic C, smectic C*, smectic liquid crystals formed from 8CB, blue phases, cholesteric phases, smectic A, and polymeric liquid crystals. Additional suitable liquid crystals are presented in "Handbook of Liquid Crystal Research" by Peter J. Collings and Jay S. Patel, Oxford University Press, 1997, ISBN 0-19-508442-X.

In an embodiment, the lubricating liquid is a thermotropic liquid crystal. Thermotropic liquid crystals are anisotropic liquids that possess a mesophase (i.e., a phase with both crystal and liquid properties) within a certain temperature range. As temperature is increased, the order of the molecules within the liquid crystal transitions from a highly ordered crystalline phase, to a nematic phase, followed by a disordered isotropic phase (see FIG. 1). In an embodiment, the material is present at a temperature that allows the liquid crystal to be in the liquid crystalline phase during use. Especially for embodiments where the liquid forming the droplet is an aqueous liquid, the liquid crystal is preferably immiscible or substantially immiscible in water.

The substrate can be any material able to immobilize or hold the lubricating liquid, including but not limited to porous materials, functionalized materials, and materials having surface roughness or a patterned surface, wherein the lubricating fluid is preferably able to wet the surface and form a smooth upper surface over the roughened, porous or functionalized surface. Examples of suitable substrate materials include, but are not limited to, glass, plastics, metals (including but not limited to gold, aluminum, copper, stainless steel, and titanium), paper, wood, ceramics, plastics, silicone, rubber, and polymer materials (including but not limited to polyvinyl chloride, polycarbonate, polytetrafluoroethylene (PTFE), poly(methyl methacrylate), polydimethylsiloxane (PDMS), polystyrene (PS), poly(vinyl-4,4-dimethylazlactone) (PVDMA) and poly(ethylene imine) (PEI).

In an embodiment, the material further comprises a solid support. The solid support may be an underlying non-porous material and/or a material used to provide shape or structural support. For example, in an embodiment the solid support material is a polymer or plastic tube and the substrate and lubricating liquid are deposited on the inner surface of the tube so as to prevent liquids and other materials transported through the tube from adhering to the surface.

The substrate can include curved and irregularly shaped three dimensional surfaces, as well as completely solid surfaces and mesh surfaces (e.g., having a porosity between 100 μm and 250 μm). For example, the substrate can be the interior of a tube or container for a liquid or gel where it is undesirable for the contents of the tube or container to stick or adhere to the surface. Alternatively, the substrate can be a display of a sensor where the degree or extent to which a liquid adheres to the substrate indicates the presence of a substance in the liquid.

In an embodiment, the substrate comprises a plurality of holes or pores, a three-dimensionally interconnected network of holes or pores, a random or ordered network of fibrous materials, periodically ordered porosity, or combinations thereof, that allows the lubricating liquid to fill the pores, holes and gaps within the substrate. In an embodiment, the substrate has macroscale, nanoscale, microscale, or a combination of nano- and microscale porosity, and the lubricating fluid at least partially fills the pores of the substrate. For example, in one embodiment the porous matrix has nanoscale or microscale porosity, while in an alternative embodiment, the porous matrix has macroscale porosity. Optionally, the substrate comprises a porous matrix having a plurality of pores with a pore size from 100 nm to 5,000 nm or more, preferably a pore size from 200 nm to 900 nm. Preferably, the porous matrix comprises a plurality of pores having a pore size from 100 nm to 50 µm, 100 nm to 5,000 nm, 100 nm to 1,000 nm, 200 nm to 1,000 nm, 200 nm to 950 nm, or 500 nm to 950 nm.

In an embodiment, the present invention provides a method for directly infusing liquid crystals into porous PTFE membranes. The resulting materials have desirable characteristics, including anti-fouling behavior as well as the ability to sense, discriminate between, and report on the presence of environmental analytes, including bacterial pathogens.

In an embodiment, the substrate has a surface roughness or a topographically patterned surface able to immobilize or host the lubricating liquid. The substrate is optionally patterned or treated to impart a desired surface roughness using one or more of: photolithography, projection lithography, e-beam writing or lithography, nanowire array deposition, by growing nanostructures on the surface of the substrate, soft lithography, replica molding, solution deposition, solution polymerization, electropolymerization, electrospinning, electroplating, vapor deposition, layered deposition, rotary jet spinning of polymer nanofibers, contact printing, etching, transfer patterning, micro-imprinting, self-assembly, spray coating, and combinations thereof.

Alternatively, the substrate comprises a surface that is chemically functionalized, such as with a monolayer of a material, to immobilize or hold the lubricating liquid in place. The chemically functionalized surface may be a smooth surface or a rough surface.

The lubricating fluid can infiltrate the substrate through gravity and/or capillary action. Additionally, in an embodiment, lubricating fluid removed from the surface of the substrate is replaced by lubricating fluid within the substrate, such as from within the pores. If the substrate is damaged or if the lubricating fluid is physically displaced or is removed from the surface, the lubricating fluid is capable of self-healing by wicking back to the damaged/depleted region of the substrate. The material can be designed so that the recovery time to replenish the lubricating fluid at the surface of the substrate is controllable, such as to provide a recovery time of minutes (or more), or in a matter of seconds.

In an embodiment, the portion of the substrate coated by the lubricating fluid is between one square millimeter and one square meter, preferably between one square centimeter and one square meter, preferably between one square centimeter and ten square centimeters.

As stated above, the portion of the substrate coated by the lubricating fluid forms a slippery surface allowing droplets of various materials to slide off the slippery surface. In an embodiment, droplets are able to slide off of the slippery surface when the slippery surface is at an angle between 1° and 90°, between 1° and 80°, between 1° and 70°, between 1° and 60°, between 1° and 50°, between 1° and 40°, between 1° and 30°, between 1° and 20°, between 1° and 10°, between 1° and 5°, and between 1° and 2° from horizontal. In an embodiment, the slippery surface is positioned at an angle between 0° and 1°, between 0° and 2°, between 0° and 5°, between 80° and 90°, 85° and 90°, and between 89° and 90°. Not only does this provide anti-fouling, anti-icing and other properties to the material, but the speed at which droplets slide off of the slippery surface is able to be used to detect the presence of analytes, impurities and other molecules within the droplet. For example, a droplet of water may slide off a coated substrate surface easier and faster than a droplet containing water and an amphiphilic molecule or lipophilic molecule. The sliding time of the droplet will vary based on the concentration and structure of the amphiphilic and/or lipophilic molecules present in the droplet.

Thus, in an embodiment, the present invention provides a method for detecting an analyte, substance, or impurity in a sample liquid comprising providing a sensor having a first surface area comprising: i) a lubricating liquid, wherein the lubricating liquid is a liquid crystalline material capable of existing in a crystal state, a liquid crystal state, or a liquid state; and ii) a solid substrate able to immobilize or host the lubricating liquid, wherein the lubricating liquid wets and coats at least a portion of the substrate, and wherein the portion of the substrate coated by the lubricating fluid forms a slippery surface able to allow droplets of liquids to move across the slippery surface in a manner dependent on the chemical composition of the droplet. A sample liquid, such as a droplet of a sample liquid, is provided to the first surface area, and the adhesion, mobility, or rate of sliding of the sample liquid to the first surface area is compared to a control sample or a known standard.

A change in the adhesion or mobility of the sample liquid to the first surface area, such as a difference in sliding speed or difference in an evaporation pattern deposited on the first surface area, indicates an analyte, substance, or impurity present in the sample liquid. In an embodiment, the comparisons can be measured and quantified or even performed using the naked eye. Optionally, the liquid can be dyed or reacted with a compound containing a dye or fluorophore to improve visibility. In an embodiment, differences between the time and/or speed the sample liquid travels across the first surface area and the control sample or known standard of the sample liquid are observed using one or more of a video, video with slow motion replay, computer-enhanced video, stopwatch or other timepiece, microscope, optical detector, or combinations thereof.

In a further embodiment, comparing the adhesion or mobility of the sample liquid to the first surface area comprises comparing the time and/or speed the sample liquid is able to travel across the first surface area. Optionally, the method comprises comparing the sliding times or sliding speeds of one or more droplets of the liquid sample and the sliding times or sliding speed of one or more droplets of a control sample or a known standard on a fixed length of the slippery surface and at a fixed angle. For example, in an embodiment, the fixed length is any distance between 1 cm to 100 cm of the slippery surface, and the fixed angle of the surface is 0° to 90°, 1° to 90°, 10° to 90°, 0° to 20°, 0° to 10°, 0° to 5°, 0° to 2°, 0° to 1, 1° to 20°, 1° to 10°, 1° to 5°, 75° to 90°, 80° to 90°, 85° to 90°, 88° to 90°, or 89° to 90° for the measurements. In an embodiment, an analyte or impurity in the sample liquid may decrease the sliding speed of the droplet (or even stop the droplet from moving) compared to the control sample or known standard. Alternatively, the analyte or impurity may increase the sliding speed of the droplet compared to the control sample or known standard. In an embodiment the difference in sliding speed of a droplet of a sample liquid containing an analyte or impurity compared to a control sample or known standard is 0.01 cm/s to 1 cm/s, 0.01 cm/s to 0.1 cm/s, or 0.1 cm/s to 1 cm/s.

In an embodiment, comparing the adhesion or mobility of the sample liquid comprises placing one or more droplets of the liquid sample and one or more droplets of the control sample or known standard on the first surface area, and at least partially evaporating the droplets of the liquid sample and droplets of the control sample or known standard to form evaporation patterns on the surface. Depending on the interactions between the slippery surface and a liquid droplet as it contracts during evaporation, molecules within the droplet may be deposited on the surface at different times and/or positions. As a result, altering the composition of the slippery surface, such as changing the lubricating liquid, or utilizing liquid droplets containing different analytes, substances, or impurities, will produce different evaporation patterns. Comparing the evaporation patterns on the slippery surface of a sample liquid and a control sample or known standard can therefore be used to detect the presence of analytes, substances, or impurities. In an embodiment, the comparisons are performed by imaging and/or by analyzing the deposited molecules, including but not limited to microscopy and obtaining spectroscopic measurements. In an embodiment, the comparisons are performed using the naked eye. Useful evaporation patterns may be formed by partially evaporating a droplet as well as completely evaporating the droplet.

As used herein, the sample liquid can be any fluid, including but not limited to a simple aqueous fluid, a non-aqueous fluid, a complex aqueous fluid, a viscoelastic fluid, a bodily fluid, a waste stream, or combinations thereof. Depending on the analytes, impurities and molecules that are to be detected, the droplets optionally comprise, or are suspected of comprising, amphiphilic or lipophilic small molecules or macromolecules, microorganisms selected from the group consisting of gram-negative bacteria, gram-positive bacteria, yeast, and combinations thereof, suspended particles, viruses, vesicles, polymers, proteins, or peptides. As used herein, the term "amphiphilic" refers to a compound or molecule having a hydrophobic (non-polar) region(s) and a hydrophilic (polar) region(s), including synthetic amphiphiles and biological amphiphiles. Additionally, in certain embodiments, the materials of the present invention are able to distinguish molecules, particularly peptides, based on differences in their primary structures or secondary structures and conformational changes. For example, in an embodiment, the sample liquid contains peptides or other molecules having a conformation that is different or has become different from that of a peptide or molecule being used for a comparison, including but not limited to peptides having the same or similar amino acid sequence but having different α and β motifs. In a further embodiment, the degree of α and/or β motifs present in the peptide will affect how strongly the peptide adheres to the substrate or how quickly the sample liquid containing the peptide is able to move across the surface of the material.

In an embodiment, the liquid forming the droplet is an aqueous liquid and the liquid crystal is able to exhibit planar anchoring at aqueous/liquid crystal interfaces when an analyte of interest is not present in an aqueous fluid, and is able to exhibit homeotropic anchoring at aqueous/liquid crystal interfaces when the analyte of interest is present in the aqueous fluid. In this embodiment, the analyte of interest is preferably an amphiphilic species.

In an embodiment, the present invention also provides methods for controlling liquid or droplet mobility. For example, a surfactant, salt, or other molecule may be added before or during the motion of the liquid to alter the speed the liquid's or droplet's travel along the substrate surface. Additionally, because liquid crystals may be manipulated externally by the application of magnetic or electric fields, materials described herein can exhibit interfacial properties that can be placed under active control.

In an embodiment, an agent is added to a sample liquid prior to providing the sample liquid to a surface area in order to control the mobility of the liquid, such as during a detection process. The agent physically or chemically interacts with the analyte, substance, or impurity present in the sample liquid and increases or decreases the mobility of said sample liquid on the first surface area. Preferably, the agent is an amphiphile that slows or stops the mobility of the sample liquid on the surface area when an analyte, substance, or impurity is present in the sample liquid. Alternatively, the agent increases the mobility of said sample liquid on the first surface area when the analyte, substance, or impurity is present in said sample liquid. In an embodiment, the agent is non-amphiphilic but forms an amphiphilic compound in the presence of the analyte, substance, or impurity; or the analyte, substance, or impurity is non-amphiphilic but forms an amphiphilic compound in the presence of the agent.

While the substrates of the present invention are not limited to multilayer polymer films, such multilayer films can be used with the lubricating liquid if desired. In an embodiment, the substrate comprises a bilayer having a first polymer layer and a second polymer layer. In an embodiment, a first polymer layer of the bilayer comprises a functionalized azlactone having the formula:

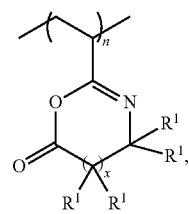

wherein x is 0 or the integers 1 or 2; and each $R^1$ is independently selected from the group consisting of: hydrogen, alkyl groups, alkenyl groups, alkynyl groups, carbocyclic groups, heterocyclic groups, aryl groups, heteroaryl groups, alkoxy groups, aldehyde groups, ether groups, and ester groups, any of which may be substituted or unsubstituted. In an embodiment, the first polymer layer comprises functionalized poly(vinyl-4,4-dimethylazlactone) (PVDMA). In a further embodiment, the PVDMA is synthesized by free-radical polymerization of PVDMA with intentionally added cyclic azlactone-functionalized oligomer in an amount ranging from 1 wt % to 10 wt %, preferably between 5 wt % and 8 wt %.

Useful functionalized azlactone polymers include, but are not limited to, poly(vinyl-4,4-dimethylazlactone), poly(2-vinyl-4,4-dimethyl-2-oxazolin-5-one), poly(2-isopropenyl-1-4,4-dimethyl-2-oxazolin-5-one), poly(2-vinyl-4,4-diethyl-2-oxazolin-5-one), poly(2-vinyl-4-ethyl-4-methyl-2-oxazolin-5-one), poly(2-vinyl-4-dodecyl-4-methyl-2-oxazolin-5-one), poly(2-vinyl-4,4-pentamethy lene-2-oxazolin-5-one), poly (2-vinyl-4-methyl-4-phenyl-2-oxazolin-5-one), poly(2-isopropenyl-4-benzyl-4-methyl-2-oxazolin-5-one), or poly(2-vinyl-4,4-dimethyl-1,3-oxazin-6-one). Useful azlactone functionalized polymers further include azlactone functionalized polyisoprenes and azlactone functionalized polybutadienes.

In an embodiment, the second polymer layer of the bilayer is optionally functionalized and comprises an amine functionalized polymer, an alcohol functionalized polymer, or a thiol functionalized polymer. Creating specific functionalities with amine, alcohol, and thiol groups is a process well known in the art (for example, see *Bioconjugate Techniques*, 2$^{nd}$ Edition, 2008, Greg T. Hermanson). In embodiments, the second polymer layer comprises an optionally functionalized polymer selected from the group consisting of poly (ethylene imine) (PEI), polylysine, pollyallylamine, poly (amidoamine) dendrimers, polyvinyl alcohol, poly hydroxyl ethyl methacrylate, poly(methacrlic acid) functionalized with cysteamine, and linear and hyperbranched and dendritic polymers functionalized with primary amines, hydroxyl groups, or thiol groups.

In embodiments, the second polymer layer comprises a polymer, which is optionally functionalized, selected from the group consisting of polyolefins, poly(alkyls), poly(alkenyls), poly(ethers), poly(esters), poly(imides), polyamides, poly(aryls), poly(heterocycles), poly(ethylene imines), poly (urethanes), poly($\alpha,\beta$-unsaturated carboxylic acids), poly($\alpha$, $\beta$-unsaturated carboxylic acid derivatives), poly(vinyl esters of carboxylic acids), poly(vinyl halides), poly(vinyl alkyl ethers), poly(N-vinyl compounds), poly(vinyl ketones), poly (vinyl aldehydes) and any combination thereof. In an embodiment, the second polymer layer comprises poly (ethylene imine) (PEI).

As used herein, "functionalized" refers to a material or polymer in which at least a portion of the individual functional groups or monomer units are substituted with a specific functional group. For the functionalized substrates and polymers of the present invention, at least 1% or more, at least 2% or more, at least 5% or more, at least 10% or more, at least 15% or more, at least 20% or more, at least 30% or more, at least 50% or more, at least 75% or more, or at least 90% or more of the portion of the functional groups or monomer units is substituted with a specific functional group.

For some embodiments, it may be desirable to further functionalize a portion of the one or more bilayers. This can be achieved, for example, by reacting a portion of any residual functional groups in the one or more bilayers with an amine group, hydroxyl group, thiol group or hydrazine, or by reacting a portion of the first or second polymer with an amine reactive group or hydroxyl reactive group.

In an embodiment, at least a portion of the residual functional groups in the bilayer is reacted such as generally described in Scheme 1 below with an amine, hydroxyl group, thiol group, or hydrazine group having the formula R—NH$_2$, R—OH, R—SH or R—NHNH$_2$, where R is hydrophobic or hydrophilic (it should be noted that the residual functional groups are not limited to azlactone groups)

Scheme 1

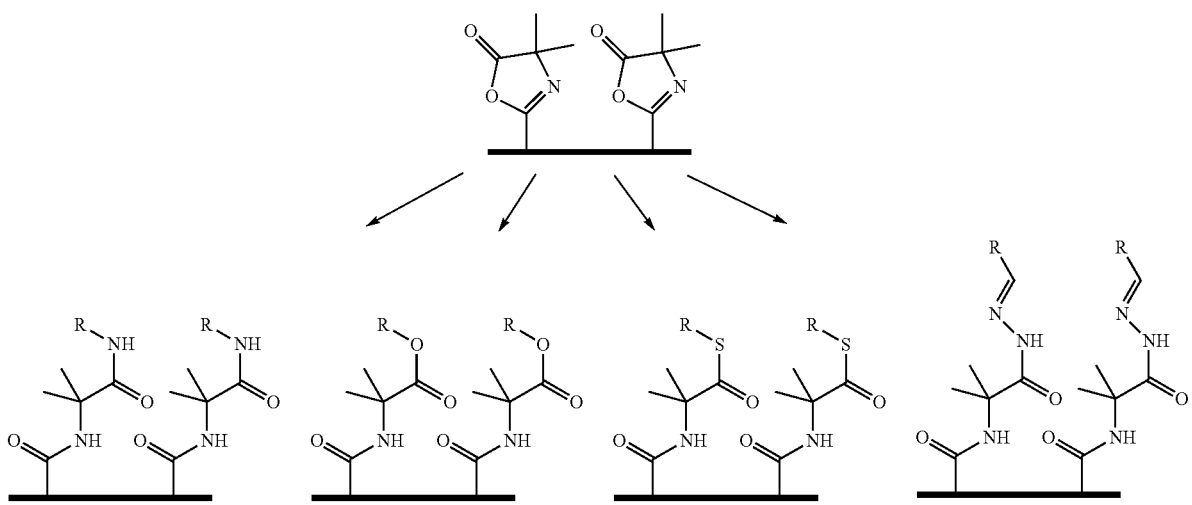

In embodiments, R is a substituted or unsubstituted C$_1$ to C$_{20}$ alkyl group, preferably a C$_1$ to C$_{12}$ alkyl group. In other embodiments, R is a substituted or unsubstituted C$_2$ to C$_{20}$ alkenyl group, preferably a C$_2$ to C$_{12}$ alkenyl group. In further embodiments, at least a portion of the residual functional groups in the bilayer is reacted with an amine selected from the group consisting of methylamine, ethylamine, propylamine, butylamine, pentylamine, hexylamine, heptylamine, octylamine, nonylamine, decylamine, and combinations thereof, preferably n-propylamine, n-octylamine, or n-decylamine. In other embodiments, R is an alkyl group substituted with one or more hydroxyl groups or charged groups such as COO$^-$ or NR3$^+$. In further embodiments, at least a portion of the residual functional groups in the bilayer is reacted with an alcohol selected from the group consisting of methanol, ethanol, propanol, butanol, pentanol, hexanol, heptanol, octanol, nonanol, decanol, and combinations thereof. In further embodiments, at least a portion of the residual functional groups in the bilayer is reacted with a thiol selected from the group consisting of methanethiol, ethanethiol, propanethiol, butanethiol, pentanethiol, hexanethiol, heptanethiol, octanethiol, nonanethiol, decanethiol, and combinations thereof. In an embodiment, at least a portion of the residual functional groups in the bilayer is reacted with an amino sugar, amino alcohol, amino polyol, glucamine (preferably D-glucamine), dimethylaminopropylamine (DMAPA), or combinations thereof. In other embodiments, at least a portion of the residual functional groups in the bilayer is reacted with a hydrazine group to form an acylhydrazine group.

In a further embodiment, at least a portion of the residual functional groups in the bilayer is reacted to form multilayer films with chemically labile amide/ester-, amide/thioester-, and amide/imine-type bonds. These chemically labile bonds are able to be broken, such as through hydrolysis, in order to undergo stimuli-responsive and reversible changes in wetting behaviors. For example, a functionalized layer (not hydrolyzed) can be designed to be hydrophobic while the functionalized layer which has been hydrolyzed to break amide/ester- or amide/thioester-type bonds can be designed to be relatively hydrophilic. In an embodiment, the polymer of the first polymer layer is further functionalized with a hydrophobic (decylamine or propylamine) or hydrophilic (glucamine) primary amine-containing small molecule.

In an embodiment, SLIPS are fabricated and infused with a thermotropic liquid crystal (an anisotropic oil) to generate sliding angles and velocities that depend critically upon the chemical compositions of contacting aqueous phases, revealing a novel 'sliding' basis for the sensing and naked-eye detection of environmental analytes, including bacterial endotoxin (i.e., LPS) and other bacterial products in aqueous media via visually apparent changes in droplet sliding speeds as a function of analyte concentration. Such LC-infused SLIPS provide opportunities to design slippery surfaces that could permit active and external control over droplet adhesion and mobility. One aspect of the invention provides thin liquid crystal-infused materials and coatings (e.g., equal to or less than 1,000 μm, equal to or less than 100 μm, equal to or less than 50 μm, preferably less than or equal to 10 μm, preferably less than or equal to 5 μm).

A specific embodiment of the present invention provides a liquid crystal-infused material based on the infusion of thermotropic liquid crystal into nanoporous or microporous (preferably nanoporous) polymer coatings fabricated by reactive layer-by-layer assembly of polymer multilayers using branched poly(ethylene imine) (PEI) and the amine-reactive polymer poly(vinyl-4,4-dimethylazlactone) (PVDMA). In an embodiment, the multilayer film comprises one or more PVDMA/PEI bilayers, which are further functionalized with a decyl group by reacting with n-decylamine and wherein the one or more bilayers are infused with a thermotropic liquid crystal.

In addition, the present invention provides SLIPS and similar slippery materials that are anti-fouling to bacteria, fungi, and mammalian cells. The liquid phases used to impart anti-fouling properties can also be used as reservoirs for the controlled release of other active agents (e.g., including but not limited to antibiotics or anti-biofilm agents, etc.) that can impart additional functions to these slippery surfaces.

Thus, the methods described herein can be used to fabricate physically and chemically durable slippery coatings on objects of arbitrary shape, size, and topology (e.g., on curved surfaces, inside hollow tubes, etc.). Specifically, these slippery surfaces could be used as antifouling surfaces, anti-bacterial/fungal surfaces, detectors, and in packaging.

BRIEF DESCRIPTION OF THE DRAWINGS

FIG. 23. Plot showing the sliding times of 100 µl water droplets containing various concentrations of rhamnolipid through polyethylene tubing where the inner surface was coated with LC-infused SLIPS. The tubing had a length of 10 cm, and inner diameter of 1 mm, and was placed at a 20° downward angle.

DETAILED DESCRIPTION OF THE INVENTION

Definitions

Figure 1:
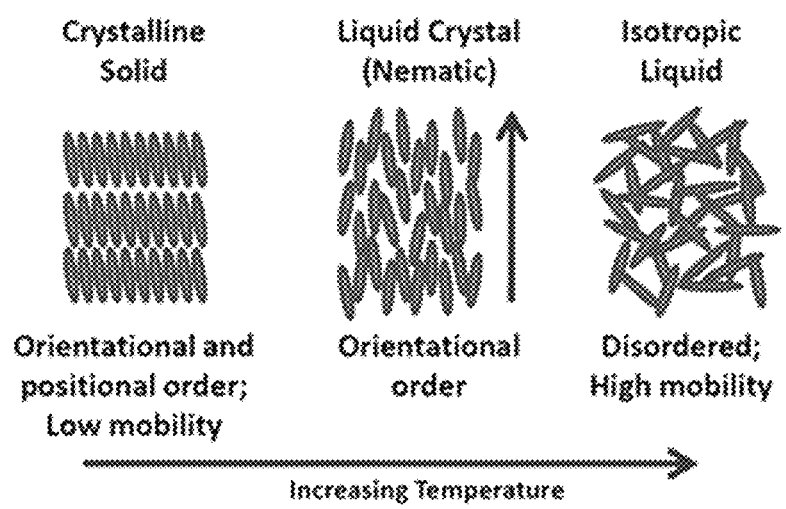
FIG. 1. (Top) Illustration of the position and orientation of molecules in thermotropic liquid crystals as temperature increases, and (Bottom) chemical structures of exemplary thermotropic liquid crystals 5CB (4-cyano-4'-pentylbiphenyl) and E7 (which is a mixture of cyanobiphenyl and cyanoterphenol liquid crystal compounds, including 5CB).
Figure 1:
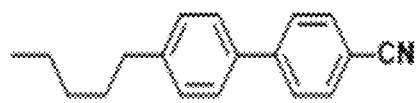
Figure 1:
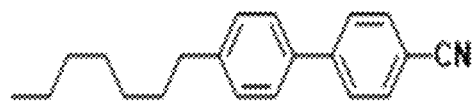
Figure 1:
Figure 1:

An "amine reactive group" or "hydroxyl; reactive group" can be any functional group able to react with an amine group or hydroxyl group, respectively.

As used herein, the term "anti-fouling" refers to a material's ability to resist adhesion by an undesirable material, such as oils, organic compounds, and organisms. In particular, it is desirable to prevent or reduce the adhesion of hydrophobic compounds and organisms to a material which is submerged or in contact with water.

The term "nanoscale" refers to a length less than 1,000 nm, preferably less than 100 nm, and the term "microscale" refers to a length less than 1,000 µm, preferably less than 100 µm.

The term "alkyl" refers to a monoradical of a branched or unbranched (straight-chain or linear) saturated hydrocarbon and to cycloalkyl groups having one or more rings. Alkyl groups as used herein include those having from 1 to 20 carbon atoms, preferably having from 1 to 12 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cycoalkyl groups include those having one or more rings. Cyclic alkyl groups include those having a 3-, 4-, 5-, 6-, 7-, 8-, 9-, 10-, 11- or 12-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 2 to 20 carbon atoms, preferably having from 2 to 12 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9-, 10-, 11- or 12-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 4 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl and alkenyl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
- —OCOOR where R is an alkyl group or an aryl groups;
- —SO$_2$N(R)$_2$ where R is a hydrogen, an alkyl group, or an aryl group and R and R can form a ring;
- —OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{12}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cycloalkenylene, $C_1$-$C_{12}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{12}$ alkenylene and $C_1$-$C_5$ alkenylene groups. The term "alkenylene" includes cycloalkenylene and non-cyclic alkenylene groups.

As used herein, the term "cycloalkenylene" refers to a divalent radical derived from a cylcoalkenyl group as defined herein. Cycloalkenylene groups in some embodiments function as attaching and/or spacer groups in the present compositions.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As used herein, the term "halo" refers to a halogen group such as a fluoro (—F), chloro (—Cl), bromo (—Br) or iodo (—I).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

OVERVIEW

The present invention discloses the design and characterization of liquid crystal (LC)-infused materials and coatings, including but not limited to materials having nanoporous or microporous polymer membranes as well as membranes having topographically patterned surfaces. The resulting materials and coatings are able to have anti-fouling behaviors that are superior to many other existing types of anti-fouling coatings, and also are able to be endowed with additional useful properties and behaviors, including the ability to sense, discriminate between, and report on the presence of environmental analytes, including bacterial toxins. Owing to the anisotropic nature of LCs and their ability to be manipulated externally by the application of magnetic or electric fields, these anti-fouling materials also have the potential to exhibit interfacial properties that can be placed under active control.

Previous SLIPS-related materials included materials fabricated by reactive layer-by-layer assembly. However, the present invention is not limited to multilayer polymer substrates and provides for a broad range of types of useful substrates that can be used. This can substantially decrease the complexity and associated cost of the system, increase overall stability, and reduce certain practical barriers to implementation in applied or manufacturing contexts.

In an embodiment, the present slippery materials are able to be used to detect and report the presence of natural and synthetic amphiphiles in aqueous solutions. For example, thermotropic LCs can be infused into microporous polymer membranes to yield LC-infused surfaces that exhibit slippery behaviors in contact with a range of aqueous fluids. In contrast to conventional liquid-infused surfaces (LIS) prepared using isotropic oils, aqueous solutions slide over the surfaces of these LC-infused materials at speeds that depend strongly upon the composition of the fluid, including the presence, concentration, or structure of a dissolved surfactant. In general, the sliding times of aqueous droplets on the LC-infused surfaces of the present invention increase significantly (e.g., from times on the order of seconds to times on the order of minutes) with increasing amphiphile concentration, allowing sliding times to be used to estimate the concentration of the amphiphile.

Additional experiments reveal other intrinsic and extrinsic variables and parameters that can be used to further manipulate droplet sliding times and discriminate among amphiphiles of similar structure. The results are consistent with a physical picture that involves reversible changes in the interfacial orientation of the anisotropic LCs mediated by the interfacial adsorption of amphiphiles. These materials thus permit facile 'naked-eye' detection and discrimination of contaminating amphiphiles in aqueous samples using equipment no more sophisticated than a stopwatch. In an embodiment of the invention, these LC-infused surfaces allow for the un-aided, naked-eye detection and monitoring of amphiphilic bio-toxins in small droplets of fluid extracted directly from cultures of two common bacterial pathogens (*P. aeruginosa* and *S. aureus*). The ability to translate molecular interactions at aqueous/LC interfaces into large and readily-observed changes in the sliding times of small aqueous droplets on surfaces allows for new applications for anti-fouling, liquid-infused materials in the context of environmental sensing and other fundamental and applied areas.

For certain practical applications of these LC-infused materials, such as environmental sensing, the materials and approaches described herein have the potential to be more useful and easier to produce and manufacture than materials fabricated using previously disclosed technology.

EXAMPLES

The work reported in the following examples was motivated by past observations of responsive behaviors in slippery LC-infused layer-by-layer coatings and the potential of these materials to enable dynamic control over the mobility of immiscible fluid droplets (Manna and Lynn, Advanced Materials 2015, 27 (19): 3007-3012, U.S. Pat. Nos. 10,487, 217, 10,557,042, and 10,557,044 and U.S. 2020/0325347). The current examples, among other things, seek to (i) expand upon those key findings and explore the generality of this approach to the design of environmentally-responsive SLIPS, (ii) provide insight into key chemical and physical factors that govern the dynamic behaviors of these LC-infused materials and their responses to fluids of varying composition, and (iii) explore the potential of LC-infused SLIPS to enable the development of new soft material platforms for the detection of environmental agents or the discovery of new chemical and biological agents.

Several examples provided herein demonstrate that thermotropic LCs can be infused into microporous PTFE thin films and porous materials coating polyethylene tubes to yield LC-infused membranes and tubes that exhibit slippery behaviors and remain physically and functionally stable when contacted with a broad range of synthetic and biological aqueous fluids. The examples also show that droplets of aqueous fluids slide over the surfaces of these LC-infused materials at speeds that depend upon the composition of the fluid (e.g., the ionic strength of the fluid or the presence, concentration, and structure of natural and synthetic amphiphiles contained within it). In general, sliding times on these LC-infused SLIPS increase significantly with increasing amphiphile concentration in the droplet, consistent with a physical picture involving the adsorption of amphiphiles at aqueous/LC interfaces and permitting measurement of differences in sliding time to be used to both identify the presence and estimate the concentration of amphiphiles in a solution. The examples also demonstrate that these materials can be used to report the presence of amphiphilic toxins in aqueous samples containing Gram-negative or Gram-positive bacteria, providing a conceptually straightforward and practical approach to the naked-eye identification of bacterial contamination. The ability of these materials to translate molecular interactions at interfaces created between aqueous solutions and thin films of LCs into large and readily-observed changes in the sliding times of small aqueous droplets has significant implications for the application of liquid-infused materials in the context of environmental sensing and other fundamental and applied areas.

It is to be understood that this invention is not limited to only the specific methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

Materials. Sodium dodecyl sulfate (SDS, ACS grade, ≥99.0%), dodecyl-trimethylammonium bromide (DTAB, ≥98.0%), hexadecyltrimethylammonium bromide (HTAB, ≥98.0%), silicone oil (η=50 cSt), Brij 30 ($C_{12}E_4$), sodium chloride (NaCl, ACS grade, ≥99.0%) and 3-oxo-C12-AHL were obtained from Millipore Sigma (Milwaukee, Wis.). The thermotropic liquid crystals 5CB and E7 were purchased from Jiangsu Hecheng Display Technology Co. (Jiangsu, China). Phosphate-buffered saline (PBS) (137 mM NaCl, 2.7 mM KCl, 10 mM phosphate; pH 7.4) was prepared from OmniPur® 10× concentrate (Millipore Sigma, Milwaukee, Wis.). Unlaminated PTFE membrane filters (pore size=0.2 μm, thickness=25-51 μm) were purchased from Sterlitech Corporation (Kent, Wash.). Eutrophic lake water was locally sourced from Lake Mendota, Madison, Wis. Nature's Touch skim milk was purchased from Kwik Trip (Madison, Wis.). Pooled human urine was purchased from Innovative Research Inc. (Novi, Mich.). Luria-Bertani medium (LB), Lennox formulation, was purchased from Research Products International (Mt. Prospect, Ill.). Brain heart infusion (BHI) medium was purchased from Teknova (Hollister, Calif.). N-Butanoyl-L-homoserine lactone (BHL) was purchased from Cayman Chemical (Ann Arbor, Mich.). Dodecyl-1,12-bis(trimethyl-ammonium bromide) (DBTAB) was a gift from Cornell University, Ithaca, N.Y. The phenol-soluble modulin PSM-α-3 was a gift from UW-Madison, Madison, Wis. Rhamnolipids (90% pure) were obtained from AGAE technologies (Corvallis, Oreg.). 3-(3-Hydroxy-alkanoyloxy) alkanoic acid (HAA) and AIP-III D4A were synthesized according to previously reported methods. The use of the term 'water' in all sections below refers to water with a resistivity of 18.2 MΩ, obtained from a Millipore filtration system, unless otherwise noted. All materials were used as received without further purification unless otherwise noted.

General Considerations. Scanning electron micrographs were acquired using a LEO 1550 scanning electron microscope at an accelerating voltage of 3 kV. Samples were coated with a thin layer of gold using a gold sputterer operating at 10 mA under a vacuum pressure of 50 mTorr for 1 min prior to imaging. Digital photographs and videos were acquired using a Samsung Galaxy S7 smartphone. Sliding time data were analyzed using Microsoft Excel and plotted using GraphPad Prism 7 (version 7.0h). For measurements of absorbance at 600 nm ($OD_{600}$) to monitor bacterial growth, 200 μL of culture were added to a clear-bottomed 96-well plate (Corning 3370) and absorbance was measured using a Synergy 2 plate reader (Biotek) with Gen5 1.05 software.

Preparation of SLIPS. SLIPS were prepared at ambient room temperature (~20° C.) by depositing a lubricating liquid (e.g., either the LCs 5CB or E7, or silicone oil) on the top surface of a porous polymer membrane (supported on a glass slide) using a pipette. The lubricating liquid was then spread using tweezers to form a uniform over-coated layer. Samples were allowed to stand for several minutes to allow the liquid to infuse into the porous membrane (evident by a visual change in the opacity of the membrane) through capillary wicking. The excess liquid was then removed from the surface by dabbing with weighing paper.

Example 2

Characterization of Droplet Sliding Times. Characterization of the sliding times of droplets placed on the surfaces of LC-infused SLIPS was performed in the following general manner. LC-infused SLIPS were placed on a custom-made stage, and the stage was attached to the moving arm of a digital protractor using binding clips. The digital protractor was set at a specified sample angle, and a pre-determined volume of aqueous solution was placed as a droplet on the surface of the liquid-infused surface. Sliding droplets were recorded on digital video, and the time required for droplets to slide 4.0 cm along the surface was measured using a digital timer. In some cases, aqueous solutions were prepared by adding food coloring to enhance visual contrast of the sliding droplets. For characterization of the sliding times of different bacterial strains, three biological replicates were performed. After each measurement, the surface was washed by depositing multiple water droplets and allowing them to slide down the surface until the sliding time of the water droplets returned to a value of ~3 s. For each surfactant solution, the sliding times of at least 3-5 droplets were measured and used to calculate an average sliding time with standard deviation. Each experimental series was performed on one common LC-infused slippery surface, with appropriate experimental controls, in order to prevent variability in sliding time measurements between different LC-infused surfaces.

Bacteria and Culture Conditions. All bacteria were grown at 37° C., with shaking at 200 rpm (see Table 1 for strain and plasmid information). *S. aureus* was cultured in BHI medium; all other species were grown in LB medium. For all strains, an overnight culture was grown in a 15 mL glass tube (no more than 2 mL of culture) or a 25 mL Erlenmeyer flask (no more than 5-10 mL of culture) to allow for sufficient aeration. Experiments using *S. aureus* proceeded as follows: An overnight culture of bacteria (strain 6390 or 9222) was diluted 1:100 in fresh BHI medium, and the peptide AIP-III D4A (if applicable) was added to achieve a final concentration of 1 μM. DMSO was added as a vehicle control (no greater than 2% final concentration) to cultures not containing this peptide. Experiments using *Pseudomonas aeruginosa* proceeded as follows: An overnight culture of bacteria was diluted 1:100 in fresh LB medium and shaken for 24 h, unless otherwise specified. To induce RhIR phenotypes in PAO-SC4 (ΔIasI rhII), BHL was added to achieve a final concentration of 200 μM. DMSO (no greater than 2%) was added to cultures as a vehicle control for experiments not containing added AHL.

TABLE 1

| Bacterial strain and plasmids used. | | | |
|---|---|---|---|
| | Referred to herein | Genotype | Reference or Source |
| *Staphylococcus aureus* | | | |
| RN6390b | *S. aureus* WT | Wild type, agr group I (NTCC8325 cured of prophages) | Novick |
| RN9222 | QS mutant | RN6911 with pRN7035 | Lyon et al. |
| RN6911 | N/A | tetM::agr, from RN6390 Plasmid | Novick et al. |
| pRN7035 | QS mutant | agrCA and agr-P3::blaZ fusion | Lyon et al. |
| *Pseudomonas aeruginosa* | | | |
| PAO1 | N/A | Wild type, isolated from wound | Holloway |
| mPAO1 | PAO1, WT | Wild type, derivative of Holloway's isolate | Gift from E. P. Greenberg |
| PAO1-T | N/A | Wild type, derivative of Holloway's isolate | WT from PA two-allele library |

TABLE 1-continued

Bacterial strain and plasmids used.

| | Referred to herein | Genotype | Reference or Source |
|---|---|---|---|
| PAO-SC4 | ΔlasI rhlI | lasI rhlI in-frame deletions | Gift from E. P. Greenberg |
| PAO1 ΔrhlB | ΔrhlB | Unmarked, in-frame rhlB deletion | Smalley et al. |
| PAO1-T ΔrhlA (PW6886) | ΔrhlA | rhlA-E08::IsphoA/hah | PA two-allele library |

LC-Infused PTFE Membranes Influence the Sliding of Aqueous Droplets Containing Surfactant. Past work demonstrated that the infusion of a thermotropic LC into hydrophobic and nanoporous polymer coatings fabricated by reactive/covalent layer-by-layer assembly can be used to design SLIPS that respond actively to changes in the chemical composition of the contacting liquid (e.g., the presence or absence of surfactants) (Manna and Lynn, Advanced Materials 2015, 27 (19): 3007-3012). As a step toward investigating the broader utility of this approach and addressing practical challenges associated with the use of layer-by-layer coatings, it was sought to characterize the infusion of LCs into commercially available and single-component nanoporous PTFE membranes that have been used as matrices for the infusion of conventional isotropic oils to design SLIPS in other past studies (see Wong et al., Nature 2011, 477 (7365): 443-447; Epstein et al., Proceedings of the National Academy of Sciences 2012, 109 (33): 13182; Daniel et al., Applied Physics Letters 2013, 102 (23): 231603; and Yao et al., Nature Materials 2013, 12 (6): 529-534).

Figure 6:
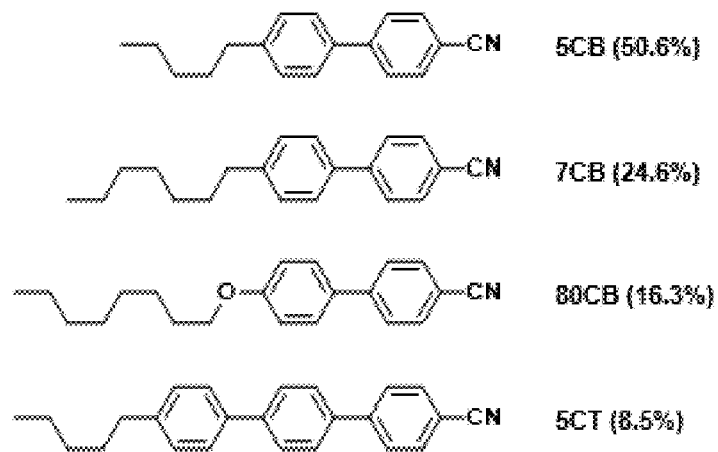
FIG. 6. Illustration of thermotropic liquid crystal E7 being a combination of four different liquid crystals mesogens (5CB, 7CB, 8OCB, and 5CT).
Figure 7:
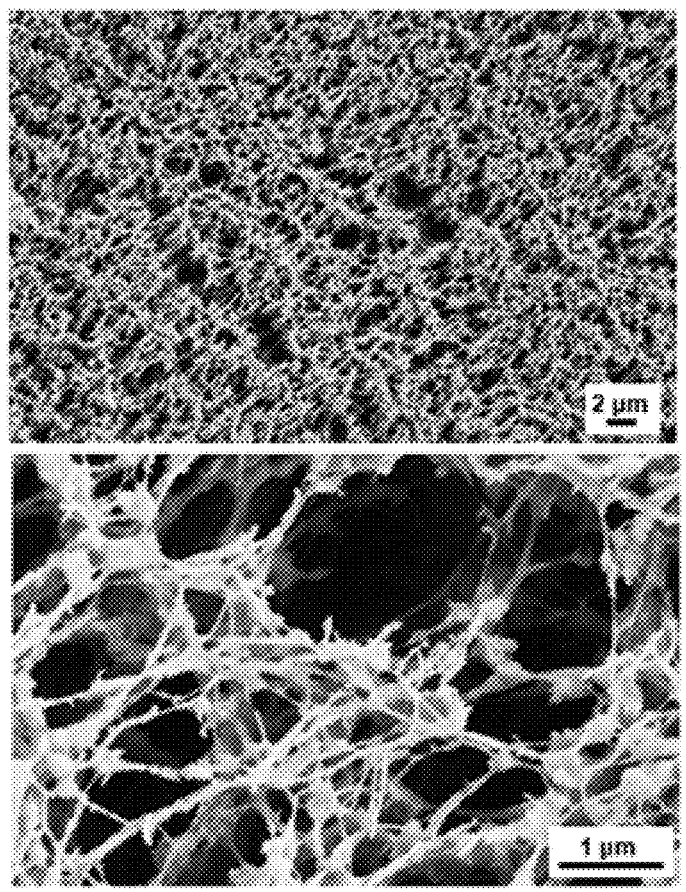
FIG. 7. Low and high magnification 'top-down' SEM images of PTFE membrane showing nanoporosity.

A series of experiments was first performed to determine whether PTFE membranes could be infused with thermotropic LCs in the nematic state, and whether the resulting LC-infused membranes were 'slippery' and chemically or physically stable upon contact with a broad range of liquids. The infusion of thermotropic LC into porous PTFE membranes with pore sizes of 200 nm and thicknesses of 25-51 μm resulted in LC-infused SLIPS that allowed aqueous droplets to slide readily on the surface (the LC used in these experiments was E7 unless otherwise noted; the chemical structures of the mesogens that comprise this LC are shown in FIG. 6; SEM images showing top-down views of these membranes are shown in FIG. 7).

Figure 2:
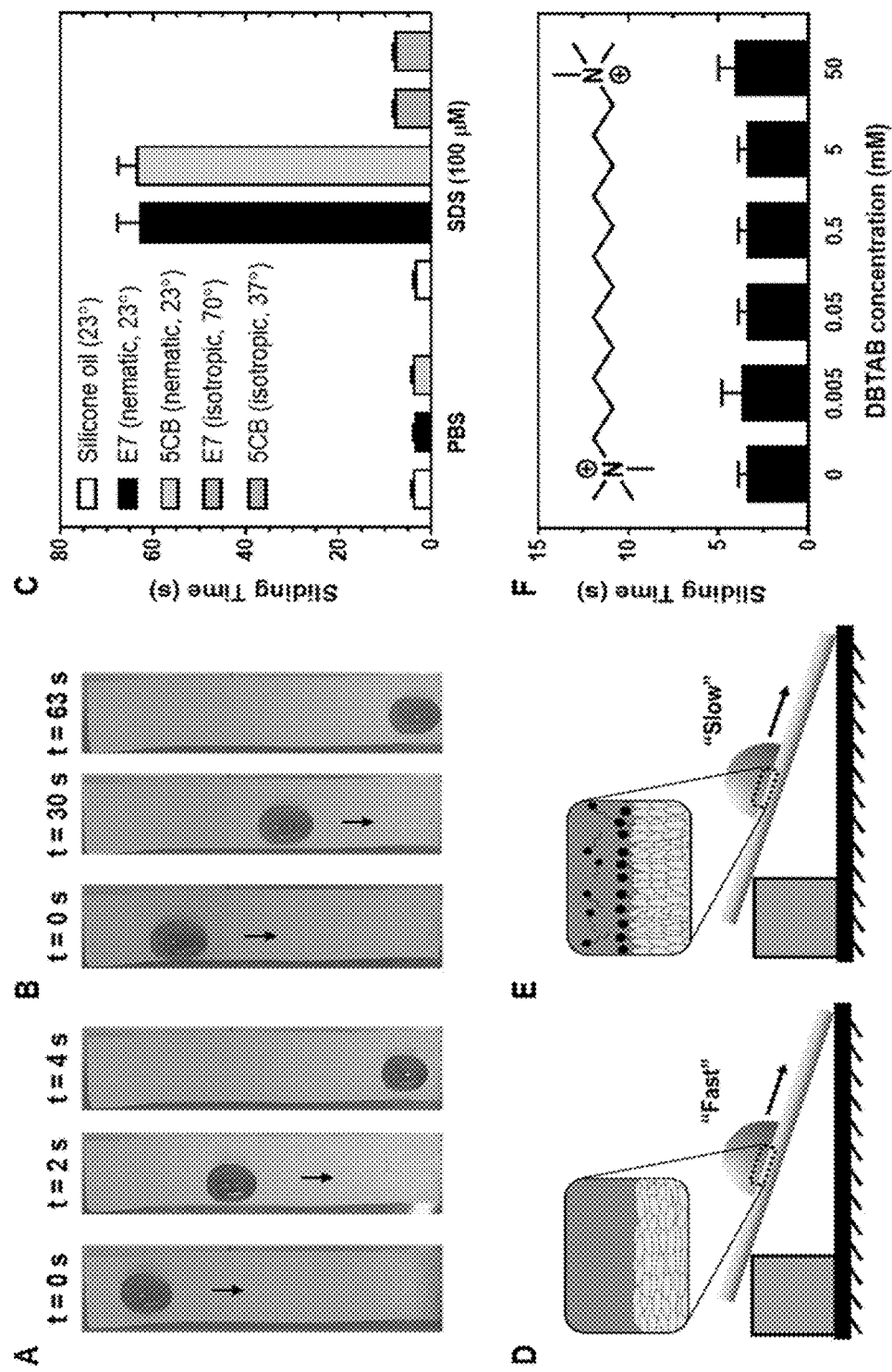
FIG. 2. (Panels A,B) Images showing 'top-down' view at different time points of (A) a droplet of phosphate-buffered saline (PBS) (50 μL), and (B) a PBS droplet containing 100 μM sodium dodecyl sulfate (SDS) (50 μL) sliding down E7-infused SLIPS tilted at 20°. (Panel C) Plot showing sliding behaviors of droplets of PBS or PBS droplets containing SDS (100 μM) on PTFE membranes infused with silicone oil (white), thermotropic liquid crystals E7 (black) and 5CB (gray) at 23° C., the second from the right and furthest right bars show the sliding behaviors of PBS droplets containing SDS on E7-infused SLIPS equilibrated to a temperature of 70° C. and 5CB-infused SLIPS equilibrated to a temperature of 37° C., respectively. Results are expressed as the time required for a 50 μL droplet to slide 4 cm on the surface tilted at 20°. (Panels D,E) Schematic showing proposed changes in the anchoring of LCs from (D) planar to (E) homeotropic upon adsorption of surfactant to the aqueous-LC interface formed between a surfactant-containing aqueous droplet sliding down an inclined LC-infused SLIPS (yellow). (F) Plot showing the sliding time of 50 μL DBTAB-containing water droplets (0.005-100 mM) on E7-infused SLIPS tilted at 20°.
Figure 8:
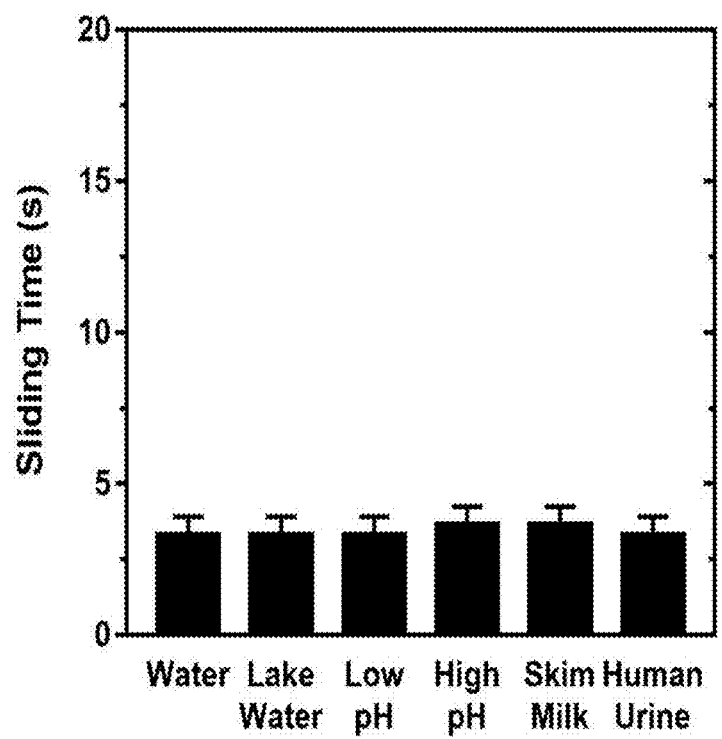
FIG. 8. Plot showing sliding time of 50 µL droplets of various liquids (Milli-Q water, unfiltered eutrophic lake water, acidic (pH 1) and alkaline (pH 11) solution, fat free milk and pooled human urine) sliding on E7-infused SLIPS tilted at 20°.

FIG. 2, panel A, shows top-down views of a 50 μL droplet of PBS placed on an LC-infused SLIPS tilted at 20°; the droplet was observed to slide over a length of 4 cm in ~4 s (similar sliding behavior was also observed for water droplets placed on LC-infused SLIPS). The high degree of mobility of water droplets on these LC-infused membranes is consistent with the presence of a 'slippery' LC lubricant phase on the porous PTFE membrane that remains stable in the presence of water droplets ($S_{os(w)} \geq 0$; see Table 2). The LC-infused SLIPS were also stable when contacted with a broad range of chemically complex liquids, including acidic (pH 1) and alkaline (pH 11) aqueous solutions, fat free milk, unfiltered lake water, and human urine. As shown in FIG. 8, 50 μL droplets of these different liquids placed on LC-infused SLIPS tilted at 20° were also observed to slide over a length of 4 cm in ~4 s, similar to the behaviors of water droplets.

TABLE 2

Evaluation of the stability of 5CB- and E7-SLIPS in presence of water droplets.

| Parameters | 5CB-SLIPS | E7-SLIPS |
|---|---|---|
| $\Theta_{ws(a)}$ | 114 ± 1 | 114 ± 1 |
| $\Theta_{os(a)}$ | 51 ± 3 | 48 ± 3 |
| $\gamma_{ow}$ | 28.1 ± 0.4 | 27.5 ± 0.8 |
| $\gamma_{oa}$ | 31.2 ± 0.6 | 29 ± 0.5 |
| $\gamma_{wa}$ | 72.1 ± 0.2 | 72.1 ± 0.2 |
| $S_{os(w)}$ | 20.8 ± 5.7 | 21.2 ± 5.8 |

For Table 2, the unit of contact angle is in degrees. The contact angles are measured on a flat smooth PTFE surface using 5 μL water droplet for $\Theta ws(a)$ and 5 μL 5CB and E7 for $\Theta os(a)$. The unit of surface tension and interfacial tension is mN/m. Surface tension (γoa, γwa) and interfacial tension (γow) measurements were performed by the pendant drop method at ambient conditions (temperature=22 to 24° C. and relative humidity=12 to 20%). Density of water used for measurements was 0.997 gm/ml and density of 5CB and E7 is 1.03 gm/ml. The values denote the mean of three independent measurements and error denotes standard deviation. Sos(w)=γoa cos Θos(a)−γwa cos Θws(a)−γow≥0 and the units of Sos(w) is in mN/m. Θos(a)>0 suggests that the surface of the PTFE membrane can emerge out of the lubricating liquid phase in areas outside the water droplet.

It was previously reported that water droplets containing surfactants slide more slowly on LC-infused SLIPS fabricated by the infusion of E7 into nanoporous PEI/PVDMA multilayer films as compared to droplets of water alone (Manna and Lynn, Advanced Materials 2015, 27 (19): 3007-3012). Similar differences were observed in the sliding behaviors of droplets with and without surfactants on LC-infused SLIPS fabricated by infusion of E7 into the PTFE membranes described here. SDS-containing droplets were observed to slide very slowly compared to droplets of PBS. For example, as shown in FIG. 2, panel B, a droplet of PBS containing 100 μM SDS slid over a length of 4 cm in ~63 s, compared to the ~4 s time required for a PBS droplet that did not contain surfactant (FIG. 2, panel A).

The sliding times of SDS-containing droplets was also measured on E7-infused SLIPS maintained at 70° C., a temperature well above the nematic/isotropic transition temperature of E7 (~60° C.). As shown in FIG. 2, panel C (bar second from the right) the SDS-containing droplets slid over a length of 4 cm in ~8 s, a time that is significantly faster than that observed on surfaces infused with E7 in the nematic state at ambient room temperature (~63 s). Additional experiments using SLIPS fabricated by the infusion of the thermotropic liquid crystal 5CB (in the nematic state) instead of E7 into PTFE membranes revealed similar results (the structure of 5CB is shown in FIG. 6; 5CB-infused SLIPS maintained a 'slippery' lubricant phase in the presence of water droplets ($S_{os(w)} \geq 0$); see Table 2). As shown in FIG. 2, panel C, a 100 µM SDS-containing droplet slid ~15 times slower (~63 s) on 5CB-infused surfaces compared to PBS droplets (~4 s). However, for 5CB-infused SLIPS maintained at 37° C., a temperature above the nematic/isotropic transition temperature (~35° C.) of this LC, SDS-containing droplets again slid appreciably faster (bar furthest on the right; ~8 s) (FIG. 2, panel C). Lastly, as also shown in FIG. 2, panel C, it was noted that no differences in sliding times were observed between SDS-containing droplets and droplets of PBS on PTFE membranes infused with silicone oil, a model isotropic oil (both types of droplets slide over a length of 4 cm in ~4 s).

The results of these experiments demonstrate that the novel responsive sliding behaviors observed in past studies using layer-by-layer coatings are preserved when more well characterized and single-component commercial porous PTFE membranes are used as host substrates. When combined, these results support the hypothesis that changes in droplet sliding speeds are the result of the anisotropic nature of the infused LC and its behavior at interfaces created with aqueous media (that is, the large changes in droplet sliding times observed here occur in ways that are independent of the nature of the underlying substrate). On the basis of these results, it is concluded that the infusion of LCs could likely also be used more generally to impart responsive behaviors to SLIPS fabricated using a variety of other well-known hydrophobic matrices used to fabricate slippery surfaces.

Example 3

Characterization of liquids in LC-infused tubes. The LC-infused SLIPS of the present invention are not limited to substantially flat surfaces but can also include curved surfaces, containers, and tubes.

Polyethylene tubes having inner diameters of 5 mm and a length of 5 cm (see FIG. 20) were coated with LC-infused SLIPS. 50 µl droplets of deionized water containing food coloring were in placed in the tubes and similar polyethylene tubes that were not coated with LC-infused SLIPS. The tubes were placed at a 25° angle, and the time for the droplets to pass through the LC-SLIPS-coated tubes was recorded.

Figure 20:
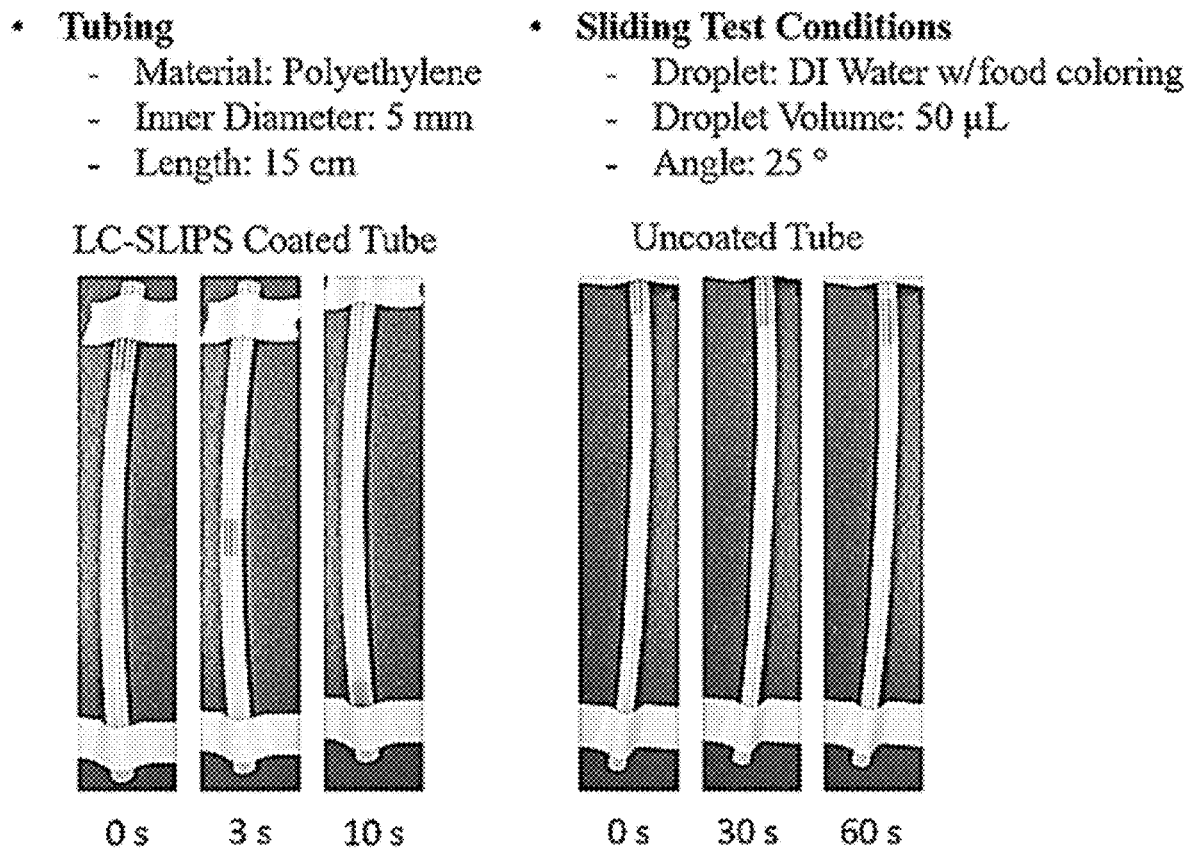
FIG. 20. Images of uncoated polyethylene tubing and polyethylene tubing where the inner surface was coated with LC-infused SLIPS. Droplets of deionized water containing food coloring were inserted in one end of the tubing and the tubing was placed at a 25° downward angle. The position of the droplets at 0 seconds, 3 seconds and 10 seconds are shown for the coated tubing, and the position of the droplets at 0 seconds, 30 seconds and 60 seconds are shown for the uncoated tubing.

As illustrated in FIG. 20, the water droplets were able to travel through the LC-SLIPS coated tubes in 10 seconds or less, while water droplets had relatively little movement through the uncoated tubes over the same time period.

Figure 21:
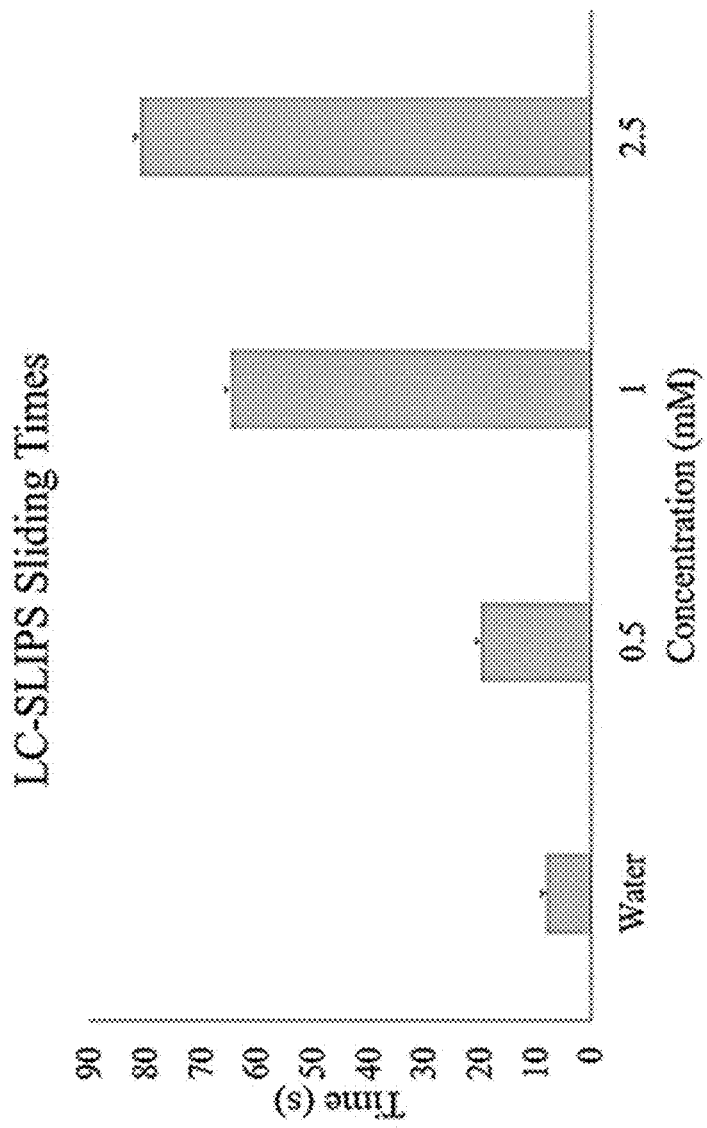
FIG. 21. Plot showing the sliding times of 50 µl water droplets containing various concentrations of sodium dodecyl sulfate (SDS) through polyethylene tubing where the inner surface was coated with LC-infused SLIPS. The tubing had a length of 10 cm, and inner diameter of 1 mm, and was placed at a 25° downward angle.
Figure 22:
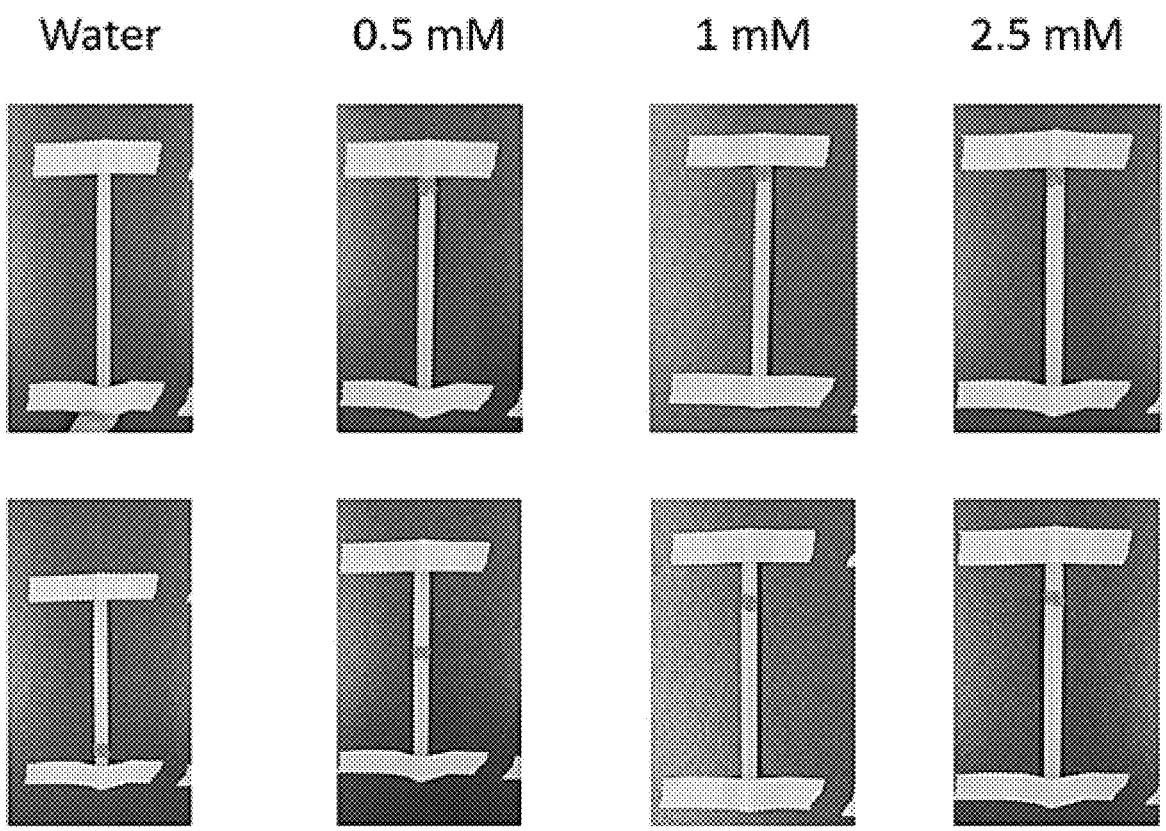
FIG. 22. Images of uncoated polyethylene tubing (top row) and polyethylene tubing where the inner surface was coated with LC-infused SLIPS (bottom row). Water droplets containing various concentrations of sodium dodecyl sulfate (SDS) were inserted in one end of the tubing and the tubing was placed at a 25° downward angle. The position of the droplets at approximately 10 seconds are shown for the different concentrations of the SDS (0 mM, 0.5 mM, 1 mM, and 2.5 mM).

Various concentrations of a surfactant (SDS or rhamnolipid) were added to water droplets and similar experiments were performed on 10 cm polyethylene tubes coated with LC-infused SLIPS and having an inner diameter of 1 mm. The sliding time of the droplets through the tube increased as the concentration of the surfactant increased (see FIGS. 21-23).

These experiments illustrate that coating tubes with LC-infused SLIPS produces similar trends in sliding behavior as those seen with the flat surfaces as described in the experiments above.

Example 4

Influence of Amphiphile Structure and Other Parameters on Droplet Sliding Speeds. It is speculated that the slower sliding speeds of surfactant-containing droplets shown in FIG. 2, panel B, result from dynamic changes in the anchoring of the LCs (see schematic in FIG. 2, panels D and E) as aqueous/LC interfaces are formed beneath a droplet and surfactant adsorbs there. It is well understood that thermotropic LCs such as E7 and 5CB adopt so-called homeotropic anchoring when hosted at LC-air interfaces (i.e., the mesogens are generally aligned perpendicular to the interface), and that they adopt so-called planar anchoring when hosted at interfaces created between LCs and water (i.e., the mesogens are generally aligned parallel to the interface) (Sadati et al., Journal of the American Chemical Society 2017, 139 (10): 3841-3850; Ramezani-Dakhel et al., Journal of Chemical Theory and Computation 2017, 13 (1): 237-244; Carlton et al., Langmuir 2012, 28 (35): 12796-12805; Carlton et al., Langmuir 2012, 28 (1): 31-36; and de Mul et al., Langmuir 1994, 10 (7): 2311-2316).

In addition, previous studies have reported that adsorption of surfactants such as SDS at aqueous/LC interfaces can result in an orientational transition in the anchoring of LCs from planar to homeotropic orientations at the interface (Popov et al., Journal of Materials Chemistry B 2017, 5 (26): 5061-5078; Carlton et al., Liq Cryst Rev 2013, 1 (1): 29-51; Gupta et al., Langmuir 2009, 25 (16): 9016-9024; Lockwood et al., Surface Science Reports 2008, 63: 255; Brake et al., Langmuir 2003, 19 (16): 6436-6442; Brake et al., Science 2003, 302 (5653): 2094; and Brake et al., Langmuir 2002, 18 (16): 6101-6109).

In the experiments reported above, a water droplet placed on LC-infused SLIPS results in the formation of an aqueous/LC interface under the droplet, and the LCs near that interface would be expected to exhibit planar anchoring (Schellenberger et al., Soft Matter 2015, 11 (38): 7617-7626; Smith et al., Soft Matter 2013, 9 (6): 1772-1780 and Daniel et al., Nature Physics 2017, 13 (10): 1020-1025). A water droplet containing a surfactant also results in the formation of an aqueous/LC interface, however the surfactant molecules in the droplet should also adsorb at the aqueous/LC interface and, thereby, promote homeotropic anchoring in the underlying LC. The orientation of the LCs in the experiments described above were unable to be characterized using polarized light microscopy, a method commonly used to characterize the orientation of LCs at LC/aqueous interfaces, because of the complexities of the system used here, including the opacity and thickness of the PTFE membranes (Zhong et al., Liquid Crystals 2016, 43 (3): 361-368; Carlton et al., Langmuir 2014, 30 (49): 14944-14953; Miller at al., Langmuir 2013, 29 (10): 3154-3169; and Manna et al., Angewandte Chemie International Edition 2013, 52 (52): 14011-14015). However, the results reported above, when combined with those of past studies in LC-infused layer-by-layer coatings, and the results of additional experiments reported below involving surfactants with different tail lengths and head groups, are consistent with this general hypothesis.

It is anticipated that any potential changes from planar to homeotropic anchoring that occur at aqueous/LC interfaces created by contact with aqueous droplets containing surfactant would occur and form continuously at that interface as the droplet slides along the surface. Changes in the speeds of droplets were not observed as they slid along LC-infused surfaces, providing general support for this hypothesis. It is, of course, possible that the concentration of surfactant in an aqueous droplet could become depleted if some of it remains bound at air/LC interfaces created in areas behind a sliding droplet (that is, sliding droplets could leave behind 'trails' of adsorbed surfactants as they move across a surface, which would result in a concomitant reduction in surfactant concentration in the droplet). Changes in surfactant concentration were not measured in the droplets in the examples performed here, and if surfactant depletion does occur, it did not occur to extents that resulted in significant changes in droplet sliding speed at the surfactant concentrations and path lengths evaluated in the experiments above. It is noted, however, that PBS droplets placed on surfaces previously exposed to sliding SDS-containing droplets were observed to slide over a distance of 4 cm over ~7 s, a time that is slower than the sliding times of PBS droplets on fresh LC-infused PTFE membranes that were never exposed to surfactant-containing droplets (~4 s, as described above).

This difference in sliding times is generally consistent with the view that surfactant from sliding droplets could remain at LC/air interfaces after surfactant-laden droplets have moved along the surface. It is further noted, in this context, that the sliding times of PBS droplets on 'previously used' LC-infused SLIPS returned to values of ~4 s and were otherwise indistinguishable from freshly-prepared surfaces after 'rinsing' them with 3-5 additional water droplets. This result suggests that the adsorption of surfactant, to whatever extent it may occur, is reversible. In general, it was possible to use, rinse, and reuse these LC-infused SLIPS multiple times with no observable changes in subsequent droplet sliding behaviors, with the one exception of cases in which substantially high surfactant concentrations (e.g., above CMC) were used. Under those conditions, the sliding droplets appeared to remove LCs from the membranes, resulting in an erosion of membrane performance. However, in most cases, this damage could be reversed, and the performance of the membranes could be restored, by the addition of more LC to the surface of the membrane.

To investigate further the role that homeotropic anchoring of LC may play in influencing droplet sliding speeds, the sliding speed of aqueous droplets containing the cationic bolaform surfactant dodecyl-1,12-bis(trimethylammonium bromide) (DBTAB; structure shown in FIG. 2, panel F) was also evaluated. DBTAB adopts a looped configuration at oil/water interfaces and has a much higher limiting surface area (~107 $Å^2$ at an air-water interface) compared to the limiting surface area of analogous classical surfactants (e.g., 55-63 $Å^2$ for DTAB) that adopt tilted configurations at air/water interfaces (see Brake et al., Langmuir 2003, 19 (16): 6436-6442; Daniel et al., Nature Physics 2017, 13 (10): 1020-1025; Zhong et al., Liquid Crystals 2016, 43 (3): 361-368; Carlton et al., Langmuir 2014, 30 (49): 14944-14953; Miller et al., Langmuir 2013, 29 (10): 3154-3169; Manna et al., Angewandte Chemie International Edition 2013, 52 (52): 14011-14015; Martinez et al., Proceedings of the Royal Society A: Mathematical, Physical and Engineering Sciences 2011, 467 (2131): 1939-1958; Zana et al., In *Specialist Surfactants*, Robb, I. D., Ed. Springer Netherlands: Dordrecht, 1997; pp 81-103; and Menger et al., The Journal of Physical Chemistry 1974, 78 (14): 1387-1390).

Past studies report that DBTAB promotes planar, rather than homeotropic, anchoring of 5CB at aqueous/LC interfaces at concentrations ranging from 0.01 mM to 100 mM (Brake et al., Langmuir 2003, 19 (16): 6436-6442). The contact angle (77°±1°) and droplet base diameter (4.0±0.04 mm) of 50 μL 100 mM DBTAB-containing aqueous droplets on LC-infused SLIPS is similar to the contact angle (74.4°±0.7°) and droplet base diameter (4.14±0.02 mm) of 50 μL 100 μM SDS-containing PBS droplets. However, aqueous droplets containing between 5 μM to 100 mM DBTAB were observed to slide over a distance of 4 cm in ~3 s (FIG. 2, panel F), a sliding time comparable to those of droplets of water alone, and a time that is substantially faster than those of droplets containing SDS (~63 s).

It was also noted that the concentrations evaluated here encompass the CMC of DBTAB (20-50 mM) and are above the observed onset of surface activity of DBTAB at the air-water interface (<1 mM) (Brake et al., Langmuir 2003, 19 (16): 6436-6442; Zana et al., 1997; pp 81-103; and Menger et al., The Journal of Physical Chemistry 1974, 78 (14): 1387-1390). These results thus provide further support for the view that the large differences in sliding speeds observed for droplets containing single-tailed surfactants such as SDS (above) and DTAB (as described below) result from dynamic and surfactant-induced changes in the orientation of the LC from planar to homeotropic in regions of the SLIPS interface that are in contact with the droplets.

The results of additional experiments characterizing the influence of surfactant concentration, salt concentration, and surfactant structure on the sliding speeds of surfactant-containing droplets on LC-infused SLIPS (FIG. 3) were also consistent with the proposition that orientational changes in the anchoring of LCs can influence droplet sliding behaviors. Past studies have established that the anchoring of LCs at aqueous/LC interfaces is influenced strongly by the areal density of the surfactant molecules adsorbed at the interface and interactions between the surfactant tails and LCs. For example, it has been demonstrated using aqueous-5CB interfaces that, with increasing surfactant concentration, the limiting areal density of surfactant tails at the interface increases and results in homeotropic alignment of the LC (Lockwood et al., Langmuir 2005, 21 (15): 6805-6814; Brake et al., Langmuir 2003, 19 (16): 6436-6442; Brake et al., Langmuir 2002, 18 (16): 6101-6109; Zhong et al., Liquid Crystals 2016, 43 (3): 361-368; Carlton et al., Langmuir 2014, 30 (49): 14944-14953; Ortiz et al., ACS Applied Materials & Interfaces 2020, 12 (26): 29056-29065; Alino et al., Langmuir 2011, 27 (19): 11784-11789; Uline et al., Soft Matter 2010, 6 (21): 5482-5490; and Gupta et al., Langmuir 2009, 25 (4): 2026-2033).

Similar results were obtained by increasing the electrolyte concentration, which can screen electrostatic repulsion between charged surfactant head groups (Brake et al., Langmuir 2003, 19 (16): 6436-6442; Brake et al., Langmuir 2002, 18 (16): 6101-6109; and Gupta et al., Langmuir 2009, 25 (4): 2026-2033). Finally, it has also been reported that both the nature of the hydrophilic head group and the aliphatic chain length of the surfactant can impact the orientation of LCs at aqueous-5CB interfaces (Lockwood et al., Surface Science Reports 2008, 63: 255; Brake et al., Langmuir 2003, 19 (16): 6436-6442; and Zhong et al., Liquid Crystals 2016, 43 (3): 361-368).

Figure 3:
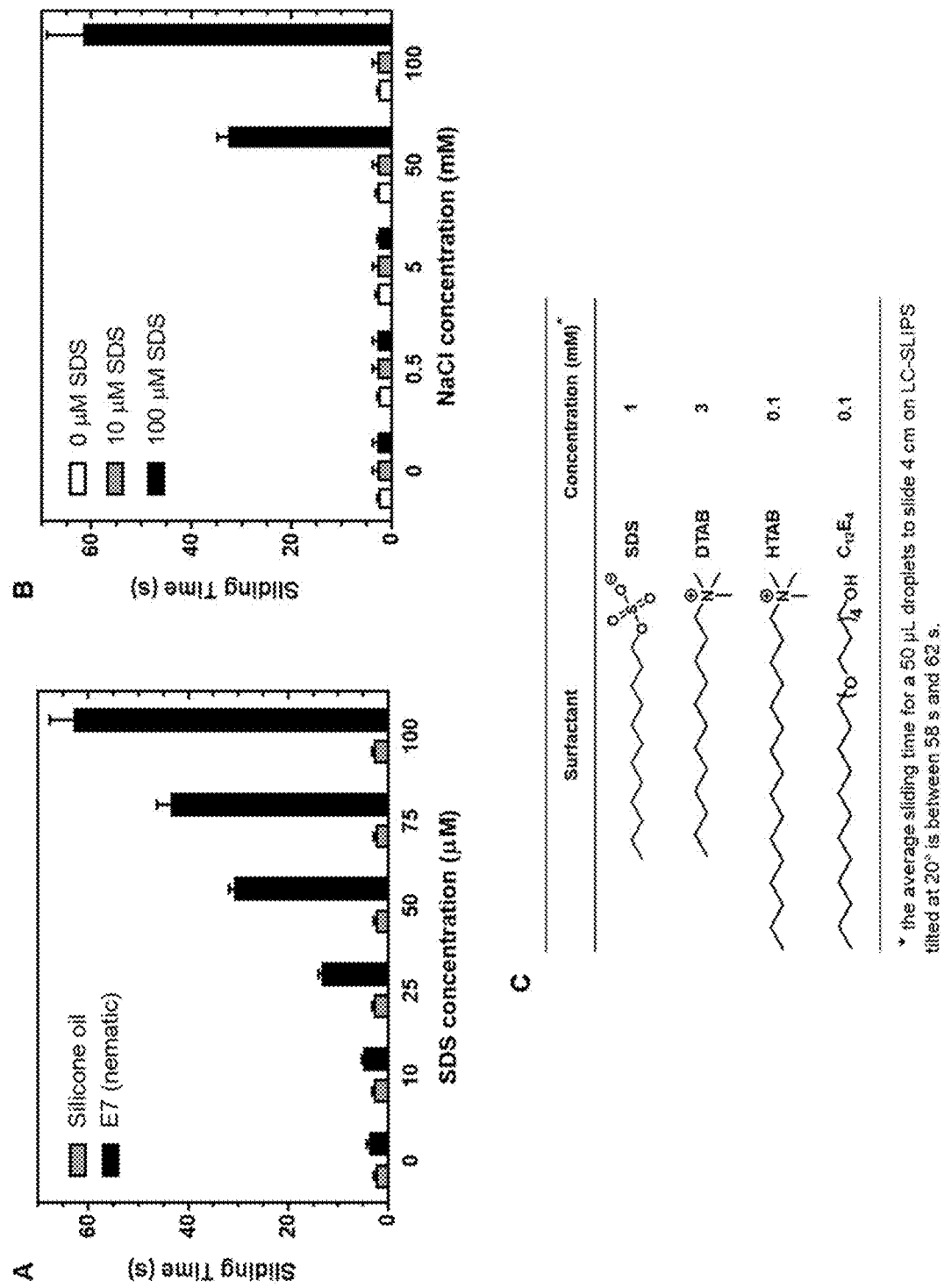
FIG. 3. (Panel A) Plot showing the sliding time of 50 μL PBS droplets containing SDS (10-100 μM) on silicone oil-infused SLIPS (gray) and E7-infused SLIPS (black) tilted at 20°. (Panel B) Plot showing the influence of NaCl concentration (0 to 100 mM) on the sliding time of SDS-containing droplets (0 μM (white), 10 μM (gray), and 100 μM (black)). (Panel C) Table showing bulk concentration of various surfactants (with different head and tail group structure) in water droplets that slid on a E7-infused SLIPS tilted at an angle of 20° at average sliding times between 58 s-62 s (~1 min).
Figure 13:
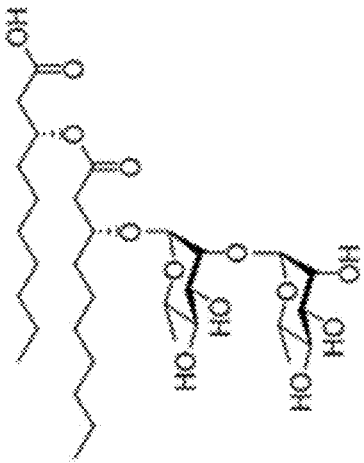
FIG. 13. Plots showing the sliding time of 50 µL PBS droplets containing DTAB (10-100 µM, left) and rhamnolipid (10-50 µM, right) on silicone oil-infused SLIPS (black) and E7-infused SLIPS (grey) tilted at 20°. For the liquid crystal, sliding speed decreased with increase in the concentration of the surfactant.
Figure 13:
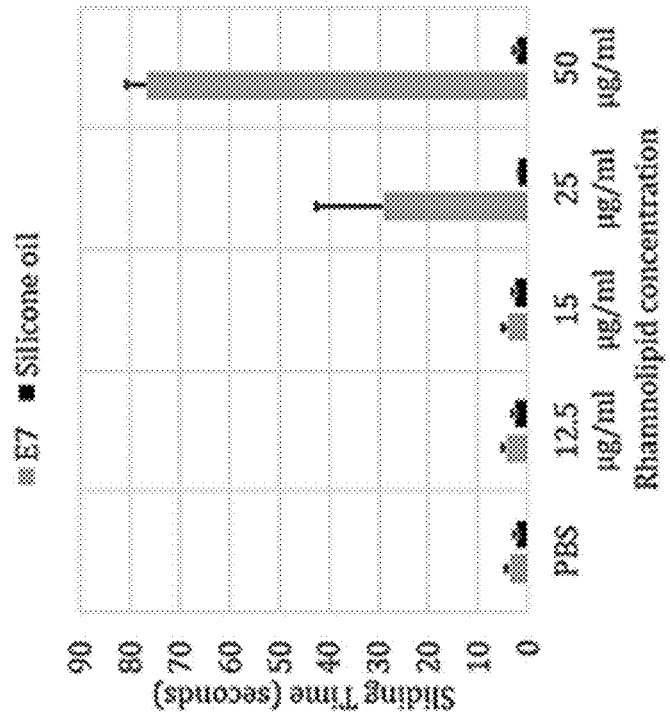
Figure 13:
Figure 13:
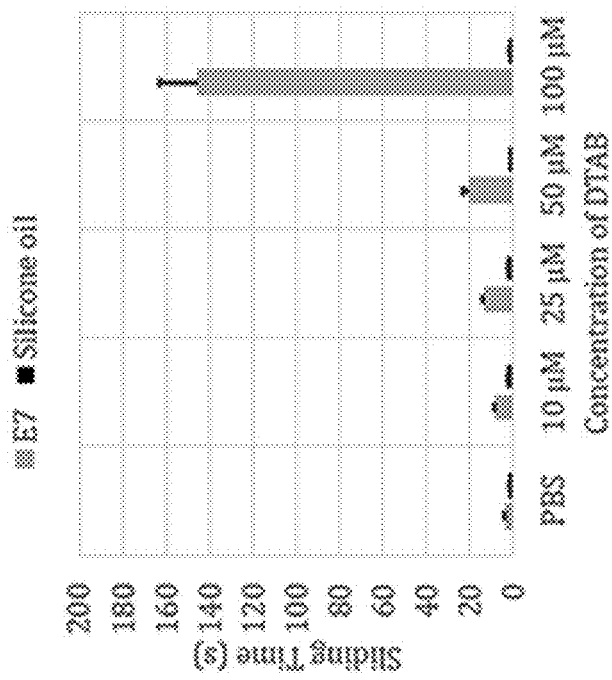
Figure 14:
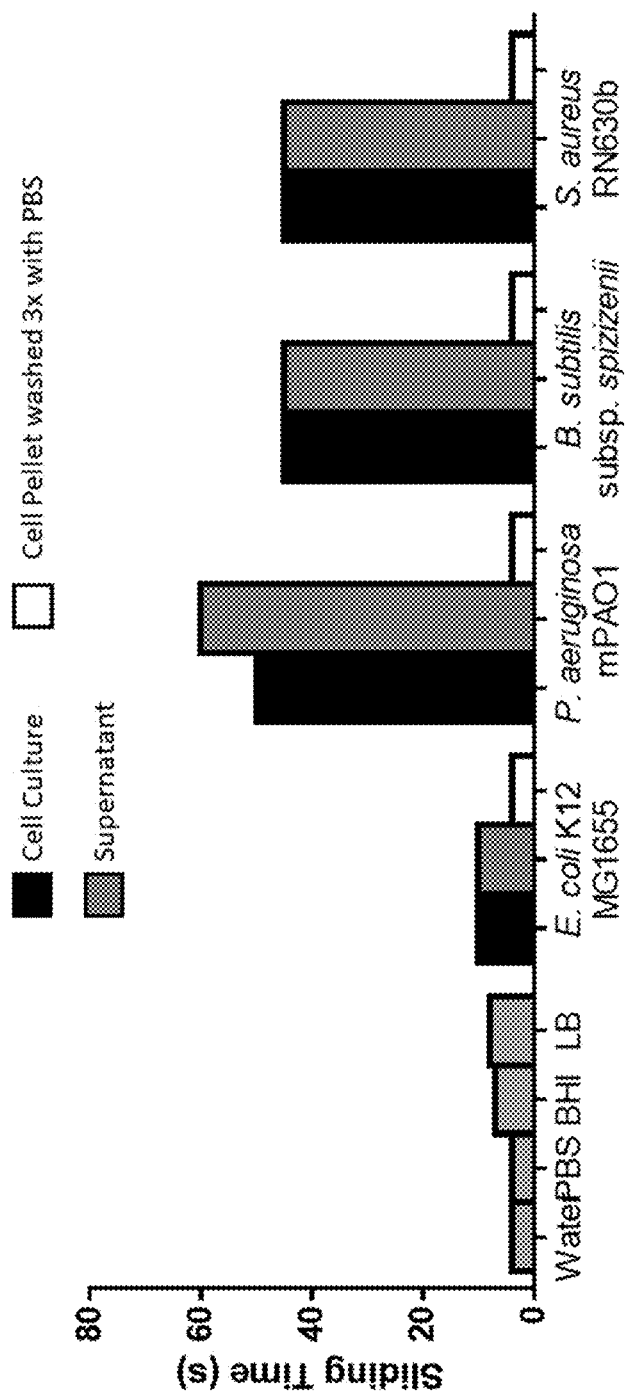
FIG. 14. Plot showing sliding time of 35-45 µL droplets taken from cell cultures, supernatants, and washed cell pellets from *E. coli, P. aeruginosa, B. subtilis,* and *S. aureus* on silicone oil-infused SLIPS and liquid crystal-infused SLIPS. Sliding times on silicone oil-infused SLIPS were approximately 5 seconds for each case.
Figure 15:
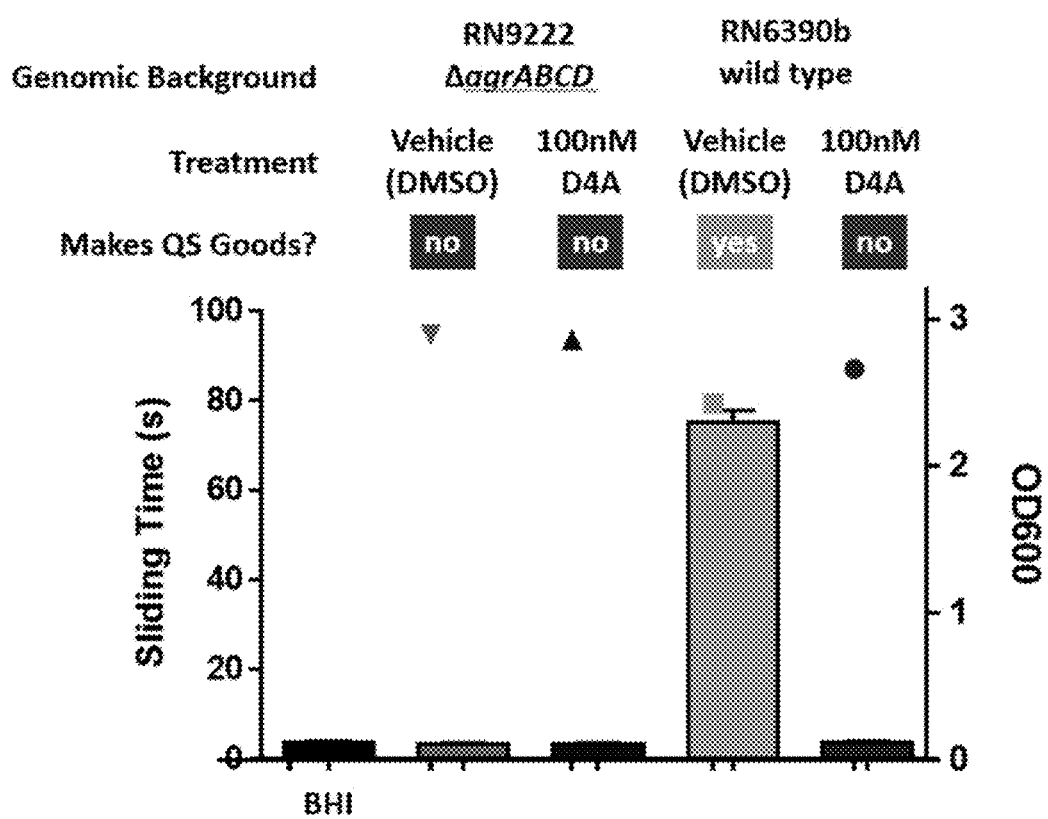
FIG. 15. Plot showing the sliding time of droplets of BHI media and cultures of *S. aureus* QS mutant (RN9222, lacking AgrBD proteins critical for QS), QS mutant cultured with AIP-III D4A, WT (RN6390b), and WT cultured with AIP-III D4A.

As shown in FIG. 3, panel A (black bars), droplet sliding times were observed to increase substantially as the concentration of SDS in droplets of PBS was increased from 0 μM to 100 μM. Droplets of PBS containing 10 μM SDS slid rapidly (over ~5 s) over a distance of 4 cm on LC-infused SLIPS, whereas droplets containing 100 μM SDS exhibited sliding times of ~63 s. The sliding times of SDS-containing droplets exhibited uniform sliding times of ~3 s on PTFE membranes infused with silicone oil regardless of SDS concentration (FIG. 3, panel A; gray bars). Similar effects on sliding times were seen with droplets containing DTAB and rhamnolipid on E7 and silicone oil-infused SLIPS (FIG. 13).

Experiments using droplets containing a fixed concentration of SDS with different concentrations of electrolyte (NaCl) revealed that manipulation of electrolyte concentration also impacts the sliding time of surfactant-containing droplets on LC-infused SLIPS. As shown in FIG. 3, panel B, for 100 μM SDS solutions in water (black bars), the addition of NaCl at 100 mM increases the sliding time by 15 times (~62 s) compared to NaCl at 0.5 mM. Varying the NaCl concentration of water droplets free of SDS over this same concentration range did not impact droplet sliding times (FIG. 3, panel B; white bars). The sliding times of SDS-containing droplets were also insensitive to NaCl concentration at lower concentrations of SDS (e.g., 10 µM; FIG. 3; gray bars).

The influence of surfactant head and tail group structure on droplet sliding speeds was then examined using four different surfactants: SDS, DTAB, HTAB, and the non-ionic surfactant $C_{12}E_4$ (structures shown in FIG. 3, panel C). For these experiments, surfactant solutions were prepared in water to decouple the impact of surfactant structure from that of salt concentration. The sliding times of droplets containing many different concentrations of these four surfactants were measured and sliding times were found to vary considerably as a function of concentration and structure. For simplicity and to permit general comparisons, FIG. 3, panel C reports the concentrations of each surfactant that resulted in average sliding times between 58-62 s (approximately 1 min). For surfactants with different head groups [SDS (anionic), DTAB (cationic), and $C_{12}E_4$ (non-ionic)] but identical aliphatic tail lengths (12 carbons), the measured concentrations were 1 mM, 3 mM, and 0.1 mM respectively. These values correlate with the concentration regime in which these surfactants adsorb strongly at both oil-water and air-water interfaces (Brake et al., Langmuir 2003, 19 (16): 6436-6442; Menger et al., The Journal of Physical Chemistry 1974, 78 (14): 1387-1390; Hsu et al., Langmuir 2000, 16 (7): 3187-3194; and Rehfeld et al., The Journal of Physical Chemistry 1967, 71 (3): 738-745).

The impact of changes in the aliphatic tail length (while keeping the head group constant) on the sliding time of a surfactant-containing droplet on LC-infused SLIPS was also tested. FIG. 3, panel C, shows a comparison of results for DTAB and HTAB, which possess different aliphatic tail lengths (12 vs. 16 carbons, respectively) but identical cationic head groups. The concentration of HTAB required to achieve an average sliding time of ~60 s (100 µM) was found to be ~30 times lower than that for DTAB (3 mM). This result is consistent with those of past studies using LC-infused layer-by-layer coatings and, more broadly, with the fact that as the alkyl chain length of a surfactant increases, the interfacial density of the adsorbed surfactant increases (compared to a shorter-tailed surfactant at a similar bulk concentration) and the fact that longer alkyl chains can penetrate deeper into the LC, which should lead to anchoring of E7 closer to the normal with respect to the aqueous/LC interface. Finally, it was noted that the addition of 100 mM NaCl to solutions of $C_{12}E_4$ did not result in changes to droplet sliding speeds, consistent with the fact that $C_{12}E_4$ is a non-ionic surfactant and, thus, the interfacial density of the adsorbed surfactant should not be affected by the addition of an electrolyte.

Example 5

Naked-Eye Detection of Small-Molecule Amphiphiles and Toxins in Droplets Extracted from Cultures of *P. aeruginosa*. Past studies have demonstrated the potential of different LC-based materials platforms, including planar aqueous/LC interfaces and colloidal LC emulsions of free-floating micrometer-scale LC droplets in water, to sense and report on the presence of different environmental amphiphiles (such as lipids, proteins, and surfactants) with remarkable sensitivity (Popov et al., Journal of Materials Chemistry B 2017, 5 (26): 5061-5078; Lockwood et al., Surface Science Reports 2008, 63: 255; Alino et al. Langmuir 2011, 27 (19): 11784-11789; Carter et al., Langmuir 2015, 31 (47): 12850-12855; Park et al., Colloid and Polymer Science 2014, 292 (5): 1163-1169; and Chang et al., Chemical Communications 2014, 50 (81): 12162-12165).

In those past studies, changes in LC orientation promoted by the adsorption of amphiphiles was generally characterized using polarized light microscopy or by changes in the forward- and side-scattering of light using flow cytometry (Zhong et al., Liquid Crystals 2016, 43 (3): 361-368; Miller et al., Langmuir 2013, 29 (10): 3154-3169; Carter et al., Langmuir 2015, 31 (47): 12850-12855; and Miller et al., Analytical Chemistry 2013, 85 (21), 10296-10303). While these analytical methods are effective, they require specialized and expensive instrumentation and, in general, some degree of technical knowledge to interpret the sometimes-complex results that arise from them. The LC-infused SLIPS reported here offer a new platform that translates factors that promote changes in the anchoring of LCs at aqueous interfaces (e.g., the presence of an amphiphile) to other readily observable macroscale phenomena (e.g., the readily observable rate at which a droplet of water slides across a surface).

The large and substantial differences in the sliding speeds of surfactant-containing and non-surfactant-containing droplets provide a straightforward and visual, 'naked-eye' approach for the detection of surfactants or other amphiphilic contaminants in aqueous environments. This approach would, in general, require no special equipment or expertise to interpret (e.g., a droplet sliding over a short distance within 4 s can be readily distinguished from a droplet that requires 1 min to traverse the same distance). In addition, because sliding speeds are also observed to vary as a function of surfactant concentration (FIG. 3, panel A), it is possible that this approach could also be used to provide estimates of the concentration of an analyte in an aqueous solution using equipment as basic as a stopwatch, or by using computer image analysis.

Figure 9:
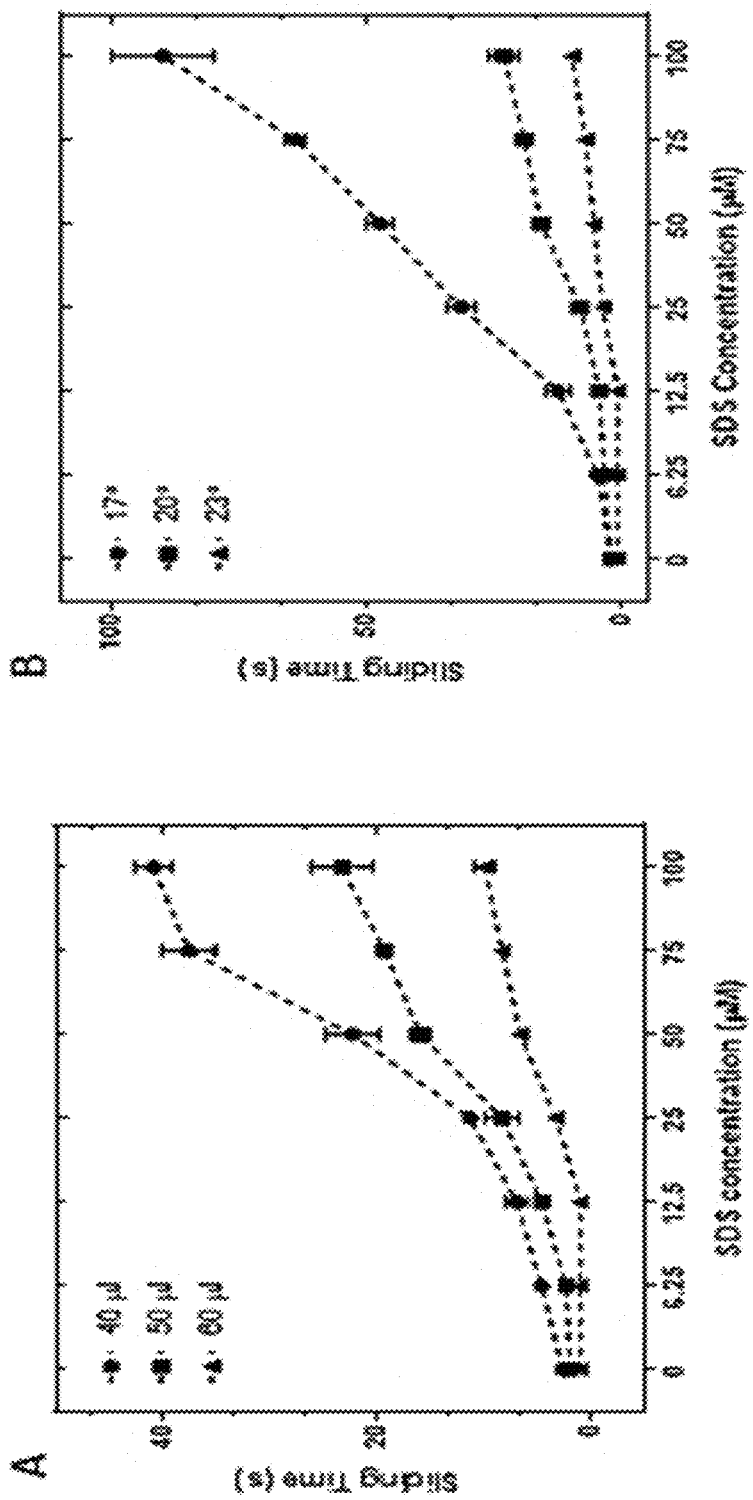
FIG. 9. Plot showing the sliding time as a function of the concentration of SDS in PBS droplets for (A) different droplet volumes (40 µL, 50 µL, and 60 µL) at a fixed tilt angle (20°) and (B) different tilt angles (17°, 20°, and 23°) at a fixed droplet volume (50 µL).

Here, in cases where differences in sliding speeds may be small and more difficult to distinguish, they can be further magnified by varying several simple extrinsic parameters, such as sliding angles or droplet volumes, that also have impacts on sliding times. For example, the difference in sliding time ($\Delta t$) between a 50 µL PBS droplet and a 50 µL droplet of 100 µM SDS (in PBS) increases from 7±2 s to 86±11 s when the sliding angle of the LC-infused SLIPS is reduced incrementally from 23° to 17°. Similarly, decreasing the volume of a droplet of PBS containing 100 µM SDS from 60 µL to 40 µL magnifies the difference in sliding time ($\Delta t$) compared to a PBS droplet from 7±2 s to 37±3 s (see FIG. 9). For charged surfactants, the results discussed above (FIG. 3, panel B) also illustrate that the detection limits of LC-infused SLIPS can also be manipulated by modifying electrolyte concentration. When combined, modifications to both extrinsic and intrinsic parameters can be varied to increase or decrease droplet mobility and, in turn, influence the sensitivity of the response of an LC-infused SLIPS surface. Finally, on a practical note, these materials have the potential to be used and reused multiple times without affecting droplet sliding behaviors because changes in LC anchoring on LC-infused SLIPS are transient and reversible.

To demonstrate proof of concept and explore the potential of this approach to naked-eye detection, a series of additional experiments was performed to determine whether measurements of droplet sliding times on LC-infused PTFE membranes could be used to identify the presence of amphiphilic compounds produced by the bacterium *P. aeruginosa*, a common Gram-negative pathogen that uses the non-ionic amphiphilic small molecule 3-oxo-C12-AHL and the shorter-tailed, non-amphiphilic analog C4-AHL to regulate its quorum sensing (QS) system, and thereby control virulence. *P. aeruginosa* uses QS to regulate important behaviors once they achieve high cell densities, including biofouling and the production of amphiphilic toxins (i.e., rhamnolipid) that can be detrimental in environmental and healthcare settings. These amphiphilic QS signals and virulence factors therefore represent markers not only of the presence of *P. aeruginosa* in a given environment, but also provide useful information about the number of bacteria present and their virulence.

It was recently reported that free-floating microscale droplets of 5CB suspended in aqueous media can be used to detect and report the presence of biologically-relevant concentrations of 3-oxo-C12-AHL and rhamnolipid, as well as an amphiphilic precursor to the biosynthesis of rhamnolipids [3-(3-hydroxyalkanoyloxy)alkanoic acid, (HAA)], using polarized light microscopy and flow cytometry (see FIG. 10, panel A for the structures of these amphiphiles) (Ortiz et al., ACS Applied Materials & Interfaces 2020, 12 (26): 29056-29065). The experiments described here sought to determine whether the amphiphilicity of these compounds could provide a basis for unaided, or naked-eye, detection of these bacterial products by simple measurement of the sliding times of droplets obtained directly from cultures of *P. aeruginosa* on the surfaces of LC-infused SLIPS.

Figure 10:
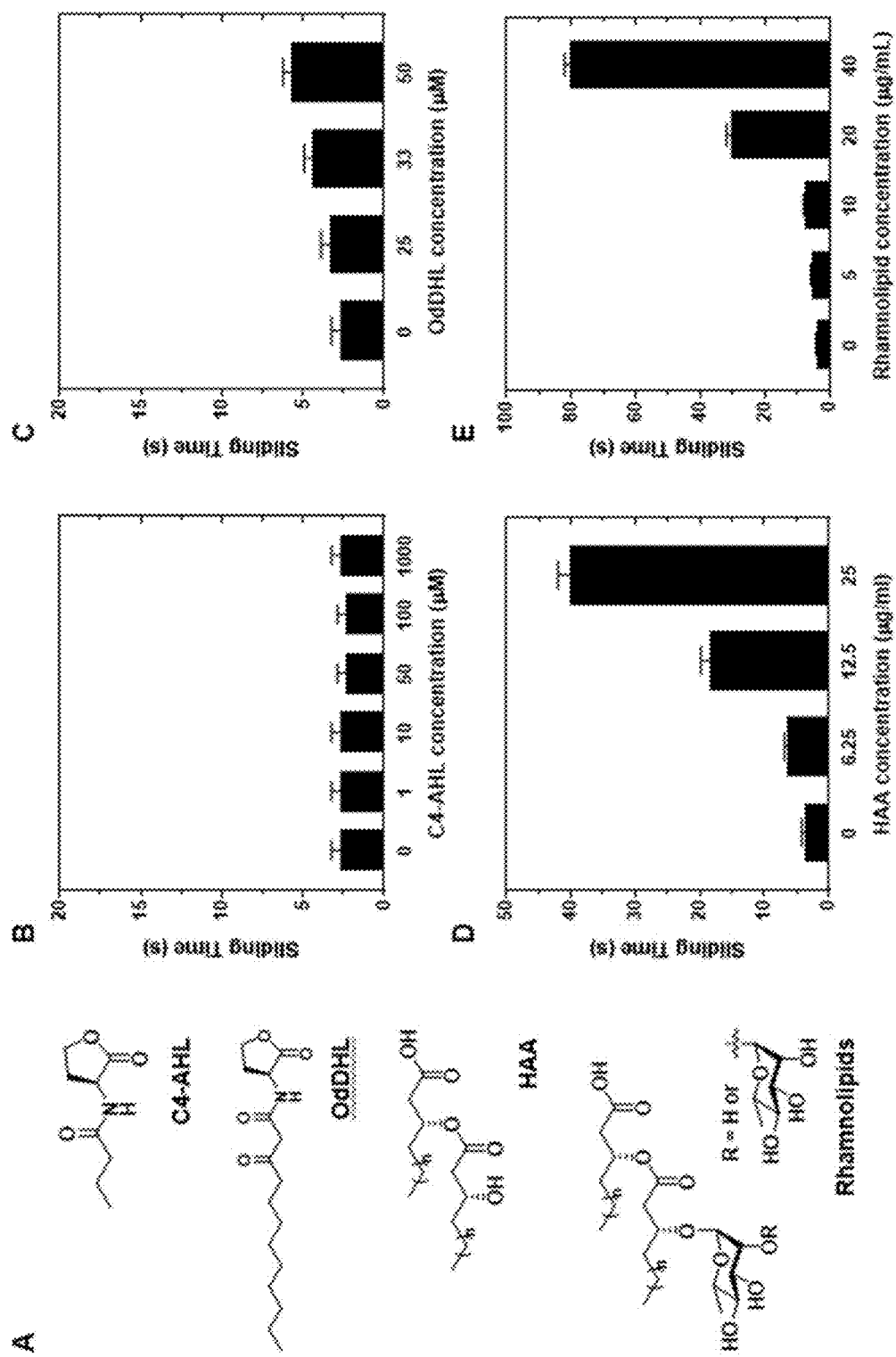
FIG. 10. (Panel A) Structures of the AHLs and bacterial biosurfactants investigated in this study (n=3-11 for rhamnolipid and HAA). HAA was evaluated as a mixture of stereoisomers. (Panels B-E) Plots showing sliding time of droplets of (B) C4-AHL, (C) 3-oxo-C12-AHL, (D) HAA, and (E) rhamnolipids on E7-infused SLIPS. 50 µL droplets of C4-AHL, 3-oxo-C12-AHL and HAA solutions were used for the sliding time measurements and the SLIPS were tilted at angle of 20°. For measuring the sliding time of rhamnolipid solutions, 42 µL droplets were used and the SLIPS were inclined to 15°.

A series of initial experiments was performed to measure the sliding times of 50 µL droplets containing known concentrations of 3-oxo-C12-AHL (over the range of 25-50 µM) and $C_4$-AHL (over the range of 1-1000 µM) as well as rhamnolipid (over the range of 5-40 µg/mL), and HAA (over the range of 6.25-25 µg/mL) on E7-infused SLIPS (see FIG. 10). The concentration ranges used in these experiments were selected to encompass the range of biologically relevant concentrations of these amphiphiles. Solutions of C4-AHL, 3-oxo-C12-AHL, and HAA solutions were prepared in PBS containing 1% (v/v) DMSO to enhance solubility. Inspection of the results in FIG. 10, panels A-B shows that the sliding times of C4-AHL-containing and 3-oxo-C12-AHL-containing droplets are similar compared to those of control droplets (containing only PBS and 1% DMSO) over the range of concentrations used here. These results for C4-AHL are consistent with past results demonstrating that this short-tailed AHL does not promote changes in the configuration of free-floating LC droplet emulsions (Ortiz et al., ACS Applied Materials & Interfaces 2020, 12 (26): 29056-29065). Similar studies of LC droplets demonstrate that 3-oxo-C12-AHL can adsorb at aqueous LC interfaces; the present results for 3-oxo-C12-AHL on the LC-infused SLIPS suggest that the concentrations used here are not sufficient to lead to large changes in the droplet sliding time.

The sliding times of droplets containing 3-oxo-C12-HS (the lactone hydrolysis product of 3-oxo-C12-AHL, an anionic amphiphile that forms naturally in aqueous solution and in cultures of bacteria) were also characterized over the range of 25-50 µM and significant changes relative to control droplets (PBS+1% DMSO) were not observed. Additional experiments using 3-oxo-C12-AHL and 3-oxo-C12-HS at concentrations that are higher than those typically reported in communities of planktonic bacteria (100 µM and 250 µM, respectively) resulted in longer sliding times (~12 s). Further inspection of the results shown in FIG. 10, however, reveals substantial differences in the sliding times of droplets containing HAA (at concentrations ≥12.5 µg/mL, FIG. 10, panel D) or rhamnolipid (at concentration ≥20 µg/mL; FIG. 10, panel E) compared to control droplets (PBS+1% DMSO). For example, droplets containing ≥12.5 µg/mL HAA or 20 µg/mL rhamnolipid slid over a distance of 4 cm in ~18 s or ~30 s, respectively, compared to control droplets, which slid much more rapidly over the same distance (in ~4 s). These results demonstrate that measurements of droplet sliding times on LC-infused SLIPS can be used to report on the presence (or absence) of QS-controlled amphiphiles such as HAA and rhamnolipid in aqueous solutions.

Figure 11:
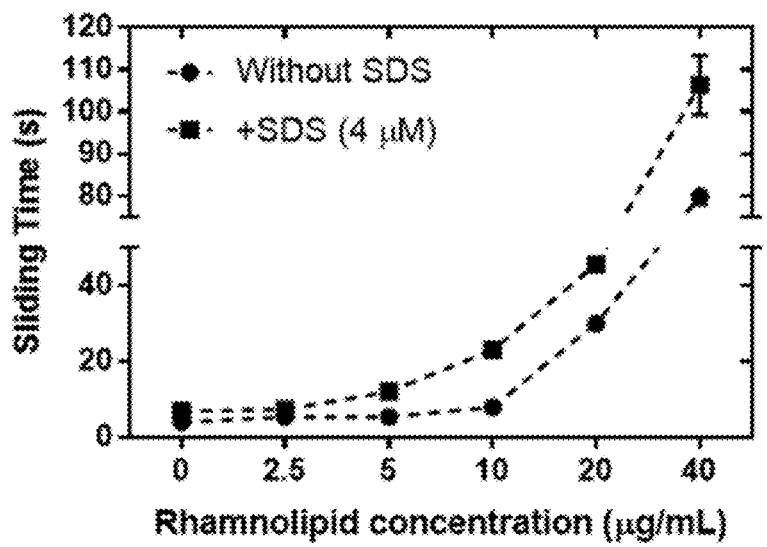
FIG. 11. Plot showing the sliding time of rhamnolipid (0-40 µg/ml) containing droplets on LC-SLIPS with SDS (4 µM; black squares) and without SDS (black circles). 42 µL droplets were used in each case and the SLIPS tilt angle was fixed at 15°.

Past reports demonstrate that LC interfaces decorated by surfactants at areal densities just below the threshold of what is required to promote a change in anchoring can report the presence of additional amphiphilic species at lower concentrations than would be required using 'clean' or 'bare' LC interfaces (i.e., 'priming the surface' of an aqueous/LC interface with low levels of a first surfactant can increase the apparent sensitivity of the interface to a second amphiphile). Based on this, it was reasoned that the sensitivity of droplet sliding times to rhamnolipid concentrations could be increased by 'spiking' rhamnolipid solutions with low (sub-threshold) concentrations of SDS. To explore the potential of this approach, solutions of different concentrations of rhamnolipid also containing 4 µM SDS (a concentration that, by itself, does not change the sliding time of an aqueous droplet; see FIG. 3, panel A and the discussion above) were prepared and the sliding times on E7-infused SLIPS were measured. As shown in FIG. 11, the addition of low concentrations of SDS resulted in a two-fold reduction of the limit of detection for rhamnolipid, from 20 µg/mL to 10 µg/m L. These results suggest additional practical means by which differences in droplet sliding times can be manipulated or magnified to enhance the potential utility of LC-infused SLIPS in the context of sensing.

A series of biological experiments was performed to determine whether LC-infused SLIPS could be used to monitor the production of bacteria-produced amphiphiles in live cultures. For these experiments, two different strains of *P. aeruginosa* were cultured: wild-type (WT) and ΔIasI rhII (the latter is a genetic mutant strain of *P. aeruginosa* lacking genes critical to QS and that is, thus, unable to produce QS-associated factors, including rhamnolipid and HAA). These experiments were performed in LB culture medium with shaking at 37° C. Aliquots of these bacterial cultures were removed at pre-determined time points (6, 12, and 24 hours) and the sliding times required for 35 µL droplets of these samples to slide 4 cm at a 20° incline were measured. Inspection of FIG. 4, panel A, reveals that droplets of cultures of the ΔIasI rhII mutant had short sliding times (~5 s) at incubation times of 6, 12, and 24 hours that were indistinguishable from the sliding time of LB medium alone. This result is consistent with the fact the ΔIasI rhII mutant lacks genes critical to QS and, thus, is unable to produce either HAA or rhamnolipid. Further inspection of FIG. 4 also reveals droplets taken from cultures of the WT mutant after only 6 hours of incubation to slide rapidly (over ~5 s). This result is consistent with the observation of low, sub-quorate populations of bacteria at this early time point that are unable to produce HAA or rhamnolipid.

Figure 4:
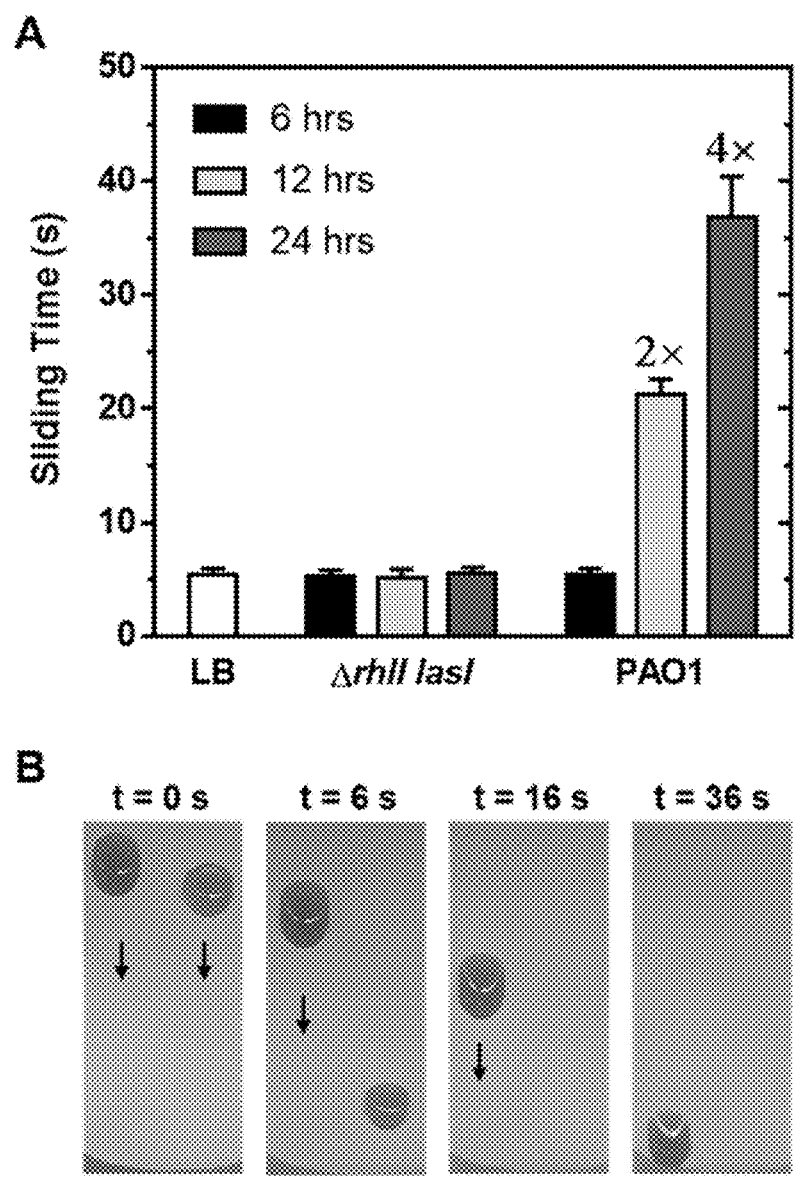
FIG. 4. (Panel A) Plot showing the sliding time of LB media, P. aeruginosa WT (PAO1), and QS-mutant (ΔrhlI lasI) cell culture at 6 h (black), 12 h (light gray), and 24 h (dark gray) on E7-infused SLIPS tilted at an angle of 20°. 2× and 4× denotes the number of folds of dilution of P. aeruginosa WT (PAO1) in LB media before measuring the sliding time. (Panel B) Top-down images showing 35 μL droplets of WT P. aeruginosa culture (4× diluted in LB media before measuring the sliding time; left) and QS-mutant (ΔrhlI lasI, right) at 0 s, 6 s, 16 s, and 36 s on LC-infused.

In contrast, droplets taken from cultures of the WT mutant after 12- and 24-hours of incubation did not slide on LC-infused SLIPS and, instead, spread on the surfaces of these materials, likely due to the presence of a significantly higher concentration of QS-controlled surfactants. Further dilution of these samples with LB medium reduced droplet spreading and enabled meaningful measurements of sliding times. Two-fold dilution of samples taken at 12 hours of incubation of the WT strain resulted in droplet sliding times of ~21 s (FIG. 4, panel A). Samples taken after 24 hours of incubation, which would be expected to contain higher concentrations of HAA and rhamnolipid relative to earlier time points, required additional dilution; four-fold dilution with LB medium yielded sliding times of ~36 s.

Figure 12:
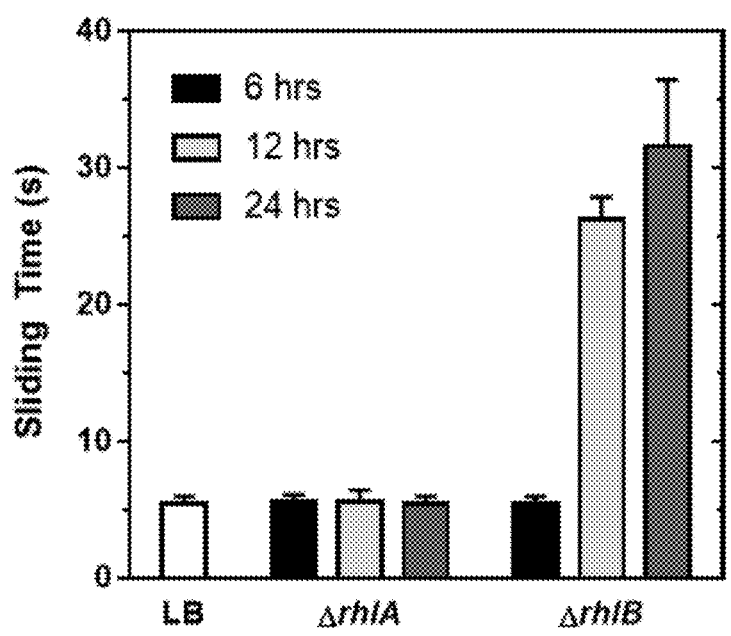
FIG. 12. Plot showing the sliding time of LB media, ΔrhIA, and ΔrhIB at 6 hrs (black), 12 hrs (light gray), and 24 hrs (dark gray). 35 µL droplets were used in each case and the LC-infused SLIPS was tilted to 20°.

These results from experiments on live bacteria are consistent with an increase in the concentration of these QS-controlled amphiphiles in WT *P. aeruginosa* cultures over time. Additional experiments were performed using two other mutant strains (ΔrhIA and ΔrhIB) that lack functional proteins in the rhamnolipid biosynthetic pathway (see FIG. 12). RhIA is upstream of RhIB, so the ΔrhIB mutant accumulates the intermediate HAA and does not convert it into rhamnolipid, while both HAA and rhamnolipid production is abrogated in ΔrhIA. As expected, droplets of ΔrhIA collected after different incubation periods of 6, 12 and 24 hours exhibited sliding times on LC-infused SLIPS that were fast and indistinguishable from those of LB medium alone (~5 s), whereas an increase in sliding times was observed in samples collected from ΔrhIB cultures at 12 and 24 hours, likely due to the presence of HAA (FIG. 12).

When combined, the results of these experiments demonstrate that measurements of the sliding times of droplets extracted directly from bacterial cultures on LC-infused SLIPS can be used to identify the presence of two amphiphilic factors (rhamnolipid and HAA) in cultures of *P. aeruginosa* and, in particular, distinguish between and monitor changes in the growth of sub-quorate and quorate populations of this human pathogen (see FIG. 4, panel B). The results generated using the *P. aeruginosa* mutants described above also demonstrate that changes in droplet sliding times reported here are the result of the production of HAA and rhamnolipid, and not the result of other compounds produced by bacteria under these growth conditions. These large differences in droplet sliding times allow the presence and production of bio-surfactant toxins to be monitored visually and unambiguously in the absence of any additional specialized equipment or assays.

Example 6

Detection and Monitoring of Amphipathic Peptide Toxins Produced by Cultures of *S. aureus*. A series of experiments was performed to determine whether the results reported above could be used to identify the presence of amphipathic toxins produced by another common bacterium, the Gram-positive pathogen *Staphylococcus aureus*. It is well known that *S. aureus* produces a family of amphipathic α-helical peptides known as phenol soluble modulins (PSMs), also under the control of QS. Amphipathic peptides differ substantially in structure from single-tailed surfactants, and it was not clear at the outset of these studies whether PSMs could adsorb at aqueous/LC interfaces and change the anchoring of LCs.

Figure 5:
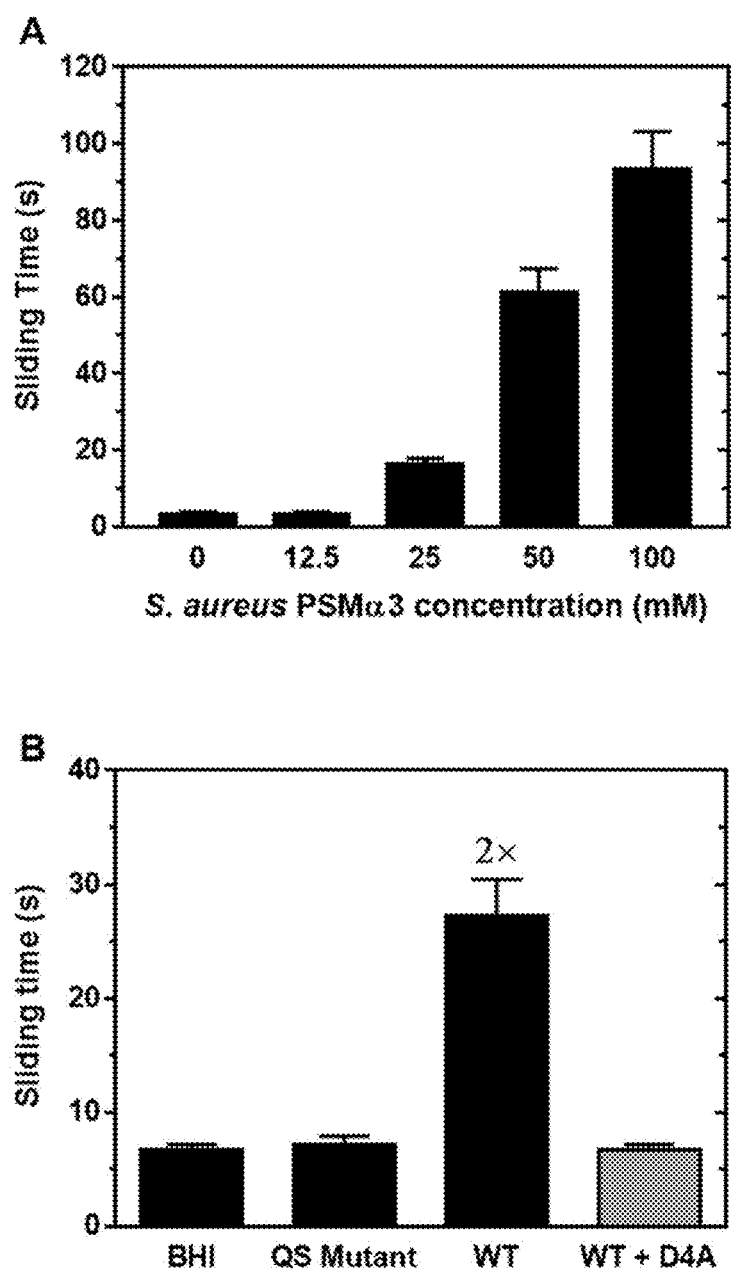
FIG. 5. (Panel A) Plot showing the sliding time of 50 μL PBS droplets containing different concentrations of PSM-α3 (0 mM, 12.5 mM, 25 mM, 50 mM, and 100 mM) on LC-infused SLIPS tilted at 20°. (Panel B) Plot showing the sliding time of droplets of BHI media and cultures of S. aureus QS mutant (lacking AgrBD, proteins critical for QS), WT (2× diluted in BHI media before measuring the sliding time), and WT cultured with AIP-III D4A (at a concentration of 1 μM). All the S. aureus strains were cultured for 24 hours at 37° C. before measuring the sliding time.

Solutions of PSM-α3, one of several PSMs produced by *S. aureus* at high cell densities, were prepared at concentrations ranging from 12.5 mM to 100 mM in PBS and measured the sliding times of the droplets of these solutions on E7-infused SLIPS. As shown in FIG. 5, panel A, the sliding times of PSM-containing droplets increased substantially with an increase in the concentration of PSM. For example, the sliding time increased from ~16 s to ~93 s with an increase in the concentration of PSM-α3 from 25 mM to 100 mM (FIG. 5, panel A), suggesting that PSMs can interact with LCs and induce changes in the anchoring of LCs in ways that, at the least, lead to large changes in sliding behaviors that are similar to those observed above using conventional surfactants.

Additional experiments were performed to determine whether LC-infused SLIPS could detect the presence of PSMs in live cultures of *S. aureus* and, thereby, provide methods to monitor QS in communities of this pathogen in ways analogous to the studies of *P. aeruginosa* above. For these experiments, a *S. aureus* WT strain and a QS mutant strain (lacking AgrBD, proteins critical for QS) were cultured for 24 hours and the sliding times of droplets of these cultures on LC-infused SLIPS were measured. Droplets obtained from cultures of the WT strain slid significantly more slowly (over ~27 s) compared to droplets obtained from cultures of the QS mutant strain (~7 s), consistent with the expected presence of PSMs in the WT culture (see FIG. 5, panel B). Experiments were also performed in which a known inhibitor of QS (AIP-III D4A, at a concentration of 1 μM) was added to cultures of the WT *S. aureus* strain and the sliding time of a droplet of the culture was measured after 24 hours. AIP-III D4A has been demonstrated to fully inhibit *S. aureus* QS at concentrations ≥1 nM. The sliding times of droplets of cultures incubated in the presence of this inhibitor were observed to be comparable (~7 s) to those of the QS mutant (see FIG. 5, panel B).

Taken together, these results demonstrate that readily observed changes in the sliding times of droplets of *S. aureus* cultures can be used to not only detect the presence of PSMs and quorate populations of bacteria, but also identify the presence (or absence) of synthetic chemical inhibitors of QS. These results thus also suggest a potential basis for the development of straightforward droplet-based bio-analytical screening assays that could be used as a tool to identify new synthetic inhibitors of bacterial QS.

Example 7

Detection of Anti-Microbial Peptides, Peptide Primary and Secondary Structures, and Enzymatic Activity Using LC-Infused SLIPS Antimicrobial peptides (AMPs), have been shown to exhibit antifungal activity but have not been effective as pharmaceuticals because of low activity and selectivity in physiologically relevant environments. However, studies on α-peptide AMPs have revealed that hydrophobicity and helicity affect the activity and selectivity of β-peptides against fungal pathogens, such as *C. albicans* (Lee et al., ACS Chem. Biol. 2014, 9(7): 1613-1621). These results reveal both antifungal activity and hemolysis were correlated to hydrophobicity, with intermediate levels of hydrophobicity leading to high antifungal activity and high selectivity toward *C. albicans*. In particular, this study examined two similar β-peptides, labeled A2 and V2, that differed only by two amino acid side chains resulting in the two peptides having different hydrophobicity. The A2 peptide was less hydrophobic while the V2 peptide was more hydrophobic. The peptides also differed in that the A2 peptide had a minimal inhibitory concentration (MIC) value of >128 μg/m L, while the V2 peptide had a MIC value of 8 μg/mL.

Figure 16:
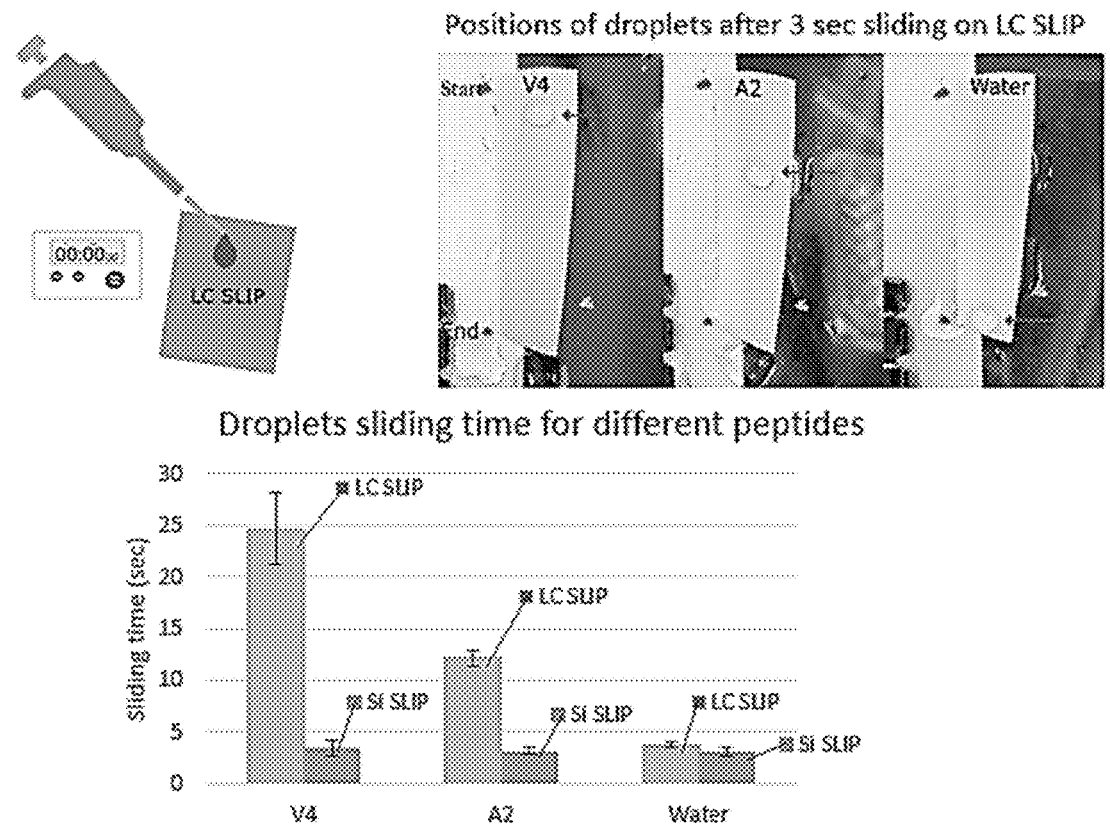
FIG. 16. The top panel shows water droplets containing A2 and V2 β-peptides (see Lee et al., ACS Chem. Biol. 2014, 9(7): 1613-1621) sliding on liquid crystal-infused SLIPS (LC SLIP) material. The center panel provides the sliding times needed to travel to the end of the material for the LC SLIP compared to a similar silicone oil-infused SLIP (Si SLIP). The bottom panel shows the positions of simultaneously released V4, A2 and water droplets after three seconds on both LC and Si SLIP materials. Where little or no difference was observed on the Si SLIP, the more hydrophobic V4 droplet traveled a significantly smaller difference on the LC SLIP.
Figure 16:
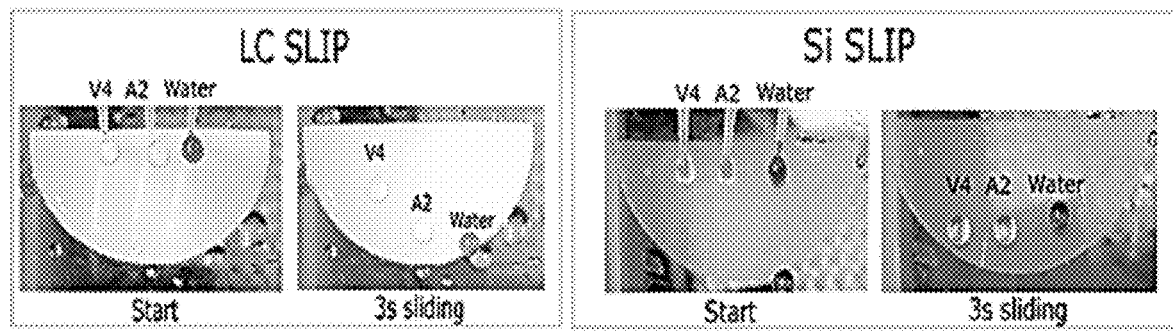

Accordingly, β-peptides and other peptides having potential anti-fungal and anti-microbial properties can be detected and separated based on their relative hydrophobicity and/or amphiphilicity using SLIPS materials. FIG. 16 shows sliding times of water droplets containing the A2 and V2 β-peptides on liquid crystal-infused SLIPS (LC SLIP) and silicone oil-infused SLIPS (Si SLIP). Significantly greater separation time between the V4 and A2 droplets was observed for the LC SLIPS than on similar SLIPS infused with silicone oil.

Figure 17:
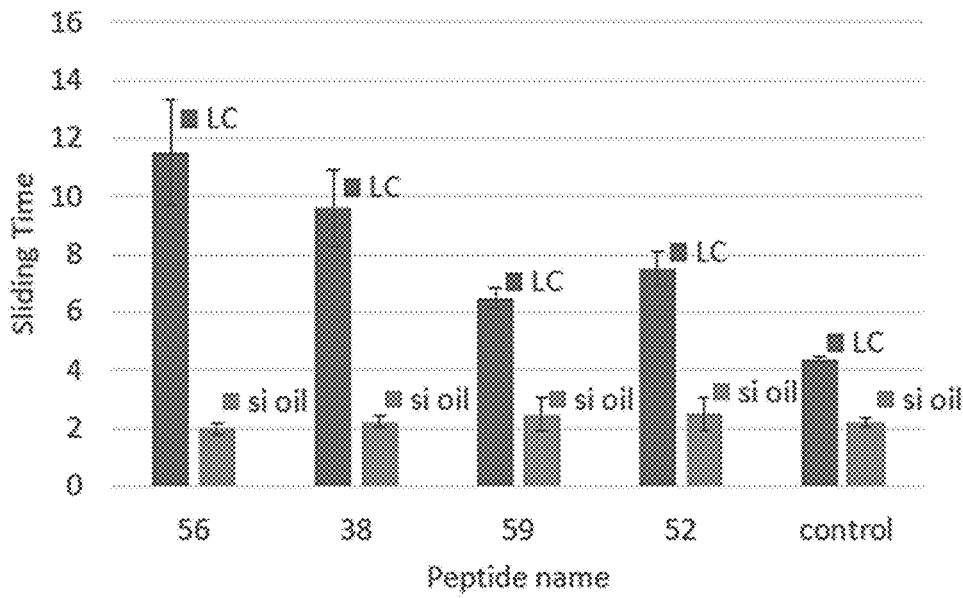
FIG. 17. Sequences and α/β motifs of various peptides having the same linear sequence of side chains but with different sequences of α or β peptide backbone linkages. Plot showing sliding times of droplets containing the V4 and A2 peptides on liquid crystal-infused SLIPS (LC SLIP) and silicone oil-infused SLIPS (Si SLIP). The peptides had different sliding times as a result of the different structures even though the peptides shared the same linear sequence of amino acid side chains.

FIG. 17 similarly shows that LC-infused SLIPS produced greater separation times than silicone oil-infused SLIPS for several peptides having the same sequence but differing in the number and placement of α and β peptide linkages in the backbone. These peptides exhibited different sliding times, indicating that the LC-infused SLIPS are able to distinguish peptides based on these differences in structure. Additionally, these studies demonstrate that LC-infused SLIPS are able to produce sliding times and adhesion characteristics not produced using other SLIPS materials.

Figure 18:
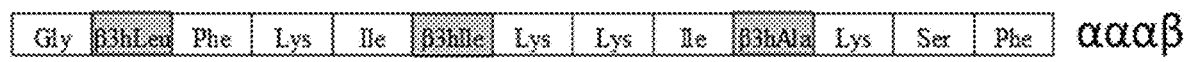
FIG. 18. Plot comparing the sliding times on liquid crystal-infused SLIPS (LC SLIP) and silicone oil-infused SLIPS (Si SLIP) of a peptide digested with different proteases (e.g., no digestion, Pronase E digested, trypsin digested, Pronase E control, and trypsin control).
Figure 18:
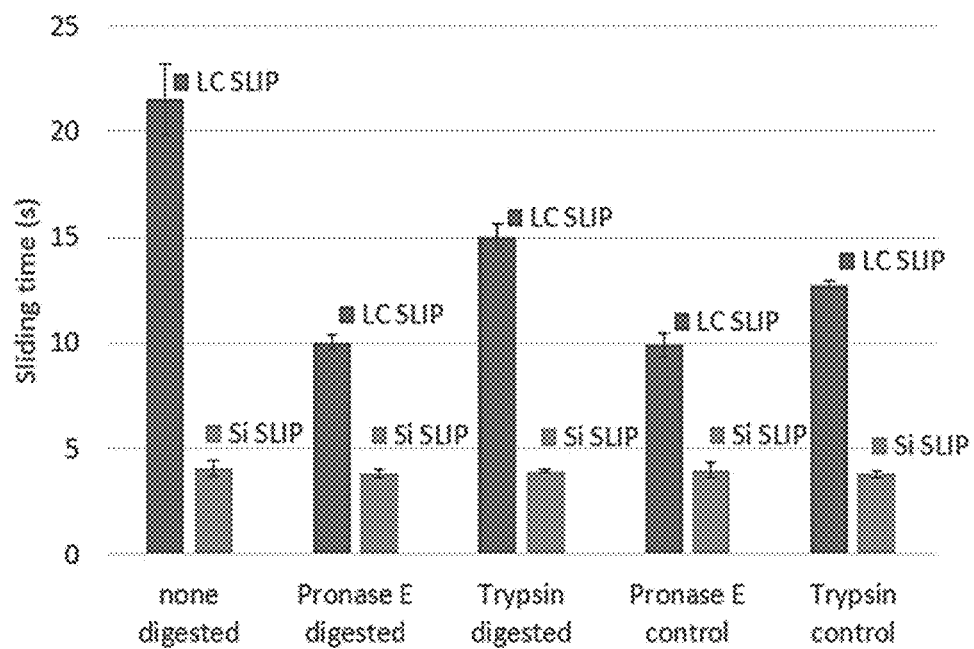

Furthermore, since similar proteins can be distinguished and separated based on their amphiphilic properties and differences in their primary or secondary structures, liquid crystal-infused SLIPS can be used to detect enzymatic protein digestion. FIG. 18 shows the sliding times of a water droplet containing a peptide after treatment with different proteases. The silicone oil-infused SLIPS did not result in noticeably different sliding times (even with the non-digested protein), with the sliding times for each sample being under 5 seconds. In contrast, the liquid crystal-infused SLIPS produced sliding times ranging from 10 seconds to over 20 seconds. These results suggest that liquid crystal-infused SLIPS can be used to provide rapid monitoring of protein digestions and other enzymatic activity, even by using a naked eye test.

Example 8

Droplet Evaporation on LC-Infused SLIPS

One embodiment of utilizing SLIPS to detect the presence of hydrophobic or amphiphilic molecules involves placing a droplet of a sample liquid on the surface of the SLIP and allowing the droplet to slide off or along the surface of the material. This can be performed with the surface of the SLIP placed vertically or at a slight angle from horizontal. Alternatively, the SLIP may be placed horizontally (e.g., an angle of 0°) so that the droplet does not slide or move along the surface. The droplet will eventually evaporate depositing any impurities or molecules on the surface as the droplet contracts. However, the impurities and molecules will produce different deposition patterns from the evaporative process based on the hydrophobicity or amphiphilic properties of the impurities or molecules and the interaction with the SLIPS material.

Figure 19:
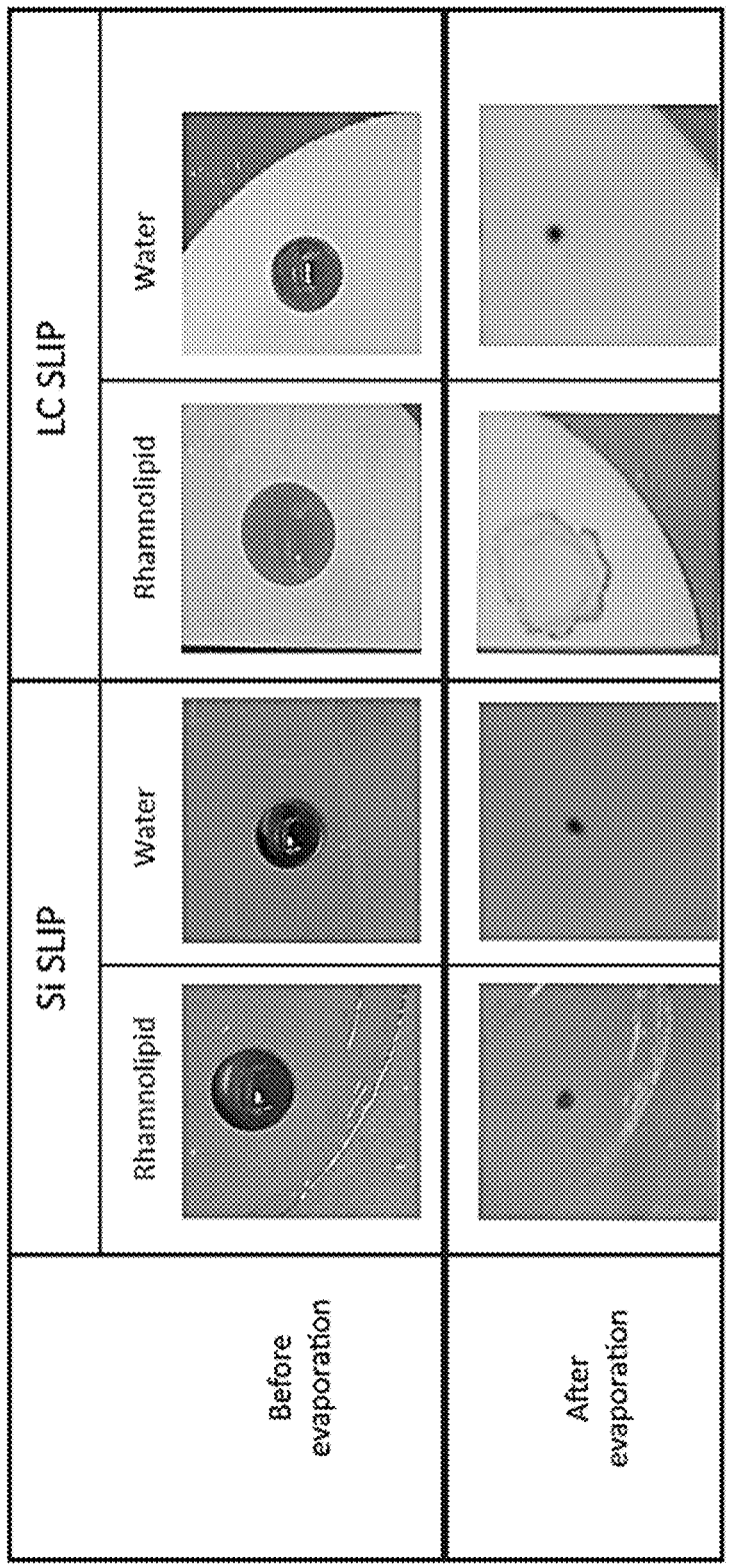
FIG. 19. Images (before evaporation and after evaporation) of water droplets and water droplets containing rhamnolipid placed on horizontal LC-infused SLIPS (LC SLIP) and Si-infused SLIPS (Si SLIP). The images taken after evaporation of the droplets show that the droplets containing rhamnolipid placed on the LC SLIP produced a deposition pattern not seen with the water droplets or the rhamnolipid droplet placed on the Si SLIP.

For example, FIG. 19 shows liquid droplets of water and droplets of water containing rhamnolipid placed on horizontal liquid crystal-infused SLIPS (LC SLIP) and silicone oil-infused SLIPS (Si SLIP). As can be seen in the images taken after evaporation, the droplet containing the rhamnolipid placed on the LC SLIP produced a distinctive pattern not seen with the water droplets or the rhamnolipid droplet placed on the Si SLIP.

Thus, the presence of hydrophobic and/or amphiphilic materials within a liquid droplet can be determined by imaging or analyzing (including in some instances by using a naked eye test) the evaporation patterns.

Summary and Conclusions. The above experiments demonstrate that thermotropic LCs can be infused into microporous PTFE membranes to design slippery liquid-infused surfaces that can detect, monitor, and report on the presence of natural and synthetic amphiphiles in aqueous solution. In contrast to the behaviors of aqueous droplets on the surfaces of conventional slippery surfaces infused with isotropic oils, aqueous droplets slide on LC-infused SLIPS at speeds that depend strongly upon the presence, concentrations, and/or structures of dissolved amphiphiles. Sliding times of droplets on the LC-infused PTFE membranes reported in these experiments increase substantially—from times on the order of several seconds to times on the order of a minute—with increasing concentration of amphiphile. These large differences permit straightforward measurements of droplet sliding times to be used to estimate the concentration of an amphiphile in the droplet. The results also reveal several other intrinsic and extrinsic parameters that can be used to further manipulate (e.g., speed up or slow down) droplet sliding times and, thereby, increase sensitivity or discriminate among amphiphiles of similar structure. Overall, these results are consistent with a physical picture that involves transient and reversible changes in the interfacial orientation of the anisotropic LCs at air/water interfaces mediated by the interfacial adsorption of amphiphiles to the LCs. These results also suggest that this approach has the potential to be general, and that LCs could likely be used in combination with other porous or rough surfaces typically used to prepare other SLIPS and LIS to introduce new and useful functions.

The materials reported here are straightforward to prepare, can be applied or transferred to a variety of secondary surfaces, and permit the unaided or 'naked-eye' detection and discrimination of amphiphilic contaminants in aqueous environments without the need for additional equipment or assays (in the case of large differences in sliding speeds) or with equipment that is no more sophisticated than a stopwatch (in cases where smaller differences in sliding speed may be observed). These features, combined with the low cost and ease of preparation of these materials, suggest opportunities to deploy these materials in the field and in low resource environments (e.g., ranging from clinics to water sampling studies to school science classes). To explore the feasibility of this approach and provide proof of concept in an applied context, the utility of these LC-infused surfaces were demonstrated for naked-eye detection and monitoring of the production of small-molecule and peptidic amphiphilic bio-toxins in small droplets of fluid extracted directly from cultures of $P.$ $aeruginosa$ and $S.$ $aureus$, two clinically important bacterial pathogens. The ability of these LC-infused materials to translate molecular interactions at aqueous/LC interfaces into large and readily-observed, unambiguous changes in the sliding times of small aqueous droplets could open the door to new applications for anti-fouling, liquid-infused materials in the context of environmental sensing and in many other fundamental and applied areas.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that the use of such terms and expressions exclude any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A liquid crystal-infused material comprising:
    a) a lubricating liquid, wherein the lubricating liquid is a thermotropic liquid crystal immiscible or substantially immiscible with aqueous fluids;
    b) a solid substrate able to immobilize or host the lubricating liquid, wherein the lubricating liquid wets and coats at least a portion of the substrate, wherein the substrate is a nanoporous or microporous polytetrafluoroethylene (PTFE) membrane, and wherein the lubricating fluid at least partially fills the pores of the substrate;
    wherein the portion of the substrate coated by the lubricating fluid forms a slippery surface able to allow droplets of various materials to move across the slippery surface.

2. The material of claim 1, wherein the thermotropic liquid crystal comprises 4-cyano-4'-n-pentyl-biphenyl (5CB), 4-cyano-4'-n-heptyl-biphenyl (7CB), 4-cyano-4'-n-octyl-biphenyl (8CB), 4-cyano-4'-n-oxyoctyl-biphenyl (8OCB), 4-cyano-4''-n-pentyl-terphenyl (5CT), or combinations thereof.

3. The material of claim 1 further comprising a solid support formed into a tube, wherein the substrate and lubricating liquid are deposited on the inner surface of the tube.

4. The material of claim 1, wherein the droplets comprise water and an amphiphilic or lipophilic molecule.

5. The material of claim 1, wherein the droplet comprises one or more of the following: suspended particles, viruses, vesicles, polymers, proteins, peptides, microorganisms, or combinations thereof.

6. The material of claim 1, wherein the thermotropic liquid crystal exhibits planar anchoring at aqueous/liquid crystal interfaces when an analyte is not present in an aqueous fluid, and exhibits homeotropic anchoring at aqueous/liquid crystal interfaces when the analyte of interest is present in the aqueous fluid, wherein the analyte comprises an amphiphilic or lipophilic small molecule, a macromolecule, a microorganism, a suspended particle, a virus, a vesicle, a polymer, a protein, a peptide, or combinations thereof.

7. The material of claim 6, where the droplets move across the slippery surface more slowly when an analyte is present compared to when an analyte of interest is not present.

8. The material of claim 1, wherein the droplets are able to move across the slippery surface when the slippery surface is at an angle of 10° or less.

9. A method for detecting an analyte, substance, or impurity in a sample liquid comprising the steps of:
    a) providing a sensor having a first surface area comprising:
        i) a lubricating liquid, wherein the lubricating liquid is a thermotropic liquid crystal immiscible or substantially immiscible with aqueous fluids;
        ii) a solid substrate able to immobilize or host the lubricating liquid, wherein the lubricating liquid wets and coats at least a portion of the substrate, wherein the substrate is a nanoporous or microporous polytetrafluoroethylene (PTFE) membrane, and wherein the lubricating fluid at least partially fills the pores of the substrate, and wherein the portion of the substrate coated by the lubricating fluid forms a slippery surface able to allow droplets of liquids to move across the slippery surface in a manner dependent on the chemical composition of the droplet;

b) providing said sample liquid to said first surface area;

c) comparing the mobility of the sample liquid on said first surface area to a control sample or known standard of said sample liquid, wherein a change in the mobility of said sample liquid to said first surface area indicates an analyte, substance, or impurity in said sample liquid.

10. The method of claim 9, wherein the thermotropic liquid crystal comprises 4-cyano-4'-n-pentyl-biphenyl (5CB), 4-cyano-4'-n-heptyl-biphenyl (7CB), 4-cyano-4'-n-octyl-biphenyl (8CB), 4-cyano-4'-n-oxyoctyl-biphenyl (8OCB), 4-cyano-4"-n-pentyl-terphenyl (5CT), or combinations thereof.

11. The method of claim 9, wherein the analyte, substance, or impurity is an amphiphilic molecule or particle.

12. The method of claim 9, wherein the analyte, substance, or impurity is a peptide.

13. The method of claim 9, wherein the analyte, substance, or impurity is selected from the group consisting of: suspended particles, viruses, vesicles, polymers, proteins, peptides, microorganisms, or combinations thereof.

14. The method of claim 9, wherein comparing the mobility of said sample liquid on said first surface area comprises comparing a time said sample liquid travels across said first surface area to time the control sample or known standard of said sample liquid travels across said first surface area.

15. The method of claim 9, further comprising measuring sliding times of one or more droplets of said liquid sample and one or more droplets of the control sample or known standard on a fixed length of the slippery surface and at a fixed angle, wherein the angle is selected from 1° to 20°.

16. The method of claim 9, wherein comparing the mobility of said sample liquid comprises placing one or more droplets of the liquid sample and one or more droplets of the control sample or known standard on said first surface area, at least partially evaporating the droplets of the liquid sample and droplets of the control sample or known standard to form evaporation patterns on said first surface area, and comparing one or more evaporation patterns formed from the liquid sample to one or more evaporation patterns formed from the control sample or known standard.

17. The method of claim 9, further comprising adding an agent to said sample liquid, wherein the addition of the agent improves levels of detection of the analyte, substance, or impurity present in said sample liquid.

18. The method of claim 17, wherein the agent is added to said sample liquid prior to providing said sample liquid to said first surface area, and the agent physically or chemically interacts with the analyte, substance, or impurity present in said sample liquid and increases or decreases the mobility of said sample liquid on said first surface area.

19. The method of claim 18, wherein the agent is a surfactant that slows or stops the mobility of said sample liquid on said first surface area when the analyte, substance, or impurity is present in said sample liquid.

20. The method of claim 18 wherein the agent increases the mobility of said sample liquid on said first surface area when the analyte, substance, or impurity is present in said sample liquid.

21. The method of claim 17, wherein the agent is a fluorescent compound or dye.

* * * * *